(12) United States Patent
Lindsey et al.

(10) Patent No.: US 10,836,774 B2
(45) Date of Patent: Nov. 17, 2020

(54) METHODS FOR MAKING BACTERIOCHLORIN MACROCYCLES COMPRISING AN ANNULATED ISOCYCLIC RING AND RELATED COMPOUNDS

(71) Applicant: North Carolina State University, Raleigh, NC (US)

(72) Inventors: Jonathan S. Lindsey, Raleigh, NC (US); Shaofei Zhang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/464,728

(22) PCT Filed: Nov. 27, 2017

(86) PCT No.: PCT/US2017/063251
§ 371 (c)(1),
(2) Date: May 29, 2019

(87) PCT Pub. No.: WO2018/102252
PCT Pub. Date: Jun. 7, 2018

(65) Prior Publication Data
US 2019/0308985 A1 Oct. 10, 2019

Related U.S. Application Data

(60) Provisional application No. 62/428,364, filed on Nov. 30, 2016.

(51) Int. Cl.
| | |
|---|---|
| *C07D 487/22* | (2006.01) |
| *A61P 35/00* | (2006.01) |
| *A61K 31/409* | (2006.01) |

(52) U.S. Cl.
CPC .......... *C07D 487/22* (2013.01); *A61K 31/409* (2013.01); *A61P 35/00* (2018.01)

(58) Field of Classification Search
CPC .................................................. C07D 487/22
See application file for complete search history.

(56) References Cited

U.S. PATENT DOCUMENTS

| | | |
|---|---|---|
| 3,710,795 A | 1/1973 | Higuchi et al. |
| 3,817,837 A | 6/1974 | Rubenstein et al. |
| 3,927,193 A | 12/1975 | Hansen et al. |
| RE28,819 E | 5/1976 | Thompson |
| 4,044,126 A | 8/1977 | Cook et al. |
| 4,179,337 A | 12/1979 | Davis et al. |
| 4,328,245 A | 5/1982 | Yu et al. |
| 4,331,647 A | 5/1982 | Goldenberg |
| 4,348,376 A | 9/1982 | Goldenberg |
| 4,358,603 A | 11/1982 | Yu |
| 4,361,544 A | 11/1982 | Goldenberg |
| 4,364,923 A | 12/1982 | Cook et al. |
| 4,374,925 A | 2/1983 | Litman et al. |
| 4,409,239 A | 10/1983 | Yu |
| 4,410,545 A | 10/1983 | Yu et al. |
| 4,414,209 A | 11/1983 | Cook et al. |
| 4,444,744 A | 4/1984 | Goldenberg |
| 4,468,457 A | 8/1984 | Goldenberg |
| 4,474,893 A | 10/1984 | Reading |
| 4,479,895 A | 10/1984 | Auditore-Hargreaves |
| 4,522,811 A | 6/1985 | Eppstein et al. |
| 4,624,846 A | 11/1986 | Goldenberg |
| 4,818,709 A | 4/1989 | Primus et al. |
| 4,946,778 A | 8/1990 | Ladner et al. |
| 5,033,252 A | 7/1991 | Carter |
| 5,052,558 A | 10/1991 | Carter |
| 5,059,415 A | 10/1991 | Neuwelt |
| 5,323,907 A | 6/1994 | Kalvelage |
| 5,441,827 A | 8/1995 | Gratzel et al. |
| 5,681,811 A | 10/1997 | Ekwuribe |

(Continued)

FOREIGN PATENT DOCUMENTS

| | | |
|---|---|---|
| EP | 0243929 | 11/1987 |
| WO | 2005120573 | 12/2005 |

OTHER PUBLICATIONS

International Search Report and the Written Opinion of the International Searching Authority corresponding to International Patent Application No. PCT/US2017/063251 (11 pages) (dated Apr. 26, 2018).

(Continued)

*Primary Examiner* — Brian E McDowell
(74) *Attorney, Agent, or Firm* — Myers Bigel, P.A.

(57) ABSTRACT

Described herein are bacteriochlorins comprising an annulated isocyclic ring such as a compound Formula I:

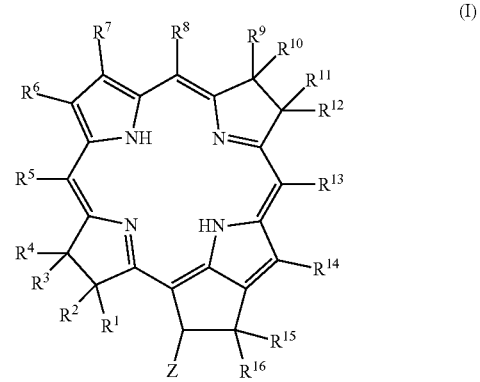

(I)

or a metal conjugate thereof, wherein: $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and Z are each as defined herein. Also described are methods and intermediates for the synthesis of bacteriochlorins comprising an annulated isocyclic ring, and methods of using such bacteriochlorins for, among other things, diagnostic and therapeutic purposes such as, e.g., luminescent compounds in flow cytometry, and/or as active agents in photodynamic therapy (PDT).

12 Claims, No Drawings

(56) References Cited

U.S. PATENT DOCUMENTS

| | | | |
|---|---|---|---|
| 5,709,874 | A | 1/1998 | Hanson et al. |
| 5,759,542 | A | 6/1998 | Gurewich |
| 5,840,674 | A | 11/1998 | Yatvin et al. |
| 5,860,957 | A | 1/1999 | Jacobsen et al. |
| 5,900,252 | A | 5/1999 | Calanchi et al. |
| 5,915,925 | A | 6/1999 | North, Jr. |
| 5,948,433 | A | 9/1999 | Burton et al. |
| 5,952,366 | A | 9/1999 | Pandey et al. |
| 5,972,366 | A | 10/1999 | Haynes et al. |
| 5,983,134 | A | 11/1999 | Ostrow |
| 5,985,307 | A | 11/1999 | Hanson et al. |
| 5,985,317 | A | 11/1999 | Venkateshwaran et al. |
| 6,004,534 | A | 12/1999 | Langer et al. |
| 6,010,715 | A | 1/2000 | Wick et al. |
| 6,024,975 | A | 2/2000 | D'Angelo et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,208,553 | B1 | 3/2001 | Gryko et al. |
| 6,212,093 | B1 | 4/2001 | Lindsey |
| 6,248,590 | B1 | 6/2001 | Malachowski |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,273,904 | B1 | 8/2001 | Chen et al. |
| 6,274,552 | B1 | 8/2001 | Tamarkin et al. |
| 6,316,652 | B1 | 11/2001 | Steliou |
| 6,324,091 | B1 | 11/2001 | Gryko et al. |
| 6,381,169 | B1 | 4/2002 | Bocian et al. |
| 6,407,330 | B1 | 6/2002 | Lindsey et al. |
| 6,420,648 | B1 | 7/2002 | Lindsey |
| 6,451,942 | B1 | 9/2002 | Li et al. |
| 6,524,570 | B1 | 2/2003 | Glue et al. |
| 6,589,792 | B1 | 7/2003 | Malachowski |
| 6,656,906 | B1 | 12/2003 | Barney et al. |
| 6,657,884 | B2 | 12/2003 | Bocian et al. |
| 6,706,963 | B2 | 3/2004 | Gaudiana et al. |
| 6,716,811 | B1 | 4/2004 | Cwirla et al. |
| 6,720,306 | B2 | 4/2004 | Greenwald et al. |
| 6,728,129 | B2 | 4/2004 | Lindsey et al. |
| 6,858,158 | B2 | 2/2005 | Chittibabu et al. |
| 6,890,487 | B1 | 5/2005 | Sklar et al. |
| 6,900,382 | B2 | 5/2005 | Chittibabu et al. |
| 6,913,713 | B2 | 7/2005 | Chittibabu et al. |
| 6,924,427 | B2 | 8/2005 | Eckert et al. |
| 6,933,436 | B2 | 8/2005 | Shaheen et al. |
| 7,501,507 | B2 | 3/2009 | Balakumar et al. |
| 8,530,459 | B2 | 9/2013 | Borbas et al. |
| 8,664,260 | B2 | 3/2014 | Kim et al. |
| 2004/0044197 | A1 | 3/2004 | Pandey et al. |
| 2005/0096465 | A1 | 5/2005 | Lindsey et al. |
| 2006/0194960 | A1 | 8/2006 | Kim et al. |

OTHER PUBLICATIONS

Kanumuri et al. "Synthetic bacteriochlorins with integral spiropiperidine motifs" New Journal of Chemistry, 37:1157-1173 (2013).
Aburatani et al. "Hafnium Chloride Catalyzed Conjugate Addition of Pyrrole, Pyrazole and Imidazole to alpha,beta-Unsaturated Ketones" Heterocycles, 71:189-196 (2007).
Alazard et al. "Composés interagissant avec in tubuline. Partie II, synthése de lactames tricycliques à squelette phénylpyrrole, analogues structuraux du rhazinilame" Bull. Soc. Chim Fr, 133:251-266 (1996) (English translation of abstract).
Aravindu et al. "Facile synthesis of a B,D-tetradehydrocorrin and rearrangement to bacteriochlorins" New Journal of Chemistry, 35(7):1376-1384 (2011).
Azizi et al. "Efficient Friedel-Crafts alkylation of indoles and pyrrole with enones and nitroalkene in water" Organic & Biomolecular Chemistry, 4:4275-4277 (2006).
Baburajan et al. "One pot direct synthesis of ß-ketoesters via carbonylation of aryl halides using cobalt carbonyl" Tetrahedron Letters, 55(25):3525-3528 (2014).
Brennan et al. "Preparation of Bispecific Antibodies by Chemical Recombination of Monoclonal Immunoglobulin G1 Fragments" Science, 229(4708):81-83 (1985).
Cheng et al. "Synthesis and michael reaction of 3,4-dimethylpyrrole" Journal of Heterocyclic Chemistry, 13(5):1145-1147 (1976).
Cox et al. "Formation of the isocyclic ring in chlorophyll" Journal of the American Chemical Society, 91(5):1232-1233 (1969).
Cox et al. "Pyrroles and related compounds. 28. Beta-keto-esters in the porphyrin series" Journal of the Chemical Society, Perkin Transactions 1, pp. 512-516 (1974).
Das et al. "Iodine-catalyzed efficient conjugate addition of pyrroles to alpha,beta-unsaturated ketones" Tetrahedron Letters, 48(16):2867-2870 (2007).
De La Hoz et al. "Preparation of alpha- and beta-substituted alanine derivatives by alpha-amidoalkylation or Michael addition reactions under heterogeneous catalysis assisted by microwave irradiation" Tetrahedron, 57(25):5421-5428 (2001).
Deans et al. "Serendipitous synthetic entree to tetradehydro analogues of cobalamins" New Journal of Chemistry, 37:3964-3975 (2013).
Deng et al. "An Efficient Convergent Synthesis of Novel Anisotropic Adsorbates Based on Nanometer-Sized and Tripod-Shaped Oligophenylenes End-Capped with Triallylsilyl Groups" The Journal of Organic Chemistry, 67 (15):5279-5283 (2002).
Dissous et al. "Schistosoma Mansoni Surface Antigen Defined by a Rat Monoclonal IgG2a" The Journal of Immunology, 129(5):2232-2234 (1982).
Evans et al. "Catalytic Enantioselective Pyrrole Alkylations of alpha,beta-Unsaturated 2-Acyl Imidazoles" Organic Letters, 8(11):2249-2252 (2006).
Fan et al. "Regioselective 15-Bromination and Functionalization of a Stable Synthetic Bacteriochlorin" The Journal of Organic Chemistry, 72(14):5350-5357 (2007).
Firouzabadi et al. "The facile and efficient Michael addition of indoles and pyrrole to alpha,beta-unsaturated electron-deficient compounds catalyzed by aluminium dodecyl sulfate trihydrate [Al(DS)3].3H2O in water" Chemical Communications, 6:789-791 (2005).
Flaugh et al. "Synthesis of porphyrins. Deoxophylloerythroetioporphyrin" Journal of the American Chemical Society, 90(24):6877-6879 (1968).
Fox et al. "Fluorescence and Redox Activity of Probes Anchored through an Aminotrithiol to Polycrystalline Gold" Langmuir, 14(4):816-820 (1998).
Fujiwara et al. "Iron(III) Salt-Catalyzed Nazarov Cyclization/Michael Addition of Pyrrole Derivatives" Advanced Synthesis & Catalysis, 351(1-2):123-128 (2009).
Galoppini et al. "Long-Distance Electron Transfer Across Molecule-Nanocrystalline Semiconductor Interfaces" Journal of the American Chemical Society, 123(18):4342-4343 (2001).
Galoppini et al. "Long-Range Electron Transfer across Molecule-Nanocrystalline Semiconductor Interfaces Using Tripodal Sensitizers" Journal of the American Chemical Society, 124(26):7801-7811 (2002).
Gilmore et al. "The Baldwin rules: revised and extended" WIREs Computational Molecular Science, 6(5):487-514 (2016).
Glennie et al. "Preparation and performance of bispecific F(ab' gamma)2 antibody containing thioether-linked Fab' gamma fragments" The Journal of Immunology, 139:2367-2375 (1987).
Grzych et al. "In vitro and in vivo effector function of rat IgG2a monoclonal anti-S. mansoni antibodies" The Journal of Immunology, 129:2739-2743 (1982).
Gurdere et al. "Aluminum chloride—catalyzed C-alkylation of pyrrole and indole with chalcone and bis-chalcone derivatives" Synthetic Communications, 46(4):322-331 (2016).

(56) References Cited

OTHER PUBLICATIONS

Hack et al. "Asymmetric Organocatalytic Michael Addition of Pyrroles to Enones by Cinchona Alkaloid-Derived Primary Amines" Synthesis, 45(20:2904-2912 (2013).

Hayakawa et al. "Novel bicycloannulation via tandem vinylation and intramolecular Diels-Alder reaction of five-membered heterocycles: a new approach to construction of psoralen and azapsoralen" Journal of the American Chemical Society, 106(22):6735-6740 (1984).

Hector et al. "Investigation of vinyl phosphonic acid/hydroxylated alpha-A12O3(0001) reaction enthalpies" Surface Science, 494:1-20 (2001).

Hong et al. "Direct alkylation of pyrrole with vinyl substituted aromatics: versatile precursors for the synthesis of porphyrinoid macrocycles" Tetrahedron Letters, 49(26):4138-4141 (2008).

Hortensteiner et al. "Chlorophyll breakdown in higher plants" Biochimica et Biophysica Acta (BBA)—Bioenergetics, 1807(8):977-988 (2011).

Hu et al. "Ferrocenyl derivatives with one, two, or three sulfur-containing arms for self-assembled monolayer formation" The Journal of Organic Chemistry, 65(8):2277-2281 (2000).

Hua et al. "Enantioselective Friedel-Crafts Alkylation of Pyrrole with Chalcones Catalyzed by a Dinuclear Zinc Catalyst" The Journal of Organic Chemistry, 79(23):11690-11699 (2014).

Huang et al. "Enantioselective Friedel-Crafts Reaction of beta-Trifluoromethylated Acrylates with Pyrroles and Its Application to the Synthesis of Trifluorinated Heliotridane" Organic Letters, 12(5):1136-1138 (2010).

International Preliminary Report on Patentability corresponding to International Patent Application No. PCT/US2017/063251 (8 pages) (dated Jun. 13, 2019).

Karpovsky et al. "Production of target-specific effector cells using hetero-cross-linked aggregates containing anti-target cell and anti-Fc gamma receptor antibodies" Journal of Experimental Medicine, 160:1686-1701 (1984).

Kasper et al. "Isolation and characterization of a monoclonal antibody-resistant antigenic mutant of Toxoplasma gondii" The Journal of Immunology, 129:1694-1699 (1982).

Kawatsura et al. "Iron Salt-cataltzed Multipoint Alkylation of Pyrrole with Vinyl Ketones" Chemistry Letters, 37(7):794-795 (2008).

Kenner et al. "Porphyrin beta-keto-esters and their cyclisation to phaeoporphyrins" Journal of the Chemical Society, Chemical Communications, 14:844-845 (1972).

Kenner et al. "Pyrroles and related compounds. Part XXX. Cyclisation of porphyrin ß-keto-esters to phaeoporphyrins" Journal of the Chemical Society, Perkin Transactions 1, pp. 527-530 (1974).

Khoury et al. "Syntheses, characterization, and structural chemistry of biladien-ac-10-one and -bc-5-one metal complexes with 4N or (3N + O) co-ordination" Journal of the Chemical Society, Dalton Transactions, 20:3937-3950 (1996).

Kim et al. "De Novo Synthesis of Stable Tetrahydroporphyrinic Macrocycles: Bacteriochlorins and a Tetradehydrocorrin" The Journal of Organic Chemistry, 70:5475-5486 (2005).

Kitanosono et al. "The combined use of cationic palladium(II) with a surfactant for the C—H functionalization of indoles and pyrroles in water" Tetrahedron, 71(40):7739-7744 (2015).

Kobayashi et al. "Spectroscopy and Structure Determination" Chlorophylls and Bacteriochlorophylls, Chapter 6, pp. 79-94 (2006).

Kowalik et al. "New alternating conductive heteropolymers" Synthetic Metals,41(1-2):435-438 (1991).

Kozyrev et al. "Characterization of Porphyrins, Chlorins, and Bacteriochlorins Formed via Allomerization of Bacteriochlorophyll a. Synthesis of Highly Stable Bacteriopurpurinimides and Their Metal Complexes" The Journal of Organic Chemistry, 71(5):1949-1960 (2006).

Krautler, Bernhard "Phyllobilins—the abundant bilin-type tetrapyrrolic catabolites of the green plant pigment chlorophyll" Chemical Society Reviews, 43:6227-6238 (2014).

Krautler, Bernhard "Breakdown of Chlorophyll in Higher Plants—Phyllobilins as Abundant, Yet Hardly Visible Signs of Ripening, Senescence, and Cell Death" Angewandte Chemie International Edition, 55:4882-4907 (2016).

Krayer et al. "Refined synthesis of hydrodipyrrin precursors to chlorin and bacteriochlorin building blocks" Journal of Porphyrins and Phthalocyanines, 13:1098-1110 (2009).

Krayer et al. "Expanded Scope of Synthetic Bacteriochlorins via Improved Acid Catalysis Conditions and Diverse Dihydrodipyrrin-Acetals" The Journal of Organic Chemistry, 75(4):1016-1039 (2010).

Krayer et al. "De novo synthesis and photophysical characterization of annulated bacteriochlorins. Mimicking and extending the properties of bacteriochlorophylls" New Journal of Chemistry, 35:587-601 (2011).

Kusurkar et al. "Conjugate addition of Pyrroles to alpha, beta—unsaturated ketones using copper bromide as a catalyst" Tetrahedron Letters, 47(41):7323-7326 (2006).

Laha et al. "A New Route for Installing the Isocyclic Ring on Chlorins Yielding 131-Oxophorbines" The Journal of Organic Chemistry, 71:7049-7052 (2006).

Lash et al. "Recent advances in the synthesis of porphyrins with five-membered exocyclic rings" Energy & Fuels, 7(2):172-178 (1993).

Lee et al. "Cinchona-based primary amine-catalyzed enantioselective aza-Michael reactions of pyrroles with alpha, beta-unsaturated aldehydes" Tetrahedron: Asymmetry, 25(20-21):1383-1388 (2014).

Lindsey, Jonathan S. "De Novo Synthesis of Gem-Dialkyl Chlorophyll Analogues for Probing and Emulating Our Green World" Chemical Reviews, 115(13):6534-6620 (2015).

Liu et al. "Heteroantibody duplexes target cells for lysis by cytotoxic T lymphocytes" Proceedings of the National Academy of Sciences USA, 82:8648-8652 (1985).

Liu et al. "Northern-Southern Route to Synthetic Bacteriochlorins" The Journal of Organic Chemistry, 81 (23):11882-11897 (2016).

Luond et al. "Michael Reactions of alpha-Unsubstituted Trisubstituted 1H-Pyrroles" Helvetica Chimica Acta, 74(1):91-102 (1991).

Malona et al. "A General Method for the Catalytic Nazarov Cyclization of Heteroaromatic Compounds" Organic Letters, 8(24):5661-5664 (2006).

Mass et al. "A trans-AB-Bacteriochlorin Building Block" The Journal of Organic Chemistry, 76(22):9478-9487 (2011).

Mass et al. "Structural characteristics that make chlorophylls green: interplay of hydrocarbon skeleton and substituents" New Journal of Chemistry, 35:76-88 (2011).

Mazaki et al. "Epimerization of Chlorophyll Derivatives. V. Effects of the Central Magnesium and Ring Substituents on the Epimerization of Chlorophyll Derivatives" Bulletin of the Chemical Society of Japan, 65(11):3080-3087 (1992).

Merrifield et al. "Design and synthesis of antimicrobial peptides" Ciba Foundation Symposium, 186:5-20 (1994).

Meyer et al. "Probing native-like orientation of pigments in modified reaction centers from Rhodobacter sphaeroides R26 by linear dichroism" FEBS Letters, 393:131-134 (1996).

Milstein et al. "Hybrid hybridomas and the production of bi-specific monoclonal antibodies" Immunology Today, 5(10):299-304 (1984).

Minehan et al. "Extension of the Eschenmoser sulfide contraction/iminoester cyclization method to the synthesis of tolyporphin chromophore" Tetrahedron Letters, 38(39):6811-6814 (1997).

Minehan et al. "Total Synthesis of the Proposed Structure of (+)-Tolyporphin A O,O-Diacetate" Angewandte Chemie International Edition, 38(7):923-925 (1999).

Moss, G. P. "Nomenclature of Tetrapyrroles" Pure & Applied Chemistry, 59(6):779-832 (1987).

Muthiah et al. "Regioselective Bromination Tactics in the de Novo Synthesis of Chlorophyll b Analogues" The Journal of Organic Chemistry, 74(9):3237-3247 (2009).

Nikitin et al. "Synthesis of tripodal [2]rotaxanes: high concentration principle" Chemical Communications, 2:282-283 (2003).

Ogoshi et al. "1,1,1-Trifluoro-2-penten-4-one as a building block of trifluoromethyl-substituted compounds" The Journal of Organic Chemistry, 51(12):2366-2368 (1986).

(56) References Cited

OTHER PUBLICATIONS

Paajanen et al. "Proton relaxation enhancement of albumin, immunoglobulin G, and fibrinogen labeled with Gd-DTPA" Magnetic Resonance in Medicine, 13(1):38-43 (1990).
Paras et al. "New Strategies in Organic Catalysis:? The First Enantioselective Organocatalytic Friedel-Crafts Alkylation" Journal of the American Chemical Society, 123(18):4370-4371 (2001).
Polin, R. A. "Monoclonal Antibodies Against Microorganisms" European Journal of Clinical Microbiology & Infectious Diseases, 3(5):387-398 (1984).
Pykett, Ian L. "NMR Imaging in Medicine" Scientific American, 246(5):78-91 (1982).
Rakestraw et al. "Antibody-targeted photolysis: In vitro studies with Sn(IV) chlorin e6 covalently bound to monoclonal antibodies using a modified dextran carrier" Proceedings of the National Academy of Sciences USA, 87:4217-4221 (1990).
Runge et al. "Paramagnetic Agents for Contrast-Enhanced NMR Imaging: A Review" American Journal of Roentgenology, 141(6):1209-1215 (1983).
Saracoglu, Nurullah "Functionalization of Indole and Pyrrole Cores via Michael-Type Additions" Topics in Heterocyclic Chemistry: Bioactive Heterocycles V, 11:1-61 (2007).
Scheer, Hugo "An Overview of Chlorophylls and Bacteriochlorophylls: Biochemistry, Biophysics, Functions and Applications" Chlorophylls and Bacteriochlorophylls, Chapter 1, pp. 1-26 (2006).
Senge et al. "Chlorophylls, Symmetry, Chirality, and Photosynthesis" Symmetry, 6:781-843 (2014).
Sibi et al. "Enantioselective Enolate Protonations: Friedel-Crafts Reactions with alpha-Substituted Acrylates" Angewandte Chemie International Edition, 47(51):9913-9915 (2008).
Siiman et al. "Tris(3-mercaptopropyl-N-glycylmainomethane as a new linker to bridge antibody with metal particles for biological cell separations" Bioconjugate Chemistry, 11(4):549-556 (2000).
Simpson et al. "Isolation and partial characterization of the tegumental outer membrane of adult Schistosoma mansoni" Parasitology, 83(1):163-177 (1981) (Abstract only).
Smith et al. "Partial synthesis of chlorophyll-a from rhodochlorin" Tetrahedron, 37(Suppl. 1):399-403 (1981).
Smith et al. "Passive immunization of mice against Schistosoma mansoni with an IgM monoclonal antibody" Parasitology, 84(1):83-91 (1982) (Abstract only).
Song et al. "The First Examples of Nazarov Cyclizations Leading to Annulated Pyrroles" Organic Letters, 8(1):163-166 (2006).
Tamiaki et al. "Asymmetric synthesis of methyl bacteriopheophorbide-d and analogues by stereoselective reduction of the 3-acetyl to the 3-(1-hydroxyethyl) group" Tetrahedron: Asymmetry, 9(12):2101-2111 (1998).
Treibs et al. "Reaktionen von Pyrrolen mit alpha,beta-ungesättigten Aldehyden and Ketonen" Justus Liebigs Annalen der Chemie, pp. 849-857 (1981) (English translation of abstract).
Umemura et al. "Recent advances in sonodynamic approach to cancer therapy" Ultrasonics Sonochemistry, 3(3):S187-S191 (1996).
Unaleroglu et al. "Metal Triflates-Catalyzed Conjugate Addition of Homochiral Pyrroles to alpha,beta-Unsaturated Esters" Synthesis, 15:2574-2578 (2004).
Unaleroglu et al. "Gadolinium triflate catalyzed alkylation of pyrroles: efficient synthesis of 3-oxo-2,3-dihydro-1H-pyrrolizine derivatives" Tetrahedron, 63(25):5608-5613 (2007).
Unaleroglu et al. "An Efficient Synthetic Route for Pyrrolizinone Synthesis through Functionalized C-Alkylpyrroles" Synthesis, 19:3243-3250 (2009).
Vaidya et al. "A Highly Reactive Dicationic Iridium(III) Catalyst for Polarized Nazarov Cyclization" Angewandte Chemie International Edition, 49(19):3363-3366 (2010).
Van Der Rest et al. "The Pigment Complement of the Photosynthetic Reaction Center Isolated from Rhodospirillum rubrum" The Journal of Biological Chemistry, 249(20):6446-6453 (1974).
Wang et al. "Synthesis and Structure of Tolyporphin A O,O-Diacetate" Organic Letters, 1(7):1129-1132 (1999).
Wang et al. "Tandem reactions of Friedel-Crafts/aldehyde cyclotrimerization catalyzed by an organotungsten Lewis acid" Tetrahedron Letters, 43:1051-1055 (2002).
Wang et al. "Highly Enantioselective Synthesis of beta-Heteroaryl-Substituted Dihydrochalcones Through Friedel-Crafts Alkylation of Indoles and Pyrrole" Chemistry A European Journal, 16(5):1664-1669 (2010).
Webb et al. "Addition of Heterocycles to Conjugate Unsaturated Carbonyl Compounds: Difunctional Derivatives" Journal of the American Chemical Society, 73(2):752-753 (1951).
Wenz et al. "The Nazarov Cyclization: A Valuable Method to Synthesize Fully Substituted Carbon Stereocenters" European Journal of Organic Chemistry, 2015(1):23-37 (2015).
Whitesell et al. "Directionally Aligned Helical Peptides on Surfaces" Science, 261:73-76 (1993).
Woodward et al. "The Total Synthesis of Chlorophyll" Journal of the American Chemical Society, 82(14):3800-3802 (1960).
Woodward, R. B. "The Total Synthesis of Chlorophyll" Pure and Applied Chemistry, 2:383-404 (1961).
Woodward et al. "The total synthesis of chlorophyll a" Tetrahedron, 46(22):7599-7659 (1990).
Yadav et al. "Addition of pyrroles to electron deficient olefins employing InCl3" Tetrahedron Letters, 42(45):8063-8065 (2001).
Yang et al. "Photophysical Properties and Electronic Structure of Stable, Tunable Synthetic Bacteriochlorins: Extending the Features of Native Photosynthetic Pigments" The Journal of Physical Chemistry B, 115 (37):10801-10816 (2011).
Yao et al. "Facile Convergent Route to Molecular Caltrops" The Journal of Organic Chemistry, 64(6):1968-1971 (1999).
Yoshida et al. "Hybridoma Produces Protective Antibodies Directed against the Sporozoite Stage of Malaria Parasite" Science, 207(4426):71-73 (1980).
Yu et al. "Multifunctional Bacteriochlorins from Selective Palladium-Coupling Reactions" Organic Letters, 14(14):3708-3711 (2012).
Yumita et al. "The Combination Treatment of Ultrasound and Antitumor Drugs on Yoshida Sarcoma" Japanese Journal of Hyperthermic Oncology, 3(2):175-182 (1987).
Yumita et al. "Sonodynamically induced antitumor effect of gallium-porphyrin complex by focused ultrasound on experimental kidney tumor" Cancer Letters, 112:79-86 (1997.
Zhan et al. "Microwave-Assisted Addition of Pyrroles to Electron-Deficient Olefins: A Rapid Entry to C-Alkyl Pyrroles" Synlett, 16:2524-2528 (2005).
Zhan et al. "Bismuth Trichloride-Catalyzed C-Alkylation of Pyrroles with Electron-Deficient Olefins" Synthetic Communications, 36(10):1373-1382 (2006).
Zhang et al. "Selective Michael addition of pyrrole to conjugated alkenes catalyzed by Cr3+-Catsan and ZnCl2" Catalysis Communications, 7(8):534-537 (2006).
Zhang et al. "Synthesis and photophysical characteristics of 2,3,12,13-tetraalkylbacteriochlorins" New Journal of Chemistry, 40:5942-5956 (2016).
Zodda et al. "Monoclonal antibody-mediated protection against Schistosoma mansoni infection in mice" The Journal of Immunology, 129:2326-2328 (1982).

METHODS FOR MAKING BACTERIOCHLORIN MACROCYCLES COMPRISING AN ANNULATED ISOCYCLIC RING AND RELATED COMPOUNDS

RELATED APPLICATION INFORMATION

This application claims the benefit of U.S. Provisional Patent Application Ser. No. 62/428,364, filed Nov. 30, 2016, the disclosure of which is incorporated herein by reference in its entirety.

STATEMENT OF GOVERNMENT SUPPORT

This invention was made with government support under grant number DE-FG12-05ER15661 awarded by the U.S. Department of Energy. The government has certain rights in this invention.

FIELD

The present invention relates generally to bacteriochlorins comprising an annulated isocyclic ring, methods and intermediates for the synthesis of such bacteriochlorins, and methods of using such bacteriochlorins for, among other things, diagnostic and/or therapeutic purposes such as, e.g., luminescent compounds in flow cytometry, and/or as active agents in photodynamic therapy (PDT).

BACKGROUND

Bacteriochlorins exhibit strong absorption in the near infrared (NIR) spectral region. The core chromophore of bacteriochlorophylls a, b and g, the chief light-harvesting pigments in anoxygenic photosynthetic bacteria, is a bacteriochlorin (Chart 1). Bacteriochlorins are members of the tetrapyrrole family and contain alternating pyrrole and pyrroline rings. Bacteriochlorophylls also contain a fifth, annulated ring (the "isocyclic' ring, or ring E) that spans positions 13 and 15; the ring is equipped with an integral keto group that lies coplanar with the organic π-system. In addition, an auxochrome is present at the 3-position, distal to the coplanar keto group of the isocyclic ring. Bacteriochlorophyll b differs from bacteriochlorophyll a in the presence of an exocyclic ethylidene group in ring B, whereas bacteriochlorophyll g contains the exocyclic ethylidene group in ring B as well as a 3-vinyl group and geranylgeraniol (or other alcohol) rather than phytol as the esterifying alcohol at the $17^3$-position.

Chart 1. Bacteriochlorophylls and Bacteriochlorin Nomenclature

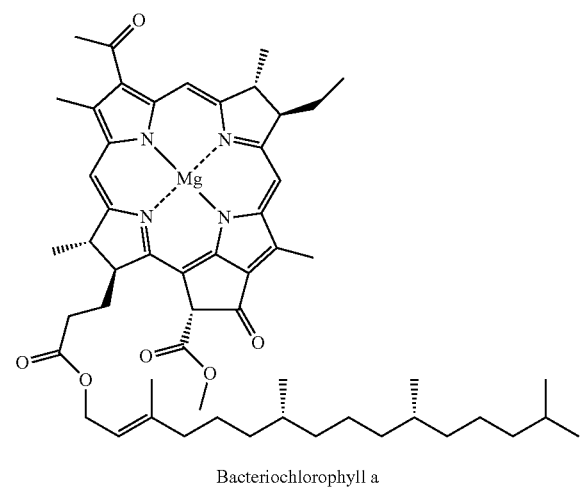

Bacteriochlorophyll a

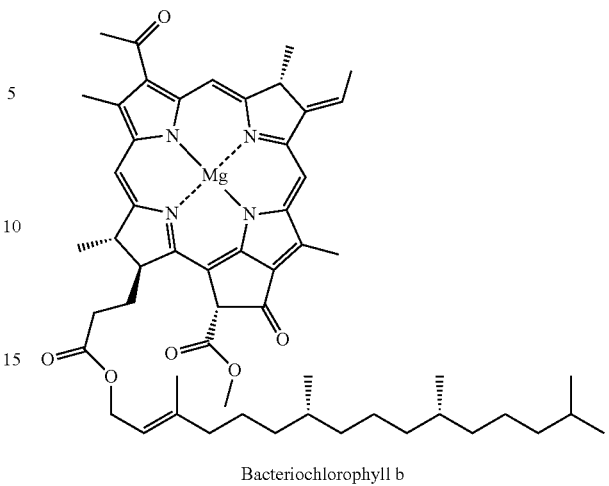

Bacteriochlorophyll b

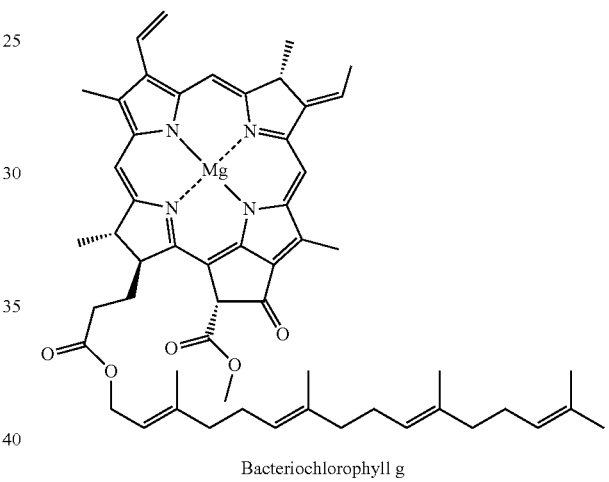

Bacteriochlorophyll g

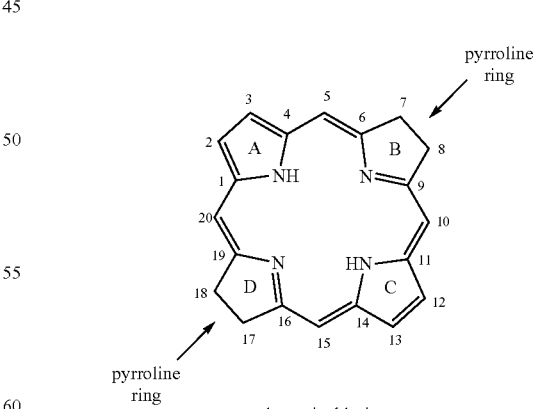

bacteriochlorin

De novo syntheses of bacteriochlorins have been developed, but the routes rely on the self-condensation of a dihydrodipyrrin-acetal (II-acetal) or dihydrodipyrrin-carboxaldehyde (II-CHO) (Scheme 1).

Scheme 1. Self-Condensation of Precursors to Form Bacteriochlorins

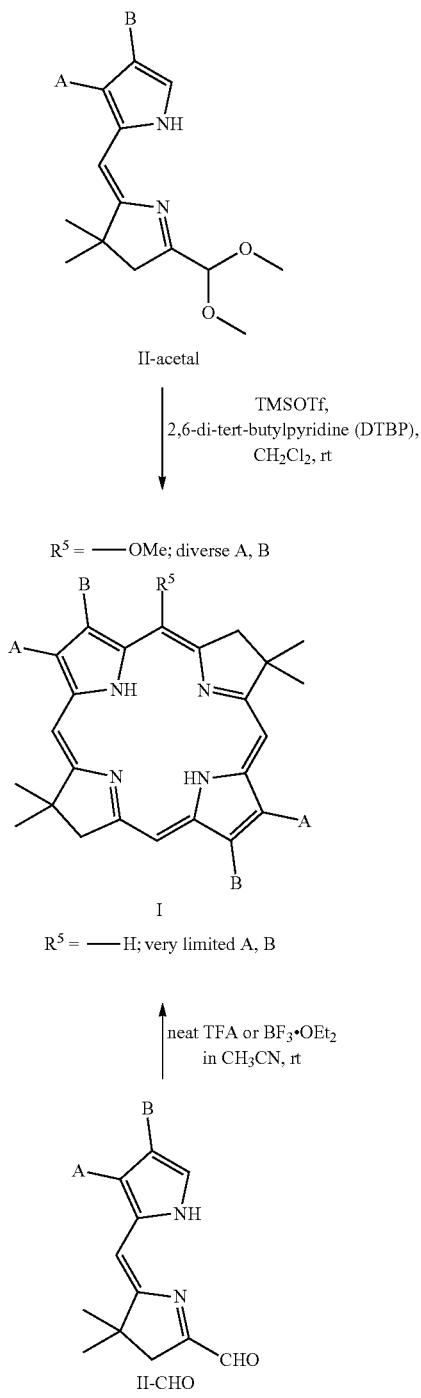

A chief limitation of both de novo syntheses originates with the dimerization process since whatever substituents are present on the pyrrole unit of the dihydrodipyrrin species are conveyed to the two pyrroles of the bacteriochlorin.

SUMMARY OF THE INVENTION

A first aspect of the present invention is a method of making a compound of Formula I:

(I)

[Structure of Formula I shown with substituents $R^1$ through $R^{16}$ and Z on a bacteriochlorin macrocycle]

or a metal conjugate thereof (e.g., a metal chelate thereof), wherein:

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;

or $R^3$ and $R^4$ together are =O or spiroalkyl;

or $R^9$ and $R^{10}$ together are =O or spiroalkyl;

or $R^{11}$ and $R^{12}$ together are =O or spiroalkyl;

or $R^{15}$ and $R^{16}$ together are =O;

or $R^5$ and $R^6$ together represent a fused aromatic or heteroaromatic ring systems;

or $R^6$ and $R^7$ together represent a fused aromatic or heteroaromatic ring systems;

or $R^{13}$ and $R^{14}$ together represent a fused aromatic or heteroaromatic ring systems; and Z is an electron-withdrawing group (e.g., —$CO_2R^{17}$, —C(O)$NHR^{17}$, —C(O)$NR^{17}R^{18}$, —C(O)$R^{17}$, —CN, —C=N—$NR^{17}R^{18}$, —PO(O$R^{17}$)$_2$, —$SO_2OR^{17}$, —$SO_2NR^{17}R^{18}$, —$SO_2R^{17}$, and —$SiR^{17}R^{18}R^{19}$, and wherein $R^{17}$, $R^{18}$, and $R^{19}$ are, in each occurrence, independently selected from the group consisting of hydrogen, alkyl and aryl);

the method comprising condensing a compound of Formula II and a compound of Formula III in a composition comprising a first solvent to produce an intermediate;

wherein the compound of Formula II has a structure represented by:

(II)

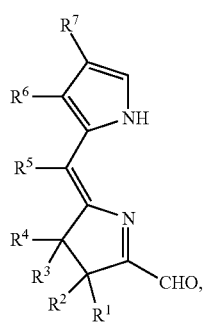

or a metal conjugate thereof (e.g., a metal chelate thereof), wherein:
$R^1$, $R^2$, $R^3$, $R^4$, $R^5$, $R^6$, and $R^7$ are as provided above;
wherein the compound of Formula III has a structure represented by:

(III)

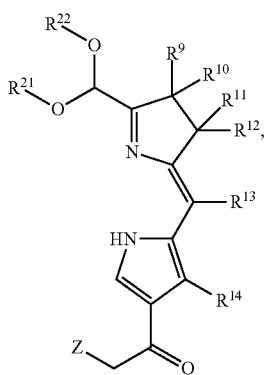

or a metal conjugate thereof (e.g., a metal chelate thereof), wherein:
$R^9$, $R^{10}$, $R^{11}$, $R^{12}$, $R^{13}$, and $R^{14}$ are as provided above; and
$R^{21}$ and $R^{22}$ are each independently selected from the group consisting of hydrogen, alkyl and aryl, or $R^{21}$ and $R^{22}$ taken together represent a C2-C4 alkylene; and
condensing the intermediate in a second solvent in the presence of an acid to produce the compound of Formula I or a metal conjugate thereof.

Further aspects of the present invention include compounds of Formula IA, Formula IB, Formula IC, Formula ID, Formula IE, Formula IF, and Formula IG, compounds of Formula II, Formula IIA, Formula IIB, and Formula IIC, compounds of Formula III, Formula IIIA, and Formula IIIB, compounds of Formula IV and Formula IVA, compounds of Formula V and Formula VA, and compounds of Formula VI and Formula VIA.

Compounds of the present invention (sometimes referred to as "active compounds" herein) include compounds of Formula I, and pharmaceutically acceptable salts, prodrugs and/or conjugates (such as metal chelates) thereof.

Another aspect of the present invention includes a method of detecting particles, such as cells, by flow cytometry, wherein the particles are labelled with a compound of the present invention.

A further aspect of the present invention is, in a method of detecting particles, such as cells, by flow cytometry, wherein the particles are labelled with a detectable luminescent compound, the improvement comprising utilizing a bacteriochlorin as described herein as the luminescent compound.

A further aspect of the present invention is a method for treating a target in a subject in need thereof, comprising: (i) administering to the subject an active compound as described herein or a pharmaceutically acceptable conjugate thereof, optionally wherein the compound associates with the target, and (ii) irradiating the target with light of a wavelength and intensity sufficient to treat the target. Suitable subjects include, but are not limited to, subjects afflicted with opportunistic infections, burns (particularly burns that have become infected), sepsis, ulcers, periodontal disease, atherosclerosis, cosmetic and dermatologic conditions, acne, infectious diseases, tissues that require sealing such as in wounds or surgical incisions, and/or subjects afflicted with neoplastic disease or cancer.

A further aspect of the present invention is a photodynamic therapy method for treating hyperproliferative tissue in a subject in need thereof, comprising: (i) administering to the subject an active compound as described herein or a pharmaceutically acceptable conjugate thereof, optionally wherein the compound associates with the hyperproliferative tissue, and (ii) irradiating a target (e.g., the hyperproliferative tissue) with light of a wavelength and intensity sufficient to activate the compound, and thereby treat the hyperproliferative tissue.

A further aspect of the present invention is a method for detecting the presence of a hyperproliferative tissue in a subject, comprising: (i) administering to the subject an active compound as described herein or a pharmaceutically acceptable conjugate thereof, optionally wherein the compound associates with the hyperproliferative tissue; and then (ii) visualizing the compound within the subject.

Another aspect of the present invention is a method for detecting a tissue in a subject, comprising: (i) administering to the subject a compound as described herein, or a pharmaceutically acceptable conjugate thereof, optionally wherein the compound associates with the tissue; and (ii) detecting the compound within the subject.

A further aspect of the present invention is a kit to treat hyperproliferative disorders, comprising an active compound described herein or a pharmaceutically acceptable conjugate thereof and instructions teaching a method of photodynamic therapy.

A further aspect of the present invention is a kit to label specific tissues for diagnosis comprising an active compound described herein or a pharmaceutically acceptable conjugate thereof and instructions teaching a method of imaging.

The foregoing and other objects and aspects of the invention are explained in greater detail in the drawings herein and the specification set forth below.

DETAILED DESCRIPTION OF THE EXAMPLE EMBODIMENTS

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of 10%, ±5%, ±1%, ±0.5%, or even ±0.1% of X. A range provided herein for a measurable value may include any other range and/or individual value therein.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Hydroxyl" as used herein refers to an —OH group.

"Nitro" as used herein refers to an —NO$_2$ group.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, and, in some embodiments, refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, but are not limited to, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(OXO)OR, where R is any suitable substituent such as alkyl, cycloalkyl, alkenyl, alkynyl or aryl.

"Sulfonic acid as used herein refers to a compound of the formula —S(OXO)OH.

"Amide" as used herein alone or as part of another group refers to a —$C(O)NR_aR_b$ radical, where $R_a$ and $R_b$ are any suitable substituent such as alkyl, cycloalkyl, alkenyl, alkynyl or aryl.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —$N(R_c)C(O)NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —$N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —$OC(O)NR_aR_b$ radical, where $R_a$ and $R_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. In some embodiments, the heterocyclo group includes pyridyl and/or imidazolyl groups, these terms including the quaternized derivatives thereof, including but not limited to quaternary pyridyl and imidazolyl groups, examples of which include but are not limited to:

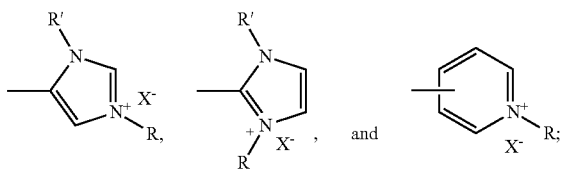

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It may be a polyclonal antibody, and in some embodiments may be an affinity-purified antibody from a human or an appropriate animal, e.g., a primate, goat, rabbit, mouse or the like. Monoclonal antibodies are also suitable for use in the present invention, and may be used because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Infecting agent" as used herein denotes invading microbes or parasites. As used herein, "microbe" denotes virus, bacteria, rickettsia, mycoplasma, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like.

"Tumor" as used herein denotes a neoplasm, and includes both benign and malignant tumors. This term particularly includes malignant tumors which can be either solid (such as a breast, liver, or prostate carcinoma) or non-solid (such as a leukemia). Tumors can also be further divided into subtypes, such as adenocarcinomas (e.g. of the breast, prostate or lung).

"Target" as used herein denotes the object that is intended to be detected, diagnosed, impaired or destroyed by the methods provided herein, and includes target cells, target tissues, and target compositions. "Target tissues" and "target cells" as used herein are those tissues that are intended to be impaired or destroyed by this treatment method. Photosensitizing compounds bind to or collect in these target tissues or target cells; then when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non-target cells.

"Non-target tissues" as used herein are all the tissues of the subject which are not intended to be impaired or destroyed by the treatment method. These non-target tissues include but are not limited to healthy blood cells, and other normal tissue, not otherwise identified to be targeted.

"Target compositions" as used herein are those compositions that are intended to be impaired or destroyed by this treatment method, and may include one or more pathogenic agents, including but not limited to bacteria, viruses, fungi, protozoa, and toxins as well as cells and tissues infected or infiltrated therewith. The term "target compositions" also includes, but is not limited to, infectious organic particles such as prions, toxins, peptides, polymers, and other compounds that may be selectively and specifically identified as an organic target that is intended to be impaired or destroyed by this treatment method.

"Hyperproliferative tissue" as used herein means tissue that grows out of control and includes neoplastic tissue, tumors and unbridled vessel growth such as blood vessel growth found in age-related macular degeneration and often occurring after glaucoma surgeries.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders include, but are not limited to, cancers or carcinomas, acute and membrano-proliferative glomerulonephritis, myelomas, psoriasis, atherosclerosis, psoriatic arthritis, rheumatoid arthritis, diabetic retinopathies, macular degeneration, corneal neovascularization, choroidal hemangioma, recurrence of pterygii, and scarring from excimer laser surgery and glaucoma filtering surgery.

"Therapeutically effective dose" as used herein is a dose sufficient to prevent advancement, or to cause regression of the disease, or which is capable of relieving symptoms caused by the disease.

"Irradiating" and "irradiation" as used herein includes exposing a subject to all wavelengths of light. In some embodiments, the irradiating wavelength is selected to match the wavelength(s) which excite the photosensitive compound. In some embodiments, the radiation wavelength matches the excitation wavelength of the photosensitive compound and has low absorption by the non-target tissues of the subject, including blood proteins.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

Some embodiments of the present invention are drawn to the use of light energy for administering photodynamic therapy (PDT) to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: gallium-porphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

"Coupling agent" as used herein, refers to a reagent capable of coupling a photosensitizer to a targeting agent.

"Targeting group" refers to a compound that homes in on and/or associates and/or binds to a particular tissue, receptor, infecting agent or other area of the body of the subject to be treated, such as a target tissue or target composition, such as described above. Examples of a targeting group or agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (anti-ligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-α and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

"Biological materials" as used herein refers to both tissues (such as biopsy tissues) and cells, as well as biological fluids such as blood, urine, plasma, cerebrospinal fluid, mucus, sputum, etc.

Subjects to be treated by the methods of the present invention for diagnostic and/or therapeutic purposes include both human subjects and animal subjects (particularly mammalian subjects such as, e.g., dogs, cats, horses, monkeys, chimpanzees, etc.) for veterinary purposes.

As noted above, the present invention provides compounds, and methods of making compounds, of Formula I:

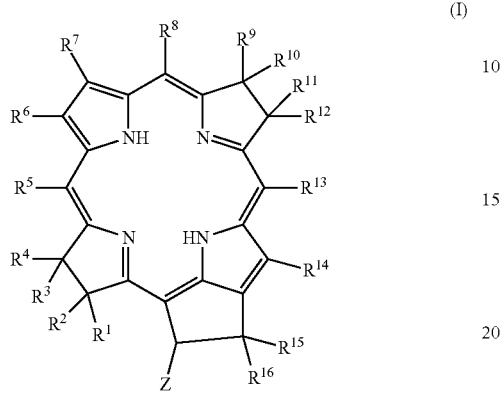

(I)

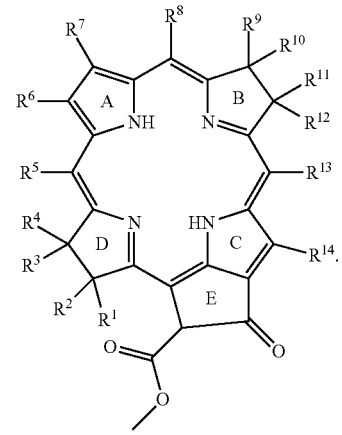

In some embodiments, a compound of Formula I has a structure of Formula IA, Formula IB, Formula IC, Formula ID, Formula IE, Formula IF, or Formula IG:

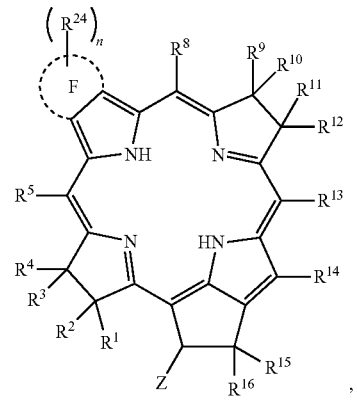

(IA)

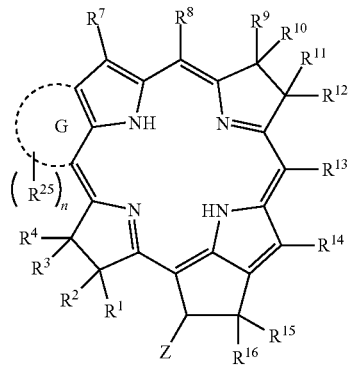

(IB)

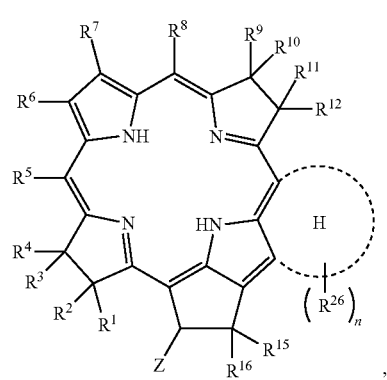

(IC)

or a metal conjugate thereof (e.g., a metal chelate thereof), wherein:

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;

or $R^3$ and $R^4$ together are =O or spiroalkyl;

or $R^9$ and $R^{10}$ together are =O or spiroalkyl;

or $R^{11}$ and $R^{12}$ together are =O or spiroalkyl;

or $R^{15}$ and $R^{16}$ together are =O;

or $R^5$ and $R^6$ together represent a fused aromatic or heteroaromatic ring systems;

or $R^6$ and $R^7$ together represent a fused aromatic or heteroaromatic ring systems;

or $R^{13}$ and $R^{14}$ together represent a fused aromatic or heteroaromatic ring systems; and Z is an electron-withdrawing group (e.g., $-CO_2R^{17}$, $-C(O)NHR^{17}$, $-C(O)NR^{17}R^{18}$, $-C(O)R^{17}$, $-CN$, $-C=N-NR^{17}R^{18}$, $-PO(OR^{17})_2$, $-SO_2OR^{17}$, $-SO_2NR^{17}R^{18}$, $-SO_2R^{17}$, and $-SiR^{17}R^{18}R^{19}$, and wherein $R^{17}$, $R^{18}$, and $R^{19}$ are, in each occurrence, independently selected from the group consisting of hydrogen, alkyl and aryl).

For example, a compound of Formula I may have a structure as follows below in which rings A-D are labeled along with the annulated ring (i.e., the isocyclic ring or ring E):

-continued

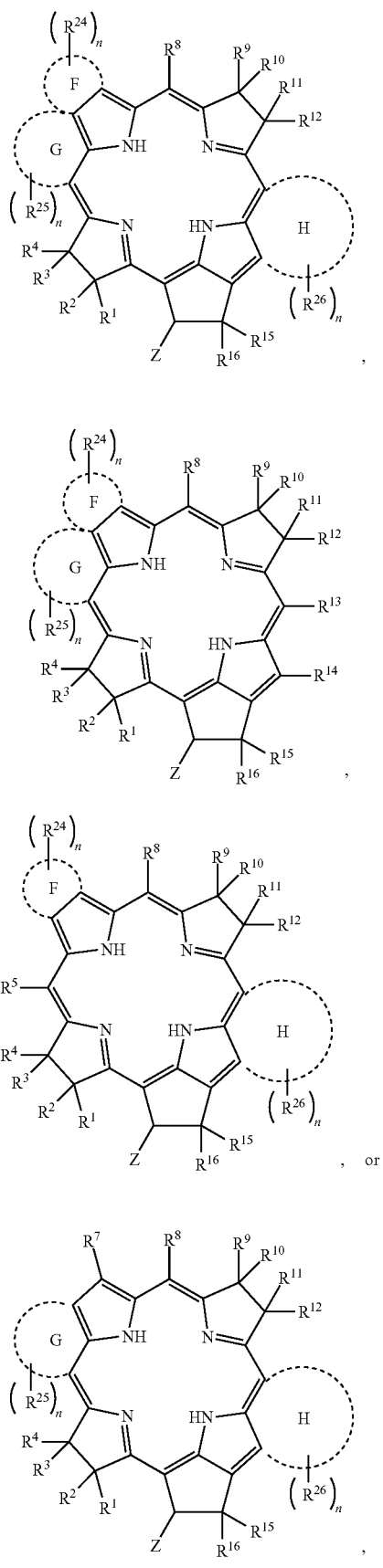

(ID)

(IE)

(IF)

(IG)

or a metal conjugate thereof (e.g., a metal chelate thereof), wherein:

$R^1, R^2, R^3, R^4, R^5, R^6, R^7, R^8, R^9, R^{10}, R^{11}, R^{12}, R^{13}, R^{14}, R^{15}, R^{16}$, and Z are as previously defined for Formula I;

each of rings F, G, and H independently represents a fused aromatic or heteroaromatic ring system (e.g., naphthalene, anthracene, phenanthrene, chrysene, pyrene, corannulene, coronene, hexahelicene, indole, isoindole, indolizine, quinoline, isoquinolene, purine, carbazole, dibenzofuran, 2H-chromene, xanthene, rylene (or poly(peri-naphthalene), e.g., perylene, terrylene, quaterrylene, etc.), each of which may be unsubstituted or substituted with 1, 2 or 3 to 4, 5 or 6 or more independently selected substituents as defined by $R^{24}$, $R^{25}$, and $R^{26}$;

$R^{24}$, $R^{25}$, and $R^{26}$, in each occurrence, is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups; and n is from 1 or 2 to 4, 6 or 8.

In some embodiments, a method of the present invention does not prepare the bacterio-$13^1$-oxophorbine I-e having a structure represented by:

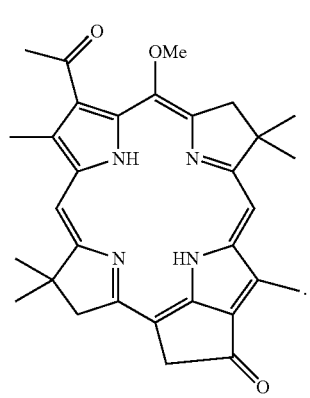

I-e

According to embodiments of the present invention, a method of the present invention comprises condensing a compound of Formula II and a compound of Formula III in a composition comprising a first solvent to produce an intermediate;

wherein the compound of Formula II has a structure represented by:

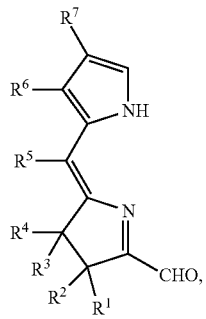

(II)

or a metal conjugate thereof (e.g., a metal chelate thereof), wherein:
$R^1$, $R^2$, $R^3$, $R^4$, $R^5$, $R^6$, and $R^7$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

wherein the compound of Formula III has a structure represented by:

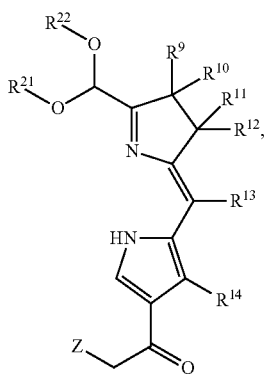

(III)

or a metal conjugate thereof (e.g., a metal chelate thereof), wherein:
$R^9$, $R^{10}$, $R^{11}$, $R^{12}$, $R^{13}$, and $R^{14}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups; and $R^{21}$ and $R^{22}$ are each independently selected from the group consisting of hydrogen, alkyl and aryl, or $R^{21}$ and $R^{22}$ taken together represent a C2-C4 alkylene; and condensing the intermediate in a second solvent in the presence of an acid to produce the compound of Formula I or a metal conjugate thereof (e.g., a metal chelate thereof).

In some embodiments, a method of the present invention produces a compound of Formula I that comprises at least one substituent that is different than another substituent on the compound. In some embodiments, at least one of $R^1$, $R^2$, $R^3$, $R^4$, $R^5$, $R^6$, $R^7$, $R^{24}$, and $R^{25}$ comprises a substituent that is different than $R^9$, $R^{10}$, $R^{11}$, $R^{12}$, $R^{13}$, $R^{14}$, and/or $R^{26}$. In some embodiments, $R^1$ and/or $R^2$ comprise a different substituent than $R^9$ and/or $R^0$, $R^3$ and/or $R^4$ comprise a different substituent than $R^{11}$ and/or $R^{12}$, $R^5$ comprises a different substituent than $R^{13}$, and/or $R^6$ comprises a different substituent than $R^{14}$. In some embodiments, ring A comprises at least one substituent that is different than a substituent on ring C and/or ring D comprises at least one substituent that is different than a substituent on ring B. In some embodiments, ring A comprises at least one substituent that is different than a substituent at the corresponding position on ring C and/or ring D comprises at least one substituent that is different than a substituent at the corresponding position on ring B. In some embodiments, a method of the present invention does not produce a symmetrical bacteriochorin and/or does not produce a compound of Formula I in which the substituents of ring A are symmetrical with the substituents of ring C, excluding ring E (i.e., substituents at sites 13, 14, and 15) and the substituents of ring D are symmetrical with the substituents of ring B.

In some embodiments, a compound of Formula II has a structure represented by Formula IIA, Formula IIB, or Formula IIC:

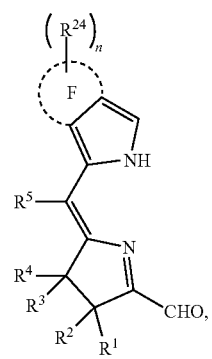

(IIA)

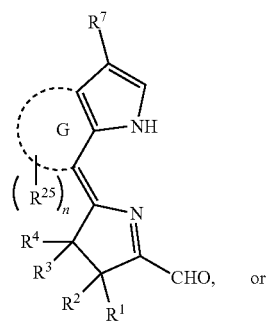

(IIB)

or

-continued

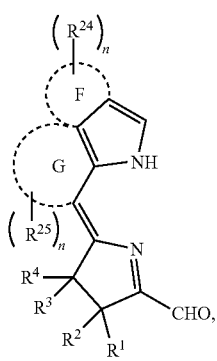

(IIC)

or a metal conjugate thereof (e.g., a metal chelate thereof), wherein:

$R^1$, $R^2$, $R^3$, $R^4$, $R^5$, and $R^7$ are as previously defined for Formula H;

each of rings F and G independently represents a fused aromatic or heteroaromatic ring system (e.g., naphthalene, anthracene, phenanthrene, chrysene, pyrene, corannulene, coronene, hexahelicene, indole, isoindole, indolizine, quinoline, isoquinolene, purine, carbazole, dibenzofuran, 2H-chromene, xanthene, rylene (or poly (peri-naphthalene), e.g., perylene, terrylene, quaterrylene, etc.), each of which may be unsubstituted or substituted with 1, 2 or 3 to 4, 5 or 6 or more independently selected substituents as defined by $R^{24}$ and $R^{25}$; and $R^{24}$ and $R^{25}$, in each occurrence, is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups; and n is from 1 or 2 to 4, 6 or 8.

In some embodiments, $R^1$, $R^2$, $R^3$, and $R^4$ in a compound of Formula H are independently selected from the group consisting of H, alkyl, aryl (e.g., annulated aryl), ester, halo, and cyano.

In some embodiments, a compound of Formula III has a structure represented by Formula IIIA:

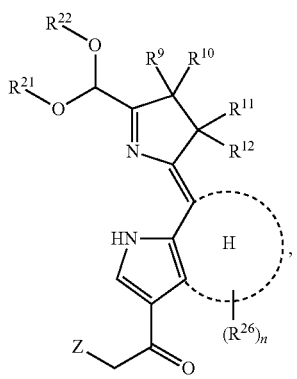

(IIIA)

or a metal conjugate thereof (e.g., a metal chelate thereof), wherein:

$R^9$, $R^{10}$, $R^{11}$, $R^{12}$, $R^{21}$, $R^{22}$, and Z are as previously defined for Formula III; ring H represents a fused aromatic or heteroaromatic ring system (e.g., naphthalene, anthracene, phenanthrene, chrysene, pyrene, corannulene, coronene, hexahelicene, indole, isoindole, indolizine, quinoline, isoquinolene, purine, carbazole, dibenzofuran, 2H-chromene, xanthene, rylene (or poly (peri-naphthalene), e.g., perylene, terrylene, quaterrylene, etc.), each of which may be unsubstituted or substituted with 1, 2 or 3 to 4, 5 or 6 or more independently selected substituents as defined by $R^{26}$; and $R^{26}$, in each occurrence, is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups; and n is from 1 or 2 to 4, 6 or 8.

In some embodiments, a compound of Formula III has a structure represented by Formula IIIB:

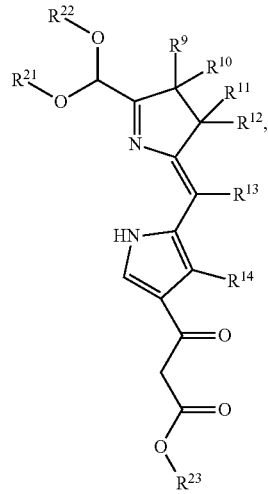

(IIIB)

or a metal conjugate thereof (e.g., a metal chelate thereof), wherein:

$R^9$, $R^{10}$, $R^{11}$, $R^{12}$, $R^{13}$, $R^{14}$, $R^{2l}$, $R^{22}$, and Z are as previously defined for Formula III; and $R^{23}$ is selected from the group consisting of hydrogen, alkyl and aryl.

In some embodiments, a compound of Formula III is prepared from a compound of Formula IV and/or a compound of Formula V. A compound of Formula IV may have a structure represented by:

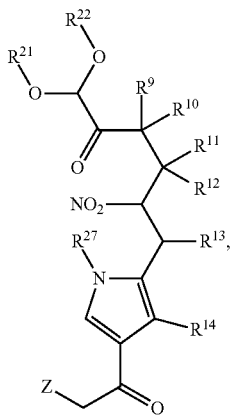
(IV)

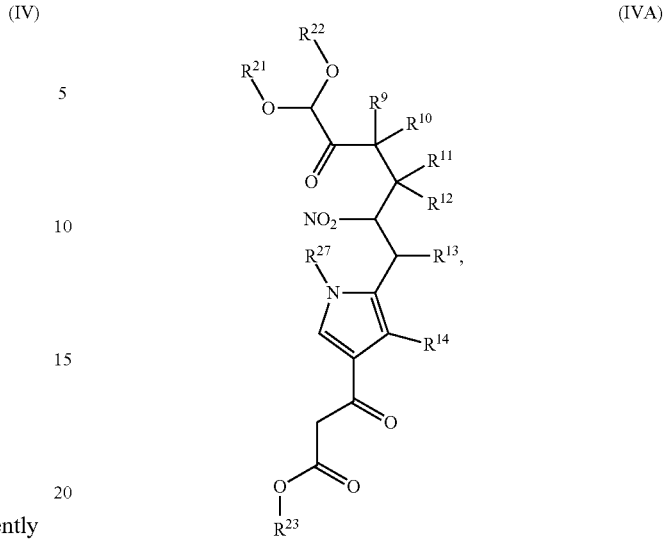
(IVA)

wherein:
$R^9$, $R^{10}$, $R^{11}$, $R^{12}$, $R^{13}$, and $R^{14}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^9$ and $R^{10}$ together are =O or spiroalkyl;

or $R^{11}$ and $R^{12}$ together are =O or spiroalkyl;

or $R^{13}$ and $R^{14}$ together represent a fused aromatic or heteroaromatic ring systems;

$R^{21}$ and $R^{22}$ are each independently selected from the group consisting of hydrogen, alkyl and aryl, or $R^{21}$ and $R^{22}$ taken together represent a C2-C4 alkylene;

$R^{27}$ is a nitrogen protecting group; and

Z is an electron-withdrawing group (e.g., —$CO_2R^{17}$, —$C(O)NHR^{17}$, —$C(O)NR^{17}R^{18}$, —$C(O)R^{17}$, —CN, —C=N—$NR^{17}R^{18}$, —$PO(OR^{17})_2$, —$SO_2OR^{17}$, —$SO_2NR^{17}R^{18}$, —$SO_2R^{17}$, and —$SiR^{17}R^{18}R^{19}$, and where $R^{17}$, $R^{18}$, and $R^{19}$ are, in each occurrence, independently selected from the group consisting of hydrogen, alkyl and aryl).

Example nitrogen protecting groups include, but are not limited to, carbamates (e.g., methyl, ethyl and substituted ethyl carbamates such as trichloroethyl chloroformate (Troc), carboxybenzyl (Cbz), tert-butyloxycarbonyl (Boc), fluorenylmethyloxycarbonyl (Fmoc), trimethylsilyl-ethoxy-carbonyl, cyanoethoxycarbonyl, and allyloxycarbonyl), amides, cyclic imide derivatives, N-alkyl and N-aryl amines, imine derivatives, enamine derivatives, trimethylsilyl (TMS), triisopropylsilyl (TIPS), and/or tosyl.

In some embodiments, a compound of Formula IVA has a structure represented by:

wherein:
$R^9$, $R^{10}$, $R^{11}$, $R^{12}$, $R^{13}$, $R^{14}$, $R^{21}$, $R^{22}$, and $R^{27}$ are as previously defined for Formula IV; and $R^{23}$ is selected from the group consisting of hydrogen, alkyl and aryl.

A compound of Formula V may have a structure represented by:

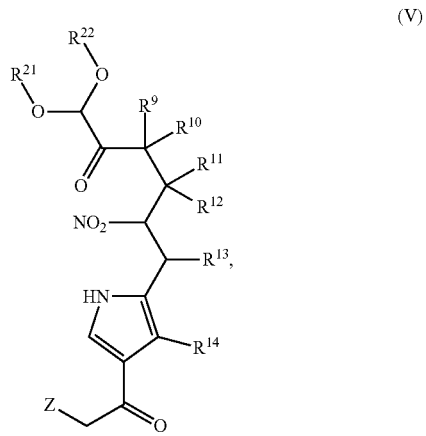
(V)

wherein:
$R^9$, $R^{10}$, $R^{11}$, $R^{12}$, $R^{13}$, and $R^{14}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^9$ and $R^{10}$ together are =O or spiroalkyl;

or $R^{11}$ and $R^{12}$ together are =O or spiroalkyl;

or $R^{13}$ and $R^{14}$ together represent a fused aromatic or heteroaromatic ring systems;

$R^{21}$ and $R^{22}$ are independently selected from the group consisting of hydrogen, alkyl and aryl, or $R^{21}$ and $R^{22}$ taken together represent a C2-C4 alkylene; and Z is an electron-withdrawing (e.g., —$CO_2R^{17}$, —C(O)$NHR^{17}$, —C(O)$NR^{17}R^{18}$, —C(O)$R^{17}$, —CN, —C=N—$NR^{17}R^{18}$, —PO(O$R^{17}$)$_2$, —$SO_2OR^{17}$, —$SO_2NR^{17}R^{18}$, —$SO_2R^{17}$, and —Si$R^{17}R^{18}R^{19}$, and where $R^{17}$, $R^{18}$, and $R^{19}$ are, in each occurrence, independently selected from the group consisting of hydrogen, alkyl and aryl).

In some embodiments, a compound of Formula V has a structure represented by Formula VA:

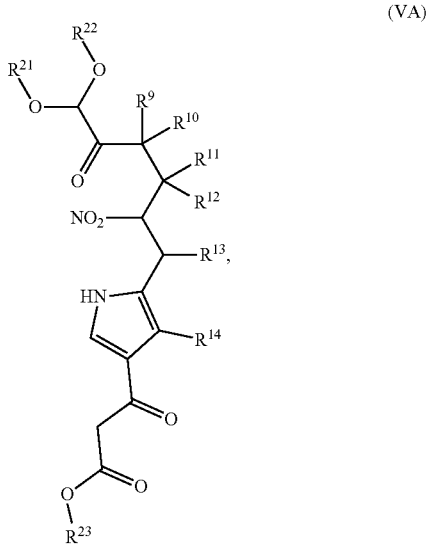

(VA)

wherein:

$R^9$, $R^{10}$, $R^{11}$, $R^{12}$, $R^{13}$, $R^{14}$, $R^{21}$, and $R^{22}$ are as previously defined for Formula V; and $R^{23}$ is selected from the group consisting of hydrogen, alkyl and aryl.

A method of the present invention may provide for the synthesis of a compound of Formula I that is unsymmetrically substituted, optionally with diverse groups in rings A-D. This may provide for the incorporation of distinct auxochromes on the pyrrole rings A and C and/or the pyrroline rings B and D, such as, e.g., for wavelength-tuning. In some embodiments, a method of the present invention may comprise introducing a single tether (e.g., for bioconjugation and/or surface attachment) and/or a single water-solubilizing group. In some embodiments, a method of the present invention may comprise site-selective incorporation of single isotopes (e.g., $^{13}$C or 15N), such as, e.g., for vibronic studies. In some embodiments, a method of the present invention may comprise introducing one or more distinct push-pull substituents on a compound of Formula I, optionally wherein different push-pull substituents may be present on opposite sides of the compound (e.g., a different push-pull substituent may be present on ring A and/or B compared to the substituents on ring C and/or D, respectively). In some embodiments, a method of the present invention may comprise incorporating and/or using the compound of Formula I as a building block in the construction of multi-pigment arrays, such as, e.g., for studies of light-harvesting and/or energy transduction.

A method of the present invention may comprise a directed joining of two distinct dihydrodipyrrins (i.e., a directed joining of BC and AD halves, wherein the BC half contains rings B and C and the AD half contains rings A and D). A compound of Formula II of the present invention corresponds to and/or is a precursor for the AD half and a compound of Formula III corresponds to and/or is a precursor for the BC half. A compound of Formula III may comprise one or more (e.g., 1, 2, 3, 4, 5, 6, 7, 8, 9, or more) different substituents than a compound of Formula III, which may provide one or more different substituents on the AD half compared to the BC half in a compound of Formula I.

In some embodiments, the step of condensing the compound of Formula H and the compound of Formula II in the composition comprising the first solvent is carried out using a Knoevenagel condensation reaction. In some embodiments, the composition (or the catalytic constituents when placed in water) may have a pH greater than 4 or of at least 7. In some embodiments, the composition (or the catalytic constituents when placed in water) may have a pH in a range of 4 to about 14 or 7 to about 14, and in some embodiments, a pH of about 4.5, 5, 5.5, 6, 6.5, 7, 7.5, 8, 8.5, 9, 9.5, 10, 10.5, 11, 11.5, 12, 12.5, 13, 13.5, or 14. In some embodiments, the composition may have a neutral pH and/or the Knoevenagel condensation may be carried out under neutral conditions. In some embodiments, condensing the compound of Formula II and the compound of Formula III may be by a base-mediated Knoevenagel condensation. When the Knoevenagel condensation is carried out under basic conditions, the composition may or may not comprise a base. In some embodiments, the composition comprises a weak base. The composition for a Knoevenagel condensation of the present invention may or may not comprise an acid. In some embodiments, if an acid is present, then the acid is present at a concentration insufficient to self-condense a compound of Formula II and/or a compound of Formula III. Thus, in some embodiments, if an acid is present in the composition, then the acid is not present at a concentration sufficient to provide self-condensation of the compound of Formula II and/or the compound of Formula III. In some embodiments, a Knoevenagel condensation of the present invention may be performed in the presence of an acid, but under conditions where neither the compound of Formula H nor the compound of Formula III undergoes self-condensation, which would provide a symmetrical bacteriochlorin. In some embodiments, the composition (or the catalytic constituents when placed in water) may be mildly acidic. In some embodiments, a method of the present invention may produce a product by self-condensation of a compound of Formula II and/or a compound of Formula III with a yield of less than about 5% (e.g., less than about 4%, 3%, 2%, 1%, 0.5%, or 0.1%). In some embodiments, a product that is produced by self-condensation of a compound of Formula II and/or a compound of Formula III is not detectable in a composition produced according to a method of the present invention. According to some embodiments, a method of the present invention does not comprise self-condensation of a compound of Formula H and/or a compound of Formula III.

Any suitable conditions for a Knoevenagel condensation may be used in a method of the present invention. In some embodiments, a Knoevenagel condensation of the present invention may utilize a catalyst, such as, e.g., a primary, secondary, and/or tertiary amine or a HX salt thereof where X is, e.g., a halogen, acetate, triflate, and/or the like and R for the primary (i.e., RNH$_2$), secondary (i.e., R$_2$NH), and tertiary (i.e., R₃N) amine is each independently selected from alkyl and aryl; piperidinium acetate/AcOH; NH₄OAc; KF; CsF; RbF; TiCl₄/R₃N; pyridine; piperidine; dry alumina; AlPO₄/Al₂O₃; xonotlite with KO$^t$Bu, zinc acetate; and/or the like. Any suitable solvent (e.g., a polar protic, polar aprotic, and/or nonpolar solvent) may be used in a Knoevenagel condensation of the present invention. In some embodiments, the solvent may be an organic solvent (e.g., dichloromethane, etc.), an inorganic solvent (e.g., sulfur dioxide, etc.), or water. A Knoevenagel condensation of the present invention may be carried out at any suitable temperature. In some embodiments, the Knoevenagel condensation may be carried out at room temperature. In some embodiments, the Knoevenagel condensation may be heated using conventional methods. In some embodiments, the Knoevenagel condensation may be heated with microwave irradiation. The reaction mixture for the Knoevenagel condensation may be nonaqueous but need not be anhydrous, and may conveniently be carried out exposed to air.

The Knoevenagel condensation may form an intermediate, which may be a bilin intermediate. In some embodiments, the intermediate has a structure represented by Formula VI:

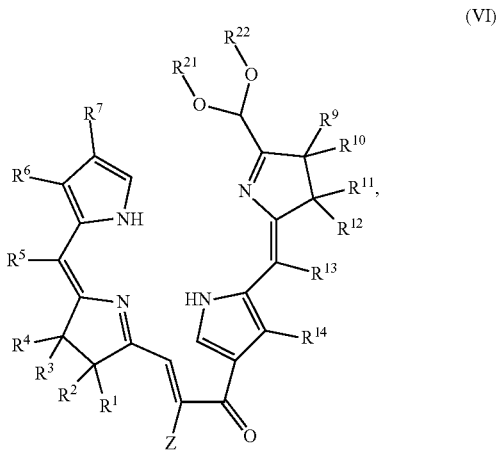

(VI)

or a metal conjugate thereof (e.g., a metal chelate thereof), wherein:

$R^1$, $R^2$, $R^3$, $R^4$, $R^5$, $R^6$, $R^7$, $R^9$, $R^{10}$, $R^{11}$, $R^{12}$, $R^{13}$, and $R^{14}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;
or $R^3$ and $R^4$ together are =O or spiroalkyl;
or $R^9$ and $R^{10}$ together are =O or spiroalkyl;
or $R^{11}$ and $R^{12}$ together are =O or spiroalkyl;
or $R^{15}$ and $R^{16}$ together are =O;

or $R^5$ and $R^6$ together represent a fused aromatic or heteroaromatic ring systems;
or $R^6$ and $R^7$ together represent a fused aromatic or heteroaromatic ring systems;
or $R^{13}$ and $R^{14}$ together represent a fused aromatic or heteroaromatic ring systems;
$R^{21}$ and $R^{22}$ are each independently selected from the group consisting of hydrogen, alkyl and aryl, or $R^{21}$ and $R^{22}$ taken together represent a C2-C4 alkylene; and
Z is an electron-withdrawing group (e.g., —CO₂R$^{17}$, —C(O)NHR$^{17}$, —C(O)NR$^{17}$R$^{18}$, —C(O)R$^{17}$, —CN, —C═N—NR$^{17}$R$^{18}$, —PO(OR$^{17}$)₂, —SO₂OR$^{17}$, —SO₂NR$^{17}$R$^{18}$, —SO₂R$^{17}$, and —SiR$^{17}$R$^{18}$R$^{18}$, and wherein R$^{17}$, R$^{18}$, and R$^{19}$ are, in each occurrence, independently selected from the group consisting of hydrogen, alkyl and aryl).

In some embodiments, the intermediate has a structure represented by Formula VIA:

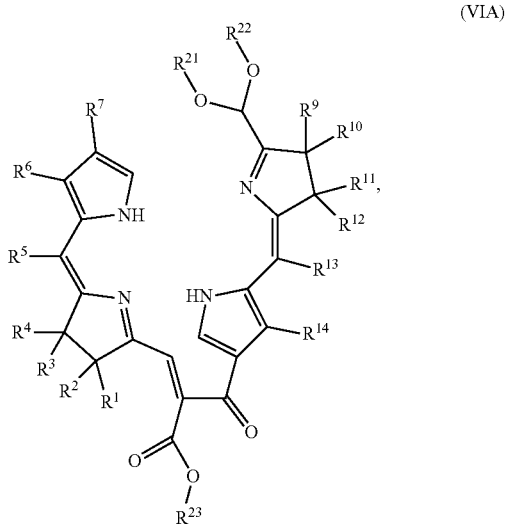

(VIA)

or a metal conjugate thereof (e.g., a metal chelate thereof), wherein:

$R^1$, $R^2$, $R^3$, $R^4$, $R^5$, $R^6$, $R^7$, $R^9$, $R^{10}$, $R^{11}$, $R^{12}$, $R^{13}$, $R^{14}$, $R^{21}$, and $R^{22}$ are as previously defined for Formula VI; and $R^{23}$ is selected from the group consisting of hydrogen, alkyl and aryl.

In some embodiments, following a Knoevenagel condensation, the intermediate may be condensed in a second solvent in the presence of an acid and/or under acidic conditions. The condensation of the intermediate may be a one-pot reaction (i.e., carried out in one pot and/or flask). In some embodiments, the condensation comprises an acid-mediated electrophilic substitution (e.g., an electrophilic aromatic substitution) and/or a Nazarov cyclization to form the compound of Formula I. The second solvent may be an organic solvent, an inorganic solvent, or water. Example solvents include, but are not limited to, acetonitrile, methylene chloride, chloroform, tetrahydrofuran, chlorobenzene, ethanol, 1,2-dichloroethane (DCE), dichloromethane, nitromethane, and/or toluene. Any suitable acid may be used to condense the intermediate. Examples acids include, but are not limited to, triflic acid, BF₃ etherate, SnCl₄, InCl₃, trifluoroacetic acid, toluenesulfonic acid, Sc(OTf)₃, In(OTf)₃, Hf(OTf)₄, boron trifluoride ethyl etherate (BF$_3$.OEt$_2$), TMSOTf/DTBP, and/or Yb(OTf)$_3$. In some embodiments, the acid is a Lewis acid. In some embodiments, the acid may comprise a lanthanide. The reaction may be carried out at any suitable temperature, such as, e.g., a temperature in a range of about 0 to about 100° C., and conveniently at room temperature, for any suitable time period, such as, e.g., for a few minutes, 1 to 4 hours, or a day. The reaction mixture comprising the second solvent may be nonaqueous but need not be anhydrous, and may conveniently be carried out exposed to air. A method of the present invention may provide a compound of Formula I in a yield of at least 50%, such as, for example, in a range of about 50% to about 90% or about 60% to about 80%. In some embodiments, the method may provide a compound of Formula I in a yield of about 50%, 55%, 60%, 65%, 70%, 75%, 80%, 85%, 90%, 95%, or more.

In some embodiments, a method of the present invention comprises metalating a compound of the present invention. In some embodiments, a method of the present invention comprises metalating a compound of Formula I to produce a metal conjugate of the compound of Formula I (e.g., a metal chelate of the compound of Formula I). A compound of the present invention may be a metal conjugate (e.g., a metal chelate) and may comprise a metal selected from the group consisting of Pd, Pt, Mg, Zn, Al, Ga, In, Sn, Cu, Ni, Au, and Fe. A compound of the present invention may be metalated with any suitable metal in accordance with known techniques. See, e.g., U.S. Pat. No. 6,208,553. Suitable metals include, but are not limited to, Pd(II), Pt(II), Mg(II), Zn(II), Al(III), Ga(III), In(III), Sn(IV), Cu(II), Ni(II), Au(III), Fe(II), and Fe(III). Where the metal is trivalent or tetravalent a counterion is included as necessary in accordance with known techniques. As used herein, a metal conjugate includes a metal chelate.

In some embodiments, a method of the present invention may comprise modifying a compound of Formula I, such as, e.g., using derivatization chemistry known to those of skill in the art. For example, in some embodiments, a method of the present invention may comprise modifying a compound of Formula I to provide a modified form, such as, but not limited to, a salt, a conjugate such as a metal chelate, and/or a prodrug. In some embodiments, one or more substituents (e.g., 1, 2, 3, 4, 5, 6, or more) may be added to a compound of Formula I and/or one or more substituents (e.g., 1, 2, 3, 4, 5, 6, or more) may be removed from a compound of Formula I. In some embodiments, ring E in a compound of Formula I may be derivatized at one or more of sites $13^1$ oxo, $13^2$ methylene, and $13^2$-carboalkoxy. In some embodiments, a method of the present invention may comprise allomerization and/or splitting of ring E, such as, e.g., by scission of the $13^1$-$13^2$ C—C bond, using methods known to those of skill in the art, such as, e.g., those described in Kozyrev, et al. *J. Org. Chem.* 2006, 71, 1949-1960; Seely, G. R. In *The Chlorophylls*; Vernon, L. P., Seely, G. R., Eds.; Academic Press: New York, N.Y., 1966; pp 67-109; and Hynninen, P. H. In *Chlorophylls;* Scheer, H., Ed.; CRC Press: Boca Raton, Fla., 1991; pp 145-209.

In some embodiments, Z in a compound of the present invention (e.g., a compound of Formula I and/or a compound of Formula III) is selected from the group consisting of —CO$_2$R$^{17}$, —C(O)NHR$^{17}$, —C(O)NR$^{17}$R$^{18}$, —C(O)R$^{17}$, —CN, —C=N—NR$^{17}$R$^{18}$, —PO(OR$^{17}$)$_2$, —SO$_2$OR$^{17}$, —SO$_2$NR$^{17}$R$^{18}$, —SO$_2$R$^{17}$, and —SiR$^{17}$R$^{18}$R$^{19}$, wherein R$^{17}$, R$^{18}$, and R$^{19}$ are, in each occurrence, independently selected from the group consisting of hydrogen, alkyl, and aryl.

In some embodiments, a method of the present invention may comprise removing at least a portion of Z in a compound of Formula I and/or modifying Z (e.g., substituting all or a portion of Z with one or more substitutents) in a compound of Formula I. Thus, some embodiments may comprise removing all or a portion of the electron-withdrawing group (i.e., Z) in a compound of Formula I. In some embodiments, the method may comprise removing and/or replacing all or a portion of Z in a compound of Formula I with a different substitutent, such as, for example, hydrogen.

In some embodiments, a compound of the present invention (e.g., a compound of Formula I, a compound of Formula I, and/or a compound of Formula III) may comprise an alkyl group (e.g., a methyl group) at R$^1$, R$^2$, R$^3$, R$^4$, R$^9$, R$^{10}$, R$^{11}$, and/or R$^{12}$. In some embodiments, at least two of R$^1$, R$^2$, R$^3$, and R$^4$ comprise an alkyl group and/or at least two of R$^9$, R$^{10}$, R$^{11}$, and/or R$^{12}$ comprise an alkyl group. In some embodiments, a pyrroline ring of a compound of Formula II (e.g., ring D) and/or a compound of Formula III (e.g., ring B) comprises a gem-dialkyl group (e.g., a gem-dimethyl group). In some embodiments, one or more pyrroline rings (e.g., ring B and/or ring D) in a compound of Formula I comprises a gem-dialkyl group (e.g., a gem-dimethyl group). Including a gem-dialkyl group on one or more pyrroline rings in a compound of the present invention may block any adventitious (aerobic) dehydrogenation, which may lead to a more unsaturated chlorin or porphyrin.

A compound of the present invention (e.g., a compound of Formula I, a compound of Formula H, and/or a compound of Formula III) may comprise a linking group, a hydrophilic group, a surface attachment group, and/or a targeting group (e.g., a protein, peptide, antibody, nucleic acid, etc.). In some embodiments, at least one of R$^1$ through R$^{19}$ and R$^{24}$ through R$^{26}$ comprises a linking group, a hydrophilic group, a surface attachment group, and/or a targeting group.

In some embodiments, R$^6$, R$^7$, R$^{14}$, R$^{23}$, and/or Z may comprise a hydrophilic group, a linking group, a surface attachment group, and/or a targeting group. In some embodiments, only one of R$^6$, R$^7$, R$^{14}$, R$^{23}$, and Z comprises a hydrophilic group, a linking group, a surface attachment group, and/or a targeting group. In some embodiments, R$^6$, R$^7$, and/or R$^{14}$ may comprise a hydrophilic group, a linking group, a surface attachment group, and/or a targeting group. In some embodiments, at least one R$^6$, R$^7$, and R$^{14}$ comprises a substituent that may be used for and/or provides wavelength tuning.

In some embodiments, R$^{17}$, R$^{18}$, and/or R$^{19}$ may comprise a hydrophilic group, a linking group, a surface attachment group, and/or a targeting group. In some embodiments, only one of R$^{17}$, R$^{18}$, and/or R$^{19}$ comprises a hydrophilic group, a linking group, a surface attachment group, and/or a targeting group.

In some embodiments, R$^1$ comprises a hydrophilic group, and R$^2$, R$^3$, and/or R$^4$ comprise a linking group or targeting group; or R$^2$ comprises a hydrophilic group, and R$^1$, R$^3$, and/or R$^4$ comprises a linking group or targeting group; or R$^3$ comprises a hydrophilic group, and R$^1$, R$^2$, and/or R$^4$ comprises a linking group or targeting group; or R$^4$ comprises a hydrophilic group, and R$^1$, R$^2$, and/or R$^3$ comprises a linking group or targeting group; or R$^9$ comprises a hydrophilic group, and R$^{10}$, R$^{11}$, and/or R$^{12}$ comprise a linking group or targeting group; or R$^{10}$ comprises a hydrophilic group, and R$^9$, R$^{11}$, and/or R$^{12}$ comprises a linking group or targeting group; or R$^{11}$ comprises a hydrophilic group, and R$^9$, R$^{10}$, and/or R$^{12}$ comprises a linking group or targeting group; or $R^{12}$ comprises a hydrophilic group, and $R^9$, $R^{10}$, and/or $R^{11}$ comprises a linking group or targeting group.

In some embodiments, $R^1$ comprises a linking group or targeting group, and $R^2$, $R^3$, and/or $R^1$ comprise a hydrophilic group; or $R^2$ comprises a linking group or targeting group, and $R^1$, $R^3$, and/or $R^4$ comprises a hydrophilic group; or $R^3$ comprises a linking group or targeting group, and $R^1$, $R^2$, and/or $R^4$ comprises a hydrophilic group; or $R^1$ comprises a linking group or targeting group, and $R^1$, $R^2$, and/or $R^3$ comprises a hydrophilic group; or $R^9$ comprises a linking group or targeting group, and $R^{10}$, $R^{11}$, and/or $R^{12}$ comprise a hydrophilic group; or $R^{10}$ comprises a linking group or targeting group, and $R^9$, $R^{11}$, and/or $R^{12}$ comprises a hydrophilic group; or $R^{11}$ comprises a linking group or targeting group, and $R^9$, $R^{10}$, and/or $R^{12}$ comprises a hydrophilic group; or $R^{12}$ comprises a linking group or targeting group, and $R^9$, $R^{10}$, and/or $R^{11}$ comprises a hydrophilic group.

According to some embodiments, a compound of Formula I may contain only one hydrophilic group, linking group, surface attachment group, and/or targeting group. In some embodiments, only one half of the compound of Formula I (e.g., the half comprising rings A and D or the half comprising the rings B and C) contains the one hydrophilic group, linking group, surface attachment group, and/or targeting group. In some embodiments, one of $R^1$, $R^2$, $R^3$, $R^4$, $R^5$, $R^6$, $R^7$, $R^{24}$, and $R^{25}$ comprises a hydrophilic group or one of $R^8$, $R^9$, $R^{10}$, $R^{11}$, $R^{12}$, $R^{13}$, $R^{14}$, $R^{15}$, $R^{16}$, and $R^{26}$ comprises a hydrophilic group. In some embodiments, one of $R^1$, $R^2$, $R^3$, $R^4$, $R^5$, $R^6$, $R^7$, $R^{24}$, and $R^{25}$ comprises a linking group or one of $R^8$, $R^9$, $R^{10}$, $R^{11}$, $R^{12}$, $R^{13}$, $R^{14}$, $R^{15}$, $R^{16}$, and $R^{26}$ comprises a linking group. In some embodiments, one of $R^1$, $R^2$, $R^3$, $R^4$, $R^5$, $R^6$, $R^7$, $R^{24}$, and $R^{25}$ comprises a surface attachment group or one of $R^8$, $R^9$, $R^{10}$, $R^{11}$, $R^{12}$, $R^{13}$, $R^{14}$, $R^{15}$, $R^{16}$, and $R^{26}$ comprises a surface attachment group. In some embodiments, one of $R^1$, $R^2$, $R^3$, $R^4$, $R^5$, $R^6$, $R^7$, $R^{24}$, and $R^{25}$ comprises a targeting group or one of $R^8$, $R^9$, $R^{10}$, $R^{11}$, $R^{12}$, $R^{13}$, $R^{14}$, $R^{15}$, $R^{16}$, and $R^{26}$ comprises a targeting group.

In some embodiments, a compound of Formula II may contain only one hydrophilic group, linking group, surface attachment group, and/or targeting group. One of $R^1$, $R^2$, $R^3$, $R^4$, $R^5$, $R^6$, $R^7$, $R^{24}$, and $R^{25}$ may comprise a hydrophilic group, linking group, surface attachment group, and/or targeting group. In some embodiments, a compound of Formula III may contain only one hydrophilic group, linking group, surface attachment group, and/or targeting group. One of $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{26}$ may comprise the hydrophilic group, linking group, surface attachment group, and/or targeting group.

In some embodiments, a compound of the present invention (e.g., a compound of Formula I and/or a compound of Formula II) comprises a halogen such as, for example, bromine. In some embodiments, the halogen may be used for subsequent exploitation and/or modification following formation of the compound of Formula I. In some embodiments, one of $R^1$, $R^2$, $R^3$, $R^4$, $R^5$, $R^6$, $R^7$, $R^{17}$, $R^{18}$, $R^{19}$, $R^{24}$, and $R^{25}$ in a compound of Formula I and/or a compound of Formula II comprises a halogen. In some embodiments, $R^7$ in a compound of Formula I and/or a compound of Formula II comprises a halogen (e.g., bromine). In some embodiments, a method of the present invention does not require halogenation (e.g., bromination) following formation of the compound of Formula I.

A linking group may be included in a compound of the present invention (e.g., a compound of Formula I, a compound of Formula II, and/or a compound of Formula III) to provide a reactive site for conjugation so that the compound may be coupled to and/or conjugated to other groups such as proteins, peptides, targeting agents such as, e.g., antibodies, polymers, particles such as, e.g., nanoparticles, organic, polymeric or inorganic beads, other solid support surfaces, etc., to form additional active compounds of the invention. In general, each group may be attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R' is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group may be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc., acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-iminobiotin, etc. Linking groups such as the foregoing are known and described in U.S. Pat. Nos. 6,728,129; 6,657,884; 6,212,093; and 6,208,553.

Other example groups may be attached to a compound of the present invention (e.g., a compound of Formula I, a compound of Formula II, and/or a compound of Formula III) to form a conjugate by means of a linking group to tune or adjust the solubility properties of the bacteriochlorin, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups may be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc., may be attached by means of the linking group. Where such additional compounds are attached to form a conjugate that may be attached directly to the bacteriochlorin or attached by means of an intervening group such as a hydrophilic group, it may depend upon the particular linking group employed (as noted above).

In some embodiments, a compound of the present invention (e.g., a compound of Formula I, a compound of Formula II, and/or a compound of Formula III) may include a hydrophilic group coupled at one or more sites noted above, e.g., covalently coupled thereto, to facilitate delivery thereof, or improve stability, in accordance with known techniques (e.g., to the N-terminus of the peptide). Suitable hydrophilic groups may include polyols or polyalkylene oxide groups, including straight and/or branched-chain polyols, with particular examples including, but not limited to, poly(propylene glycol), polyethylene-polypropylene glycol, and/or poly(ethylene glycol). The hydrophilic group may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group. Suitable hydrophilic groups also include ionic or polar groups, including linear or branched alkyl groups substituted with ionic or polar groups, examples of which include but are not limited to swallowtail groups such as described in Borbas and Lindsey, U.S. Pat. No. 8,530,459.

As noted above, compounds of the present invention may be substituted with a surface attachment group, which may be in protected or unprotected form. A surface attachment group may be a reactive group coupled directly to the bacteriochlorin, or coupled to the bacteriochlorin by means of an intervening linker. Linkers L may be aryl, alkyl, heteroaryl, heteroalkyl (e.g., oligoethylene glycol), peptide, polysaccharide, etc. Examples of surface attachment groups (with the reactive site or group in unprotected form) include, but are not limited to, alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl)phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl)phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl, 2-tellurylethyl, 3-tellurylpropyl, 2-(4-tellurylphenyl)ethynyl, 4-(2-(4-tellurylphenyl)ethynyl) phenyl, 4-tellurylmethylphenyl, 4-(2-tellurylethyl) phenyl, 4-(3-tellurylpropyl)phenyl, 4-(2-(4-tellurylmethylphenyl)ethynyl)phenyl;

4-(dihydroxyphosphoryl)phenyl, (dihydroxyphosphoryl)methyl, 2-(dihydroxyphosphoryl) ethyl, 3-(dihydroxyphosphoryl)propyl, 2-[4-(dihydroxyphosphoryl)phenyl] ethynyl, 4-[2-[4-(dihydroxyphosphoryl)phenyl]ethynyl] phenyl, 4-[(dihydroxyphosphoryl)methyl]phenyl, 4-[2-(dihydroxyphosphoryl)ethyl]phenyl, 4-[2-[4-(dihydroxyphosphoryl)methylphenyl]ethynyl]phenyl;

4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl] phenyl, 4-[(hydroxy(mercapto)phosphoryl)methyl]phenyl, 4-[2-(hydroxy(mercapto)phosphoryl)ethyl]phenyl, 4-[2-[4-(hydroxy(mercapto)phosphoryl)methylphenyl] ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl] phenyl, 4-(cyanomethyl)phenyl, 4-(2-cyanoethyl)phenyl, 4-[2-[4-(cyanomethyl)phenyl]ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl,4-(4,4,5,5-tetramethyl-1,3,2-dioxaborolan-2-yl)phenyl;

formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl;

4-(bromomethyl)phenyl, and 2-bromoethyl.

In addition to the monodentate linker-surface attachment groups described above, multidentate linkers may be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J. Org. Chem.* 1999, 64, 1968-1971; Fox, M. A. et al. *Langmuir*, 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science,* 2001, 494, 1-20; Whitesell, J. K.; Chang, H. K. *Science,* 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl] methyl}phenyl,
1,1,1-tris[4-dihydroxyphosphorylmethyl)phenyl]methyl, and
4-{1,1,1-tris[4-(dihydroxyphosphorylmethyl)phenyl] methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to: Alkene surface attachment groups (2, 3, 4 carbons) such as:

3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.

Alkyne surface attachment groups (2, 3, 4 carbons) such as:

3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl, 4-[5-(1-butyn-4-yl)nona-1,8-diyn-5-yl]biphen-4'-yl,
Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc.,
Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc.,
Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.
Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and
Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the present invention (e.g., a compound of Formula I) may be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Active compounds of the present invention include prodrugs of the compounds described herein. As noted above, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

The methods and intermediates described herein may be useful for the synthesis of compounds of Formula I as described herein. Such compounds may be useful per se or in further modified form (e.g., as a salt, metalated compound, conjugate, and/or prodrug) for diagnostic and/or therapeutic purposes in like manner as other compounds described for photodynamic therapy, such as described in US Patent Application Publication No. 2004/0044197 to Pandey et al. and as set forth in further detail below. In some embodiments, a compound of the present invention may be used in an application where wavelength tuning and/or bioconjugation is utilized and/or sought. A method and/or compound of the present invention may provide for one or more (e.g., 1, 2, 3, 4, 5, or more) different substitutents to be attached at one or more (e.g., 1, 2, 3, 4, 5, or more) locations on a compound of the present invention (e.g., on the AD half, but not the BC half or vice versa), which may be advantageous in applications including, but not limited to, wavelength tuning and/or bioconjugation.

An advantage of the compounds of the present invention may be their stability and absorption characteristics. In some embodiments, a "neat" composition consisting of an active compound of the present invention (e.g., a compound of Formula I, or the pharmaceutically acceptable salts, prodrugs, or conjugates thereof (e.g., with a targeting agent such as a protein, peptide or antibody)) may be provided, wherein the composition has or is characterized by a peak Molar absorption coefficient in solution of at least 10,000, up to 300,000 $M^{-1}$ $cm^{-1}$ or more, at a wavelength in a range from 650 to 850 or 900 nanometers or more (it being understood that (a) the active compound must be placed into solution to determine its peak Molar absorption coefficient at the indicated wavelength; and (b) the compound may exhibit additional peaks outside of this range, or multiple peaks within this range).

In some embodiments, the present invention may provide compositions comprising or consisting essentially of an active compound of the present invention (e.g., compounds of Formula I, or the pharmaceutically acceptable salts, prodrugs, or conjugates thereof (e.g., with a targeting agent such as a protein, peptide or antibody)) in a solvent. The amount of solvent is not critical and may comprise from about 0.01 or 1 to about 99 or 99.99 percent by weight of the composition. The composition may have or may be characterized by a peak Molar absorption coefficient in solution of at least 10,000, up to 300,000 M-'cm' or more, at a wavelength in a range from 650 to 850 or 900 nanometers or more. It will be appreciated that agitation may be required to break agglomerated particles back into solution prior to determining molar absorption, but that some level of agglomeration may actually be desired for practical use of the composition. Suitable solvents depend upon the particular compound and intended use for that compound, but include both organic solvents, aqueous solvents and combinations thereof.

The compositions, be they the bacteriochlorin compounds in "neat" form or the compounds mixed with a solvent, may have or exhibit a loss of not more than 10, 15 or 20 percent by weight of the bacteriochlorin compound of the present invention (due to degradation thereof) when stored in a sealed vessel (e.g., a flask ampoule or vial), at room temperature in the absence of ambient light for at least 3 or 4 months. Degradation can be determined by spectroscopy, thin-layer chromatography, NMR spectroscopy, and/or mass spectrometry, in accordance with known techniques.

Flow cytometry is known and described in, for example, U.S. Pat. Nos. 5,167; 5,915,925; 6,248,590; 6,589,792; and 6,890,487. In some embodiments the particle being detected, such as a cell, is labelled with a luminescent compound such as a phosphor and/or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The bacteriochlorins described herein may be useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

According to some embodiments provided are pharmaceutical compositions. A pharmaceutical composition of the present invention may comprise a therapeutically effective amount of one or more of the compounds of the present invention (e.g., a compound of Formula I), which may be useful in the prevention, treatment, and/or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

Pharmaceutical compositions may exhibit the absorption characteristics and/or storage and/or stability characteristics described above.

In addition, the compounds may be formulated as the sole pharmaceutically active ingredient in the composition or may be combined with other active ingredients.

The compositions may contain one or more compounds of the present invention. In some embodiments, the compounds may be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof may be (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions may be effective for delivery of an amount, upon administration, that treats, prevents, and/or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of a compound of the present invention is dissolved, suspended, dispersed or otherwise mixed in a selected carrier at an effective concentration such that the treated condition is relieved, prevented, or one or more symptoms may be ameliorated.

The active compound may be included in the pharmaceutically acceptable carrier in an amount sufficient to exert a therapeutically useful effect in the absence of undesirable side effects on the subject treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition may depend on absorption, inactivation and excretion rates of the active compound, the physicochemical characteristics of the compound, the dosage schedule, and/or the amount administered as well as other factors known to those of skill in the art. For example, the amount that is delivered may be sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of the active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms may be prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration may be sufficient for ameliorating the symptoms of the disease, disorder or condition treated and may be empirically determined.

The pharmaceutical compositions may be provided for administration to humans and/or animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions may, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

In some embodiments, a composition of the present invention may be suitable for oral administration. Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, in one embodiment, capsules or tablets. The tablets, pills, capsules, troches and the like may contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, may be provided in a composition that protects it from the acidic environment of the stomach. For example, the composition may be formulated in an enteric coating that maintains its integrity in the stomach and releases the active compound in the intestine. The composition may also be formulated in combination with an antacid or other such ingredient. When the dosage unit form is a capsule, it may contain, in addition to material of the above type, a liquid carrier such as a fatty oil. In addition, dosage unit forms may contain various other materials which modify the physical form of the dosage unit, for example, coatings of sugar and other enteric agents. The compounds may be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials may also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(loweralkyl) acetals of loweralkyl aldehydes such as acetaldehyde diethyl acetal.

Parenteral administration, in one embodiment characterized by injection, either subcutaneously, intramuscularly or intravenously is also contemplated herein. Injectables may be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, xanthan gum, hydroxypropyl methylcellulose and polyvinylpyrrolidone. Emulsifying agents include Polysorbate 80 (TWEEN™ 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized powders, which can be reconstituted for administration as solutions, emulsions and other mixtures, may also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures may be prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract may be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients may be administered. These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983; 6,261,595; 6,256,533; 6,167,301; 6,024,975; 6,010715; 5,985,317; 5,983,134; 5,948,433 and 5,860,957.

For example, pharmaceutical dosage forms for rectal administration are rectal suppositories, capsules and tablets for systemic effect. Rectal suppositories as used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, may be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Escherichia coli, Neisseria gonorrhosae, Neisseria meningitidis, Pneumococcus, Hemophilis influenzae* B, *Treponema pallidum*, Lyme disease, spirochetes, *Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma man-* soni, *Schistosoma japonicum, Mesocestoides corti, Emeria tenella, Onchocerca volvulus, Leishmania tropica, Trichinella spiralis, Theileria parva, Taenia hydatigena, Taenia ovis, Taenia saginata,* Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, may be appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to *T. gondii*, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes may be used, as may hybrid antibodies. Multispecific, including bispecific and hybrid, antibodies and antibody fragments may be used in the methods of the present invention for detecting and treating target tissue and may comprise at least two different substantially monospecific antibodies or antibody fragments, wherein at least two of the antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include $F(ab')_2$, $F(ab)_2$, Fab', Fab, Fv and the like including hybrid fragments. In some embodiments, fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin.

A ligand or one member of a ligand-receptor binding pair may be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorine6 via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein may also be conjugated to a ligand, such as an antibody, by using a coupling agent. Any bond which is capable of linking the components such that they are stable under physiological conditions for the time needed for administration and treatment is suitable. In some embodiments, the bond may be a covalent linkage. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies may be prepared by coupling the compound to targeting moieties by cleaving the ester on the "E" ring and coupling the compound via peptide linkages to the antibody through an N terminus, or by other methods known in the art. A variety of coupling agents, including cross-linking agents, may be used for covalent conjugation. Examples of cross-linking agents include N,N'-dicyclohexylcarbodiimide (DCC), N-succinimidyl-S-acetyl-thioacetate (SATA), N-succinimidyl-3-(2-pyridyidi-thio)propionate (SPDP), ortho-phenylene-dimaleimide (o-PDM), and sulfo-succinimidyl 4-(N-maleimido-methyl)-cyclohexane-1-carboxylate (sulfo-SMCC). See, e.g., Karpovsky et al., J. Exp. Med. 160:1686 (1984); and Liu, M A et al., Proc. Natl. Acad. Sci. USA 82: 8648 (1985). Other methods include those described by Brennan et al., Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.), which catalog is hereby incorporated by reference.

For example, DCC is a useful coupling agent that may be used to promote coupling of the alcohol NHS to chlorin e6 in DMSO forming an activated ester which may be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer may be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups may be joined to lysine ε-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which may be transformed to sulfonyl chlorides which react with amino groups. Photosensitizers which have carboxyl groups may be joined to amino groups on the polypeptide by an in situ carbodiimide method. Photosensitizers may also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, may use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

In some embodiments, a compound of the present invention (e.g., a compound of Formula I) may be a photosensitizing compound. A photosensitizing compound may be administered to a subject before a target tissue, target composition and/or subject is subjected to illumination. The photosensitizing compound may be administered as described elsewhere herein.

The dose of the photosensitizing compound may be determined clinically. Depending on the photosensitizing compound used, an equivalent optimal therapeutic level may need to be established. A certain length of time may be allowed to pass for the circulating or locally delivered photosensitizer to be taken up by the target tissue. The unbound photosensitizer is cleared from the circulation during this waiting period, or additional time may optionally be provided for clearing of the unbound compound from non-target tissue. The waiting period may be determined clinically and may vary from compound to compound.

At the conclusion of this waiting period, a laser light source or a non-laser light source (including but not limited to artificial light sources such as fluorescent or incandescent light, or natural light sources such as ambient sunlight) may be used to activate the bound photosensitizer. The area of illumination may be determined by the location and/or dimension of the pathologic region to be detected, diagnosed or treated. The duration of illumination period may depend on whether detection or treatment is being performed, and may be determined empirically. A total or cumulative period of time anywhere from between about 4 minutes and 72 hours may be used. In one embodiment, the illumination period may be between about 60 minutes and 148 hours. In another embodiment, the illumination period may be between about 2 hours and 24 hours.

In some embodiments, the total fluence or energy of the light used for irradiating, as measured in Joules, may be between about 10 Joules and about 25,000 Joules; in some embodiments, between about 100 Joules and about 20,000 Joules; and in some embodiments, between about 500 Joules and about 10,000 Joules. Light of a wavelength and fluence sufficient to produce the desired effect may be selected, whether for detection by luminescence (e.g., fluorescence or phosphorescence) or for therapeutic treatment to destroy or impair a target tissue or target composition. Light having a wavelength corresponding at least in part with the characteristic light absorption wavelength of the photosensitizing agent may be used for irradiating the target issue.

The intensity or power of the light used may be measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

In one embodiment of using compounds disclosed herein for photodynamic therapy, the compounds are injected into the mammal, e.g. human, to be diagnosed or treated. The level of injection may be between about 0.1 and about 0.5 umol/kg of body weight. In the case of treatment, the area to be treated is exposed to light at the desired wavelength and energy, e.g. from about 10 to 200 $J/cm^2$. In the case of detection, luminescence is determined upon exposure to light at a wavelength sufficient to cause the compound to fluoresce and/or phosphoresce at a wavelength different than that used to illuminate the compound. The energy used in detection is sufficient to cause fluorescence and/or phosphorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A person may be instructed in how to use the kit using any of the instructions above or by receiving instructions in a classroom or in the course of treating a subject using any of the methods disclosed herein, for example.

Additional examples and specific examples of methods of using compounds and compositions of the present invention include, but are not limited to, the following:

(i) Treatment of Opportunistic Infections.

Compounds, compositions and methods of the invention may be useful for PDT of opportunistic infections, particularly of soft tissue. For antimicrobial treatment (via PDT) of infections, particularly wound infections, the infecting organism can include (as non limiting examples) *Staphylococcus aureus, Pseudomonas aeruginosa*, and *Escherichia coli*. In nosocomial infections, *P. aeruginosa* is responsible for 8% of surgical-wound infections and 10% of bloodstream infections. In some embodiments the subjects are immunocompromised subjects, such as those afflicted with AIDS or undergoing treatment with immunosupressive agents.

(ii) Treatment of Burns.

Infections by *S. aureus* and gram-positive bacteria in general are particularly pronounced in burns (Lambrechts, 2005). The multidrug resistance of *S. aureus* presents significant medical challenges. In this regard, compounds, compositions and methods of the invention may be useful for the treatment of opportunistic infections of burns.

(iii) Sepsis.

Compounds, compositions and methods of the invention may be useful for the PDT treatment of subjects afflicted with opportunistic infections of *Vibrio vulnificus*. *V. vulnificus*, a gram-negative bacterium, causes primary sepsis, wound infections, and gastrointestinal illness in humans.

(iv) Ulcers.

Compounds, compositions and methods of the invention may be useful for PDT treatment of the bacterium that causes ulcers (*Helicobacter pylori*). In the clinic, treatment may be effected in any suitable manner, such as by insertion of a fiber optic cable (akin to an endoscope but with provisions for delivery of red or near-IR light) into the stomach or afflicted region.

(v) Periodontal Disease.

Compounds, compositions and methods of the invention may be useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include *Porphyromonas gingivalis, Actinobacillus actinomycetemcomitans, Bacteroides forsythus, Campylobacter rectus, Elkenella corrodens, Fusobacterium nucleatum* subsp. *Polymorphum, Actinomyces viscosus*, and the streptococci. For such applications the compounds or compositions of the present invention may be topically applied (e.g., as a mouthwash or rinse) and then light administered with an external device, in-the-mouth instrument, or combination thereof.

(vi) Atherosclerosis.

Compounds, compositions and methods of the invention may be useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal (Demidova and Hamblin, 2004). Bacteriochlorins targeted to such inflammatory macrophages may be useful for PDT of vulnerable plaque.

(vii) Cosmetic and Dermatologic Applications.

Compounds, compositions and methods of the invention may be useful in PDT to treat a wide range of cosmetic dermatological problems, such as hair removal, treatment of psoriasis, or removal of skin discoloration. Ruby lasers are currently used for hair removal; in many laser treatments melanin is the photosensitized chromophore. Such treatments work reasonably well for fair-skinned individuals with dark hair. Compounds, compositions and methods of the invention may be used as near-IR sensitizers for hair removal, which enables targeting a chromophore with a more specific and sharp absorption band.

(viii) Acne.

Compounds, compositions and methods of the invention may be useful in PDT to treat acne. Acne vulgaris is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and compositions of the invention may be administered to subjects topically or parenterally (e.g., by subcutaneous injection) depending upon the particular condition.

(ix) Infectious Diseases.

Compounds, compositions and methods of the invention may be useful in PDT to treat infectious diseases. For example, Cutaneous leishmaniasis and sub-cutaneous leishmaniasis, which occurs extensively in the Mediterranean and Mideast regions, is currently treated with arsenic-containing compounds. PDT has been used to reasonable effect recently, at least in one case, on a human subject. The use of compounds and compositions of the present invention are likewise useful, and potentially offer advantages such as ease of synthesis and better spectral absorption properties.

(x) Tissue Sealants.

Compounds, compositions and methods of the invention may be useful in PDT as tissue sealants in subjects in need thereof. Light-activated tissue sealants are attractive for sealing wounds, bonding tissue, and closing defects in tissue. There are many applications where sutures or staples are undesirable, and use of such mechanical methods of sealing often leads to infection and scarring.

(xi) Neoplastic Disease.

Compounds, compositions and methods of the invention may be useful in PDT for treating neoplastic diseases or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and Kaposi sarcoma.

Further, in the modern medical field, there are a variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolution yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., Am. J. Radiol. 141: 1209 (1983). When MRI contrast agents are used diagnostically, they may be vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^1H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds may be used as image enhancing agents and provide labeling of specific target tissues or target compositions for diagnostic radiology, including MRI.

In some embodiments, a composition of the present invention may be used to detect target cells, target tissue, and/or target compositions in a subject. Any type of cells, tissue, and/or composition (e.g., normal or healthy cells and/or tissue, diseased cells and/or tissue, cancer cells, hyperproliferative cells and/or tissue, benign tumors, malignant tumors, aneurysms, etc.) may be detected in a subject. In some embodiments, a composition of the present invention may be used to detect the presence of target cells, target tissue, and/or target compositions in a subject. When the compounds provided herein are to be used for detection of target tissue or target composition, the compounds may be introduced into the subject and sufficient time may be allowed for the compounds to accumulate in the target tissue and/or to become associated with the target composition. The area of treatment is then irradiated, generally using light of an energy sufficient to cause luminescence (e.g., fluorescence or phosphorescence) of the compound, and the energy used is usually significantly lower than is required for photodynamic therapy treatment. Luminescence is determined upon exposure to light at the desired wavelength, and the amount of luminescence can be correlated to the presence of the compound, qualitatively or quantitatively, by methods known in the art.

In some embodiments, a composition of the present invention may be used to diagnose the presence of an infecting agent and/or the identity of an infecting agent in a subject. The compounds provided herein may be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound may be visualized, such as, e.g., by exposing the tissue and/or compound to light of an energy sufficient to cause luminescence of the compound or to cause the generation of heat and/or ultrasonic waves, or by imaging using diagnostic radiology, including MRI. By way of example, any one of the compounds provided herein may be conjugated to an antibody that is targeted against a suitable *Helicobacter pylori* antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject may be examined to determine whether any *Helicobacter pylori* is present. This may be done by MRI to detect accumulated compound because of the presence of $^{19}$F substituents, for example, or by irradiating the suspect target area with light of an energy sufficient to cause luminescence of the compound, such as by using fiberoptics, and detecting any luminescence of the targeted compound.

According to some embodiments of the present invention, bacteriochlorins of Formula I may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963.

Bacteriochlorins of Formula I may be used as chromophores in the light harvesting rods described in U.S. Pat. Nos. 6,407,330 and 6,420,648 (incorporated herein by reference). The light harvesting rod may comprise one or more bacteriochlorins of Formula I coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

In some embodiments, bacteriochlorins of the present invention may be useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The bacteriochlorins of the invention may comprise a member of a sandwich coordination compound in the information storage molecule, such as described in U.S. Pat. No. 6,212,093 to Li et al. or U.S. Pat. No. 6,451,942 to Li et al. The present invention is explained in greater detail in the following non-limiting experimental section.

EXAMPLES

The labeling/numbering of compounds provided in the examples sections is relevant to the examples section only and may not correspond to the labeling/numbering provided throughout the rest of the present application. Thus, the labeling/numbering of compounds in the examples section is not to be confused with the labeling/numbering of compounds throughout the rest of the application (e.g., in the summary and detailed description sections and claims).

Rational approaches to bacteriochlorins with nonidentical substituents on the two pyrrole units have been severely limited (Scheme 2): (1) Sonogashira coupling of a 3,13-dibromo-5-methoxybacteriochlorin (I-a) proceeds selectively at the unhindered 13-position, after which more forcing Pd-mediated conditions could be employed to install diverse substituents at the 3-position to give the differentially substituted bacteriochlorin (I-b).[8] (2) A 3,13-diacetyl-bacteriochlorin (I-c) underwent 15-bromination (I-d), setting up Pd-mediated α-arylation to close the annulated ring spanning positions 13 and 15, thereby forming the bacterio-13$^1$-oxophorbine (I-e). To date, I-e is the only bacterio-13$^1$-oxophorbine prepared by de novo synthesis. (3) A route to tolyporphin A diacetate,[9-11] a derivative of a naturally occurring dioxobacteriochlorin (not shown), is ingenious yet inordinately lengthy for our purposes. An alternative approach toward bacteriochlorins entails derivatization of porphyrins or chlorins.[12]

Scheme 2. Rational Routes to Unsymmetrically Substituted Bacteriochlorins

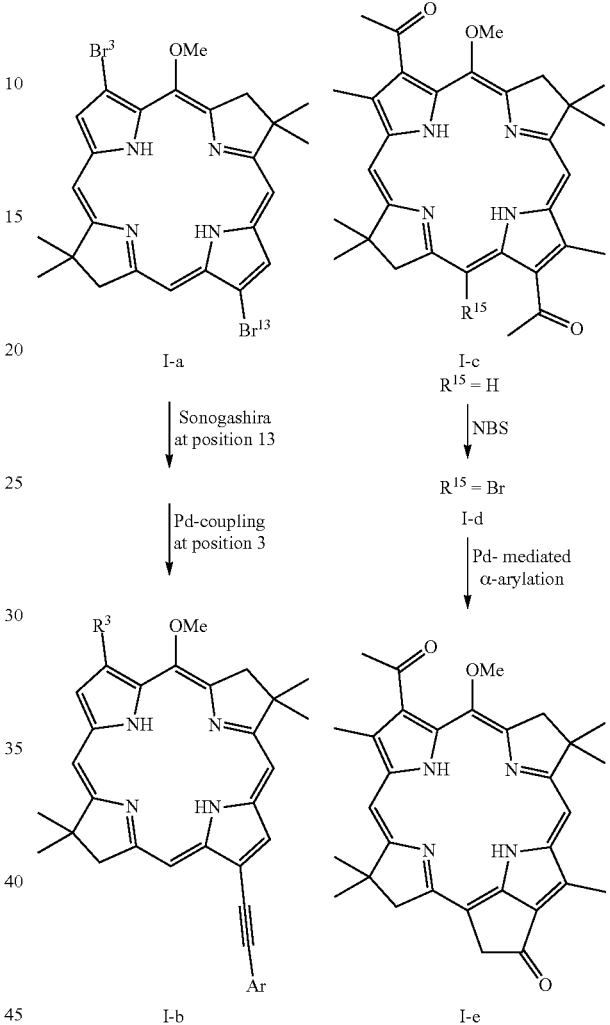

By contrast with these synthetic limitations, bacteriochlorophylls a, b and g contain distinct substituents in rings A-C, as well as ring E bearing a carbomethoxy group at the 13$^2$-position (Chart 1, provided in the Background section of the present application). The synthesis shown in Scheme 2 (right panel) affords the 13$^1$-oxobacteriophorbine macrocycle but lacking the 13$^2$-carbomethoxy group. The resulting macrocycles are akin to bacteriopyropheophorbides (Chart 2), which are the natural bacteriochlorophyll derivatives obtained upon demetalation and pyrolytic loss of the 13$^2$-carbomethoxy substituent. The functional role of the 13$^2$-carbomethoxy group remains unclear, whereas the coplanar keto group (13$^1$-position) is known to cause a bathochromic shift of the long-wavelength absorption band and to interact via hydrogen bonding with protein sites.[1] Note that the term isocyclic ring is typically used regardless of the presence or absence of the 13$^2$-carbomethoxy group, despite the vast chemistry that has been devoted to modifications of ring E.[13,14] To date, names for tetrapyrrole macrocycles bearing isocyclic rings derive from those of the natural compounds.[15]

Chart 2. Bacteriochlorophyll Derivatives and Bacterio-13¹-oxophorbine

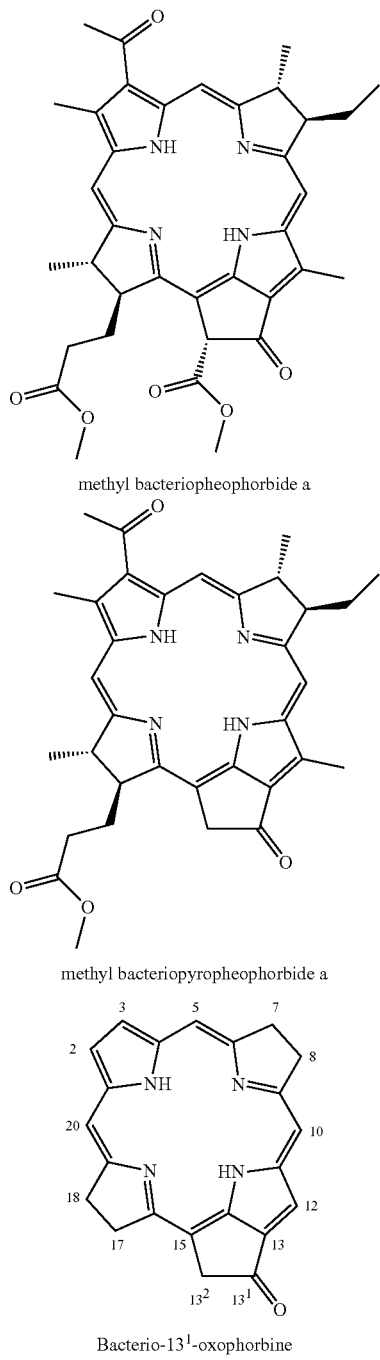

methyl bacteriopheophorbide a methyl bacteriopyropheophorbide a

Bacterio-13¹-oxophorbine

The synthesis of bacteriochlorins that are unsymmetrically substituted with diverse groups in rings A-D remains an unmet challenge. Access to such macrocycles would open a number of scientific opportunities, of which the following are representative: (1) incorporation of distinct auxochromes on the pyrrole rings A and C as well as the pyrroline rings B and D for wavelength-tuning; (2) introduction of a single tether (for bioconjugation or surface attachment) and/or a single water-solubilizing group; (3) site-selective incorporation of single isotopes (e.g., $^{13}C$ or $^{15}N$) for vibronic studies; (4) introduction of distinct push-pull substituents on opposite sides of the macrocycle; and (5) incorporation of the resulting tailored macrocycles as building blocks in the construction of multi-pigment arrays for studies of light-harvesting and energy transduction.

A rational and efficient route to bacteriochlorin macrocycles was developed that incorporates the β-ketoester-containing isocyclic ring as well as diverse substituents at the 2- and 3-positions, and is described herein. The route relies on directed joining of two distinct dihydrodipyrrins (BC and AD halves) by base-mediated Knoevenagel condensation followed by one-flask acid-mediated electrophilic aromatic substitution and Nazarov cyclization to form the macrocycle and create the isocyclic ring. The routes to the BC and AD halves, and the studies of the conditions for joining the two halves to form the bacteriochlorin are described herein. Static absorption and fluorescence spectroscopic properties of the new bacteriochlorins are also reported.

Results

I. Reconnaisance.

After several years of study (for an earlier published attempt, see reference 16), two precedents proved enlightening for developing a directed synthesis of unsymmetrically substituted bacteriochlorins. The first precedent was Woodward's pioneering synthesis of chlorin $e_6$ trimethyl ester, a precursor of chlorophyll, which relies on directed joining of an AD half and a BC half to form an unsymmetric porphyrin (Scheme 3).[17-19] Acid-catalyzed condensation between a dipyrromethane-thioaldehyde (W-31, Woodward numbering[9]) and a dipyrromethane-amine (W-32) gave a Schiff's base (W-33). Intramolecular condensation of the juxtaposed rings A and B in W-33 generated a single bilene-b salt; subsequent condensation between rings C and D under more forcing acidic conditions deftly closed the macrocycle and, upon dehydrogenation and acetylation, afforded the desired porphyrin (W-35) in 50% overall yield. In our case, to prepare an unsymmetric bacteriochlorin, dihydrodipyrrins would be the constituents instead of dipyrromethanes. Also required is a unit at the 3-pyrrole position of one dihydrodipyrrin to direct intermolecular joining of the BC and AD halves followed by an intramolecular joining of the resulting linear intermediate to close the macrocycle.

Scheme 3. Macrocycle Formation in Woodward's Approach to Chlorophyll

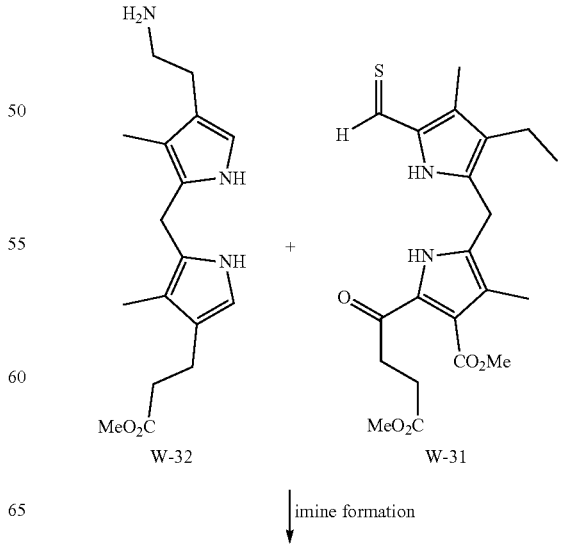

imine formation

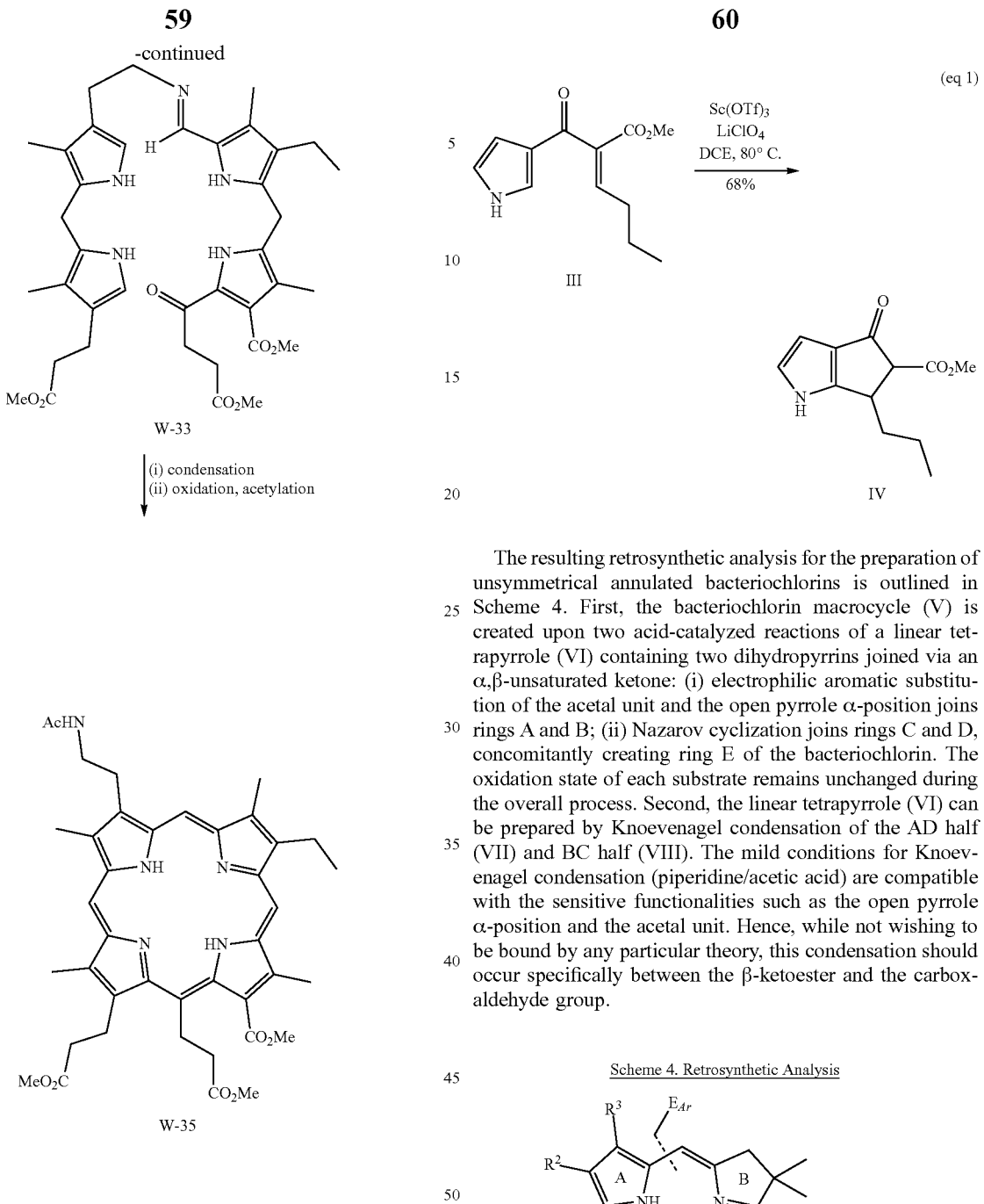

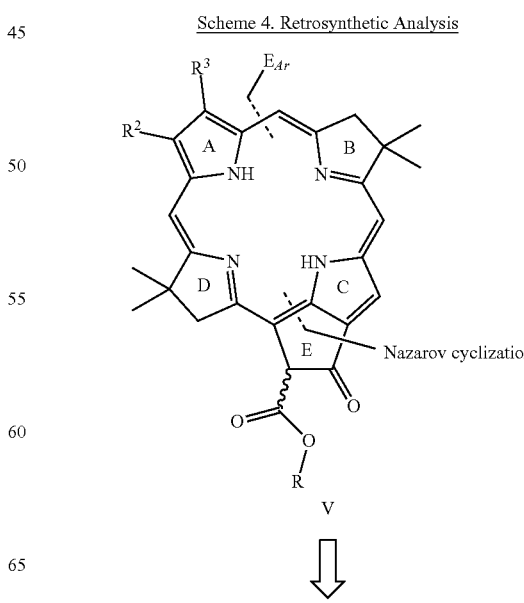

The resulting retrosynthetic analysis for the preparation of unsymmetrical annulated bacteriochlorins is outlined in Scheme 4. First, the bacteriochlorin macrocycle (V) is created upon two acid-catalyzed reactions of a linear tetrapyrrole (VI) containing two dihydropyrrins joined via an α,β-unsaturated ketone: (i) electrophilic aromatic substitution of the acetal unit and the open pyrrole α-position joins rings A and B; (ii) Nazarov cyclization joins rings C and D, concomitantly creating ring E of the bacteriochlorin. The oxidation state of each substrate remains unchanged during the overall process. Second, the linear tetrapyrrole (VI) can be prepared by Knoevenagel condensation of the AD half (VII) and BC half (VIII). The mild conditions for Knoevenagel condensation (piperidine/acetic acid) are compatible with the sensitive functionalities such as the open pyrrole α-position and the acetal unit. Hence, while not wishing to be bound by any particular theory, this condensation should occur specifically between the β-ketoester and the carboxaldehyde group.

The second precedent emerged from studies of the catalytic Nazarov cyclization of heteroaromatic compounds.[20] While there are only a few examples concerning cyclization of pyrrole substrates,[21-24] especially pyrroles lacking substitution at the nitrogen, one particularly germane example by Frontier and co-workers[2] appeared ideal for our case. Under a catalytic amount of Sc(OTf)$_3$ (10 mol %) and in the presence of LiClO$_4$ for 1.25 h, pyrrole III underwent ring closure at the 2-position in 68% yield (eq 1).[22] The resulting annulated pyrrole IV bears the same structural motif as in the isocyclic ring of bacteriochlorophylls a, b and g. The Nazarov substrate III could be prepared via Knoevenagel condensation of the β-ketoester-pyrrole and butanal.[22]

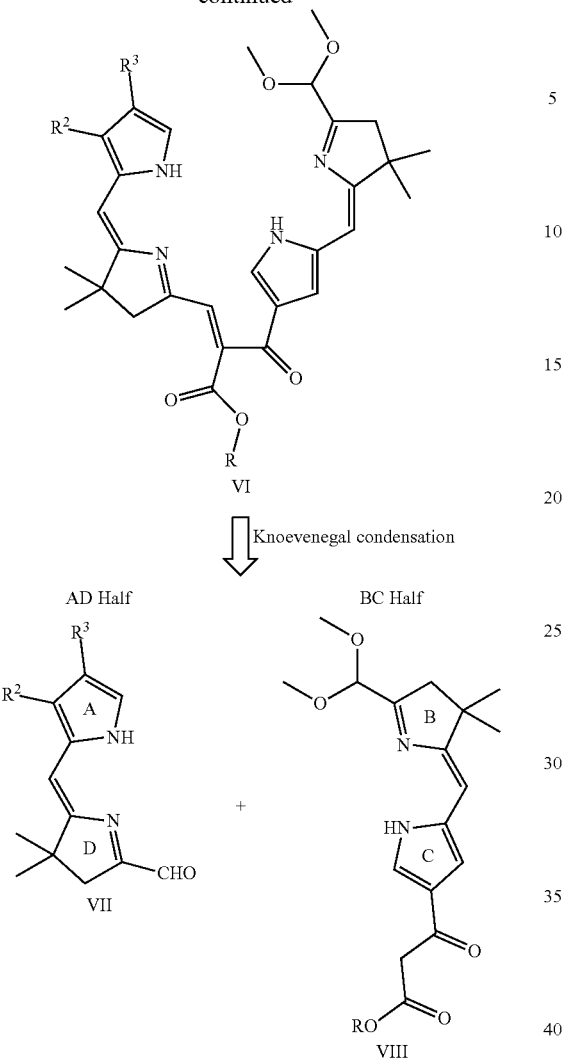

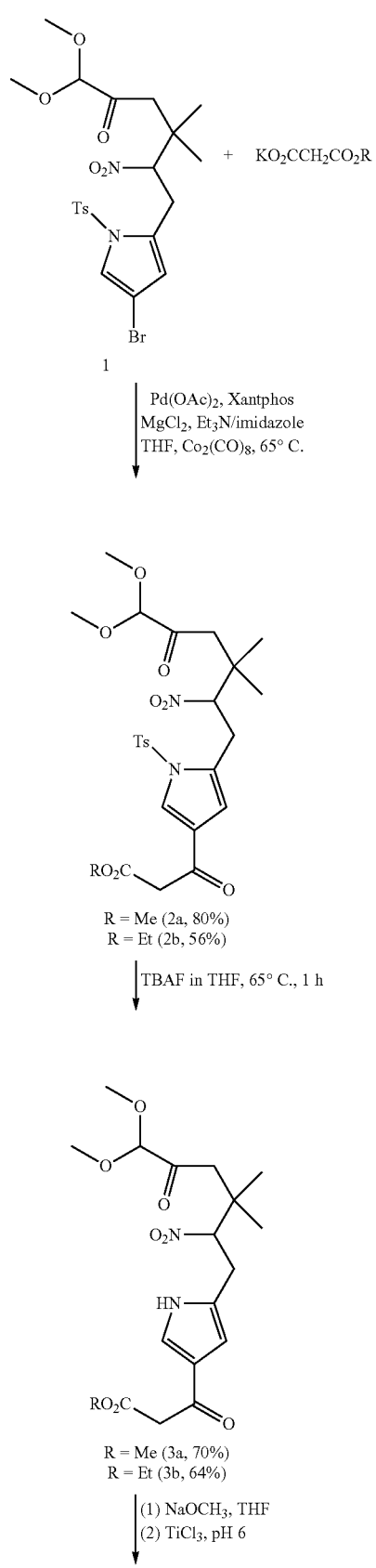

Scheme 5. Preparation of BC Halves

II. Synthesis. 1. AD and BC Halves.

The synthesis of the BC halves began with the known N-tosyl protected bromopyrrole 1.[25] Following a reported procedure[26] with modification to use cobalt carbonyl as a source of carbon monoxide, carbonylation of 1 with a potassium monoalkyl malonate gave the densely functionalized methyl β-ketoester 2a in 80% yield and the ethyl β-ketoester 2b in 56% yield (Scheme 5). We were pleased to find that this Pd-catalyzed carbonylation could be carried on a bromopyrrole, although more than a catalytic amount of Pd(OAc)$_2$ (0.5 molar equivalent) and a longer reaction time (48 h) were required for completion of the reaction. The remainder of the synthesis followed established procedures for dihydrodipyrrins lacking the β-ketoester.[25] Cleavage of the tosyl group by refluxing in THF containing tetra-n-butylammonium fluoride (TBAF) gave the free pyrrole 3a or 3b in 70% or 64% yield, respectively. Each of the latter was treated with NaOMe followed by a buffered solution of TiCl$_3$ at room temperature for 16 h to afford BC half 4a or 4b in 45% or 36% yield. Both BC halves were readily prepared in 200-mg quantity.

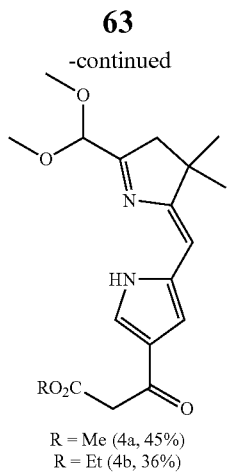

R = Me (4a, 45%)
R = Et (4b, 36%)

Four AD halves were sought (Chart 3). The synthesis of AD halves is established,[4,5] generally begins with the desired n-substituted pyrrole, and proceeds via the corresponding pyrrole-2-carboxaldehyde. For the case where the pyrrole bears two electron-releasing substituents at the β-positions (e.g., 5-MeMe), a stabilizing ester substituent at the 5-position is required. AD halves 5-T and 5-MeMe are known compounds,[5] whereas 5-Ar and 5-EtEs are prepared herein.

Chart 3. Target AD Halves

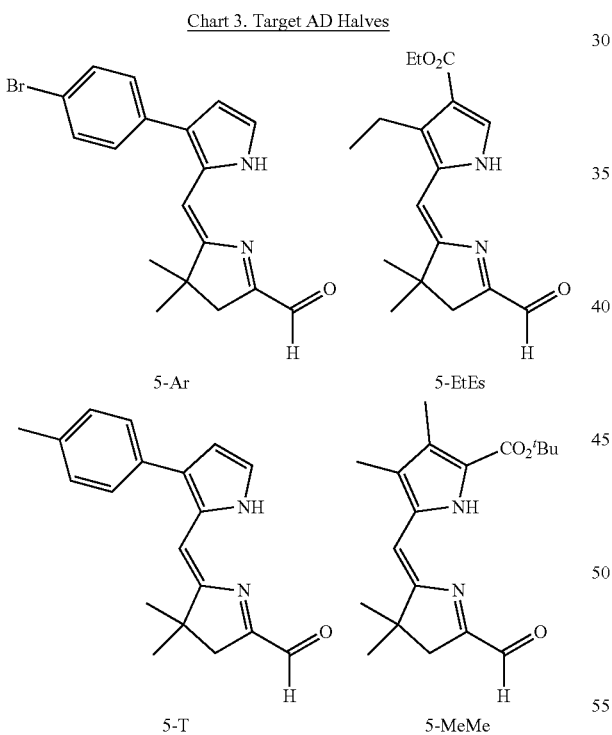

5-Ar
5-EtEs
5-T
5-MeMe

The synthesis of 5-Ar proceeds in well practiced fashion[4] as is shown in Scheme 6. Wittig reaction of p-bromobenzaldehyde with (carbethoxymethylene)triphenylphosphorane afforded cinnamate 6, which upon van Leusen reaction with TosMIC and subsequent saponification and decarboxylation gave the 3-arylpyrrole 7. Vilsmeier formylation of the latter gave regioselectively the 2-formylpyrrole 8 in 77% yield. Conversion to the 2-(2-nitroethyl) derivative 9-Ar proceeded via Henry reaction with nitromethane and subsequent reduction with NaBH₄.

Scheme 6. Precursors of an AD Half

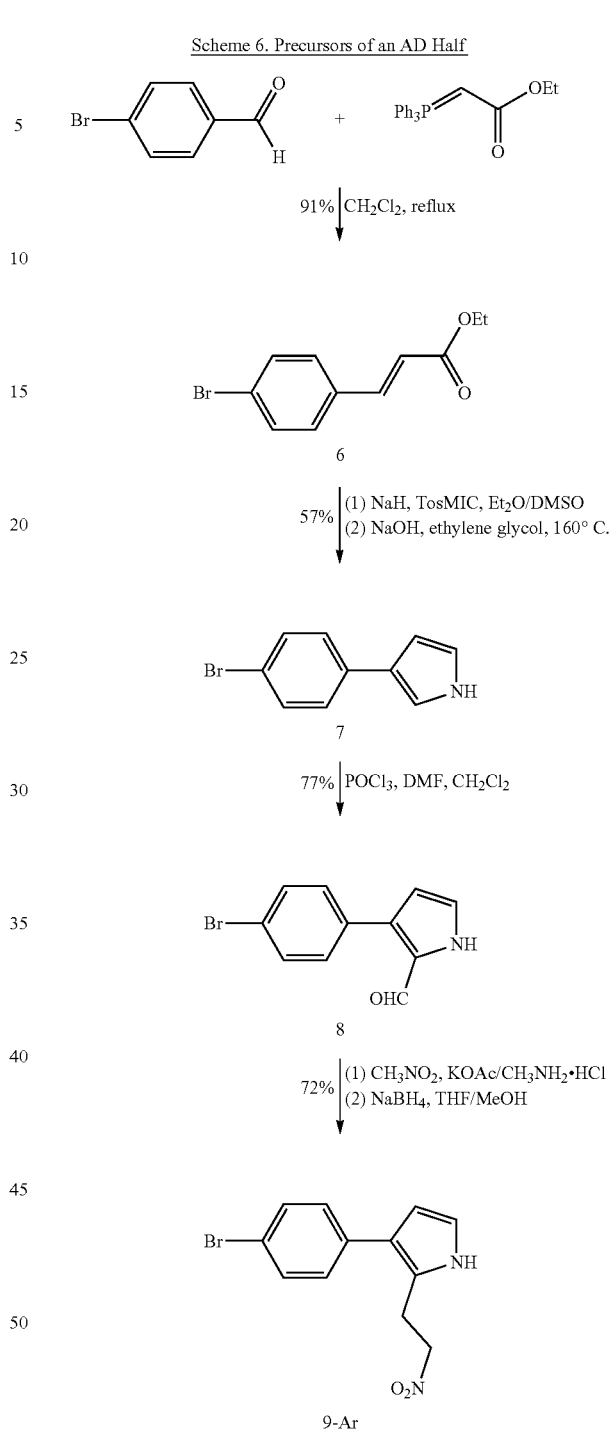

The completion of the AD half syntheses is shown in Scheme 7. The key steps involve (i) Michael addition between 2-(2-nitroethyl)pyrroles (9-Ar, 9-EtEs) and mesityl oxide to form the nitrohexanone-pyrroles (10-Ar, 10-EtEs); (ii) reductive ring closure to give the 1-methyldihydrodipyrrins (11-Ar, 11-EtEs), and (iii) SeO₂ oxidation to convert the 1-methyl group to the 1-formyl group and afford the desired dihydrodipyrrin-carboxaldehydes (5-Ar, 5-EtEs). The dihydrodipyrrin-carboxaldehydes generally are unstable to acidic conditions and should be prepared immediately prior to use.

Scheme 7. Synthesis of AD Halves

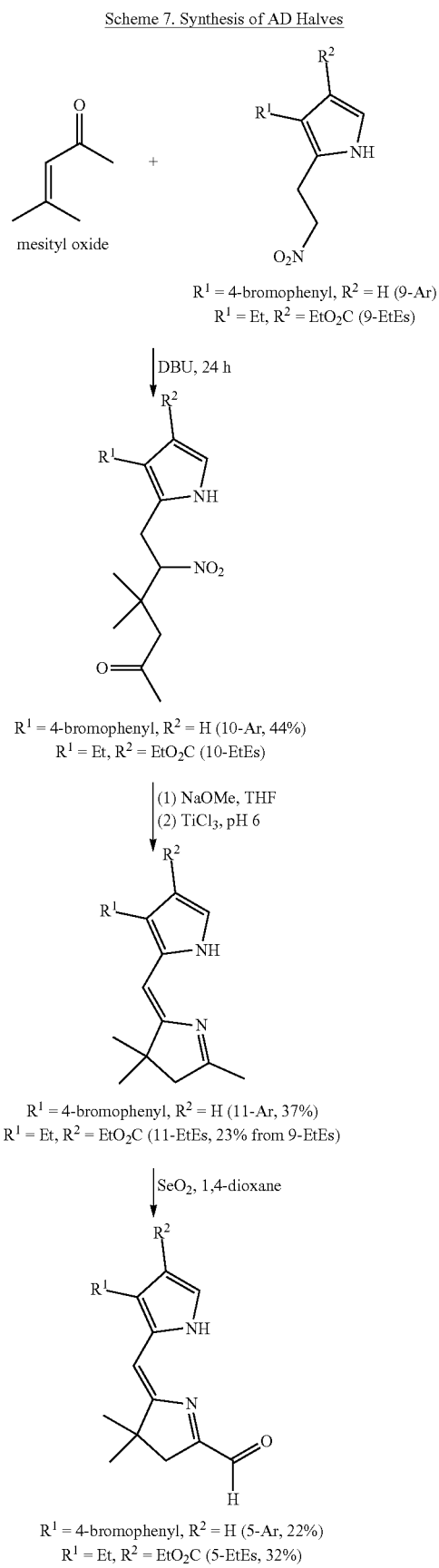

2. Conditions for Bacteriochlorin Formation.

The formation of the bacteriochlorin entails a two-step approach as illustrated for reactants 5-T and 4a in Scheme 8. First, the directed Knoevenagel condensation of 5-T and 4a gave the corresponding α,β-unsaturated ketone 12-T (a bilin analogue). After a few attempts, a catalytic amount of piperidine and acetic acid in $CH_2Cl_2$ in the presence of molecular sieves (3 Å powder) for 16 h was found to produce the target 12-T in 63% yield. Both the α-unsubstituted pyrrole and the acetal group survived the reaction conditions. The linear intermediate 12-T was obtained following chromatography as a dark red oil. $^1$H NMR spectroscopy of 12-T gave two peaks (δ 7.65 and 7.39 ppm) characteristic of the α-olefinic proton and the α-pyrrolic proton. We know of no other molecules resembling 12-T for spectroscopic comparisons; perhaps the closest would be a 10-oxobiladiene-ac[27] yet 12-T is a vinylogous relative and also contains two pyrroline rings.

Scheme 8. De novo Route to Analogues of the Bacteriochlorophyll Ligand

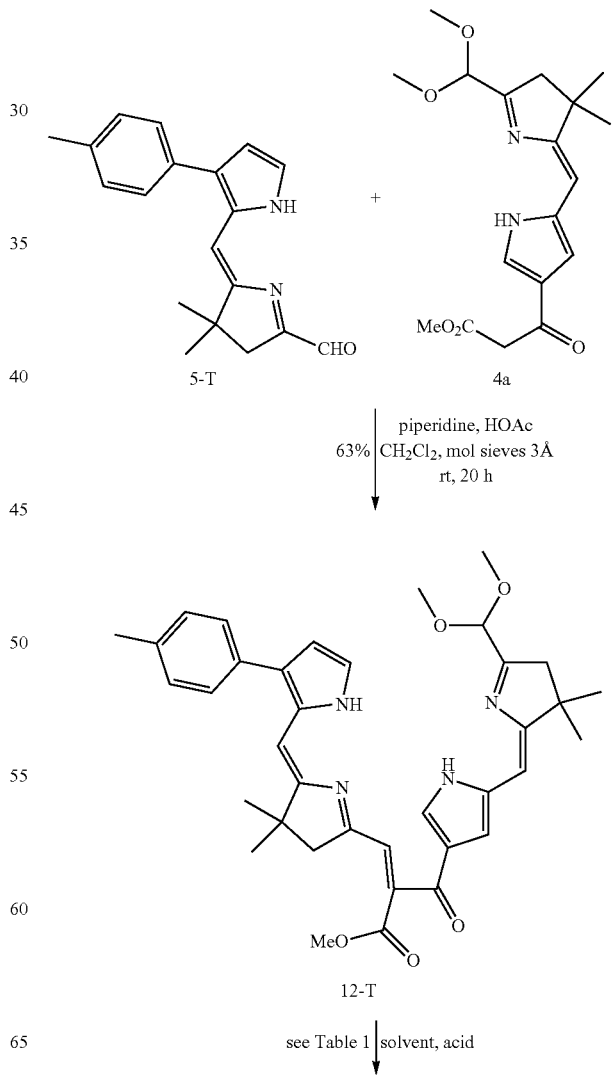

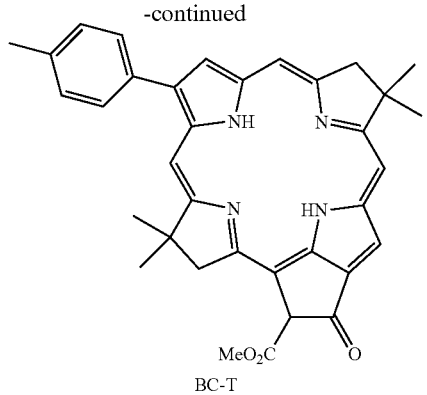

BC-T

In the second step, bacteriochlorin formation requires (i) electrophilic reaction between the acetal group and the α-pyrrole position, and (ii) intramolecular Nazarov reaction of the α,β-unsaturated ketone with the adjoining α-pyrrole position. In this regard, acid catalysis is expected to promote both reactions. Several considerations are germane: (1) the previous work by Frontier and co-workers indicated that Sc(OTf)$_3$, In(OTf)$_3$ and Hf(OTf)$_4$ are more effective catalysts in the Nazarov cyclization.[22] (2) Our previous studies on the self-condensation of dihydrodipyrrin-acetals identified Lewis acids suitable for the condensation between pyrrole and acetal units (e.g., BF$_3$·OEt$_2$ in CH$_3$CN,[3] TMSOTf/DTBP in CH$_2$Cl$_2$[4]). (3) Yb(OTf)$_3$ and Sc(OTf)$_3$ were especially efficient in catalyzing pyrrole-acetal condensations, although tetradehydrocorrin-type macrocycles were obtained rather than bacteriochlorins.[16,28]

Six acids were examined for the double ring closure of 12-T (Table 1, entries 1-6). The reaction was conducted with 0.2 mM 12-T and 2 mM acid with the indicated solvent or temperature. The reactions were followed by UV-Vis absorption spectroscopy, and typically were complete in 20 h. The yield was calculated using the molar absorption coefficient for BC-T of 5.0×10$^4$ M$^{-1}$ cm$^{-1}$ at the Q$_y$ band ($\lambda_{Qy}$=722 nm in toluene). Among the acids examined, Hf(OTf)$_4$ (entry 2), TMSOTf/DTBP (entry 5) or BF$_3$·OEt$_2$ (entry 6), which are all effective catalysts in the de novo synthesis strategy, did not afford a peak characteristic of bacteriochlorins. On the other hand, Sc(OTf)$_3$ and Yb(OTf)$_3$ gave BC-T in 10% yield (entry 1) and 14% yield (entry 4), respectively. With In(OTf)$_3$, the corresponding indium bacteriochlorin ($\zeta_{Qy}$=746 nm in toluene) was produced instead of the free base bacteriochlorin (entry 3).

All the condensations were carried out in dilute solution (0.2 mM of reagent) to avoid intermolecular side-reactions. Reactions at a higher concentration (10 mM) led to only a trace amount of an unknown bacteriochlorin ($\lambda_{Qy}$=743 nm in toluene), which may result from the self-condensation of bilin 12-T.

The effect of temperature and solvent on bacteriochlorin formation was examined with Yb(OTf)$_3$ as catalyst. The yield of bacteriochlorin increased with increased reaction temperature in 1,2-dichloroethane (entries 7-10), reaching 80° C. Maintaining the temperature at 80° C., no bacteriochlorin was obtained in nitromethane (entry 11) while the yield was very low in toluene (5.6%, entry 12). The reaction proceeded efficiently in acetonitrile at 80° C. (46%, entry 13) and moderately well in dichloromethane at 40° C. (13%, entry 14).

Frontier and co-workers[22] identified added LiClO$_4$ as an effective catalyst for the Nazarov cyclization. Here, reaction in the presence of 10 equiv of LiClO$_4$ did not affect the yield, whereas excess LiClO$_4$ (100 equiv) led to a lower yield. In summary, the reaction of 12-T in dilute solution with Yb(OTf)$_3$ in acetonitrile at 80° C. gave the best results for bacteriochlorin formation.

TABLE 1

Conditions for Bacteriochlorin (BC-T) Formation from 12-T

| Entry | Lewis acid | Solvent$^a$ | Temperature | Yield (%)$^b$ |
|---|---|---|---|---|
| 1 | Sc(OTf)$_3$ | DCE | 50 | 9.6 |
| 2 | Hf(OTf)$_4$ | DCE | 50 | 0$^c$ |
| 3 | In(OTf)$_3$ | DCE | 50 | 7.6$^d$ |
| 4 | Yb(OTf)$_3$ | DCE | 50 | 14 |
| 5 | TMSOTf/DTBP | CH$_2$Cl$_2$ | 20 | 0$^c$ |
| 6 | BF$_3$·OEt$_2$ | CH$_3$CN | 20 | —$^e$ |
| 7 | Yb(OTf)$_3$ | DCE | 20 | 13 |
| 8 | Yb(OTf)$_3$ | DCE | 35 | 14 |
| 9 | Yb(OTf)$_3$ | DCE | 65 | 16 |
| 10 | Yb(OTf)$_3$ | DCE | 80 | 20 |
| 11 | Yb(OTf)$_3$ | CH$_3$NO$_2$ | 80 | 0$^c$ |
| 12 | Yb(OTf)$_3$ | Toluene | 80 | 5.6 |
| 13 | Yb(OTf)$_3$ | CH$_3$CN | 80 | 46 |
| 14 | Yb(OTf)$_3$ | CH$_2$Cl$_2$ | 40 | 13 |

$^a$DCE = dichloroethane.
$^b$Yields were determined on the basis of the absorption spectrum.
$^c$No absorption peak was detected >700 nm.
$^d$Yield of the corresponding indium bacteriochlorin.
$^e$The desired bacteriochlorin ($\lambda_{Qy}$ = 722 nm) was not detected. A trace amount of unknown bacteriochlorin ($\lambda_{Qy}$ = 750 nm) was observed with a yield <2%.

3. Scope of Reaction. The reaction using the refined catalysis conditions was carried out with 20 mg of the linear bilin 12-T, and the resulting bacteriochlorin was purified by chromatography. To our delight, the yield of isolated bacteriochlorin BC-T reached 56% (9.5 mg). Other bilins of type 12 were prepared by reaction with various AD halves and BC half 4a or 4b in the same manner as for bilin 12-T (Table 2). BC halves 4a and 4b differ only in the nature of the alkyl ester (methyl, ethyl). The Knoevenagel reaction was carried out with 1-1.5 equiv of the dihydrodipyrrin-carboxaldehyde (AD half, 5) relative to the BC half (4a, 4b), whereupon the bilins (12) were obtained in yields ranging from 57-71%.

TABLE 2

Investigation of the Scope of Bacteriochlorin Formation

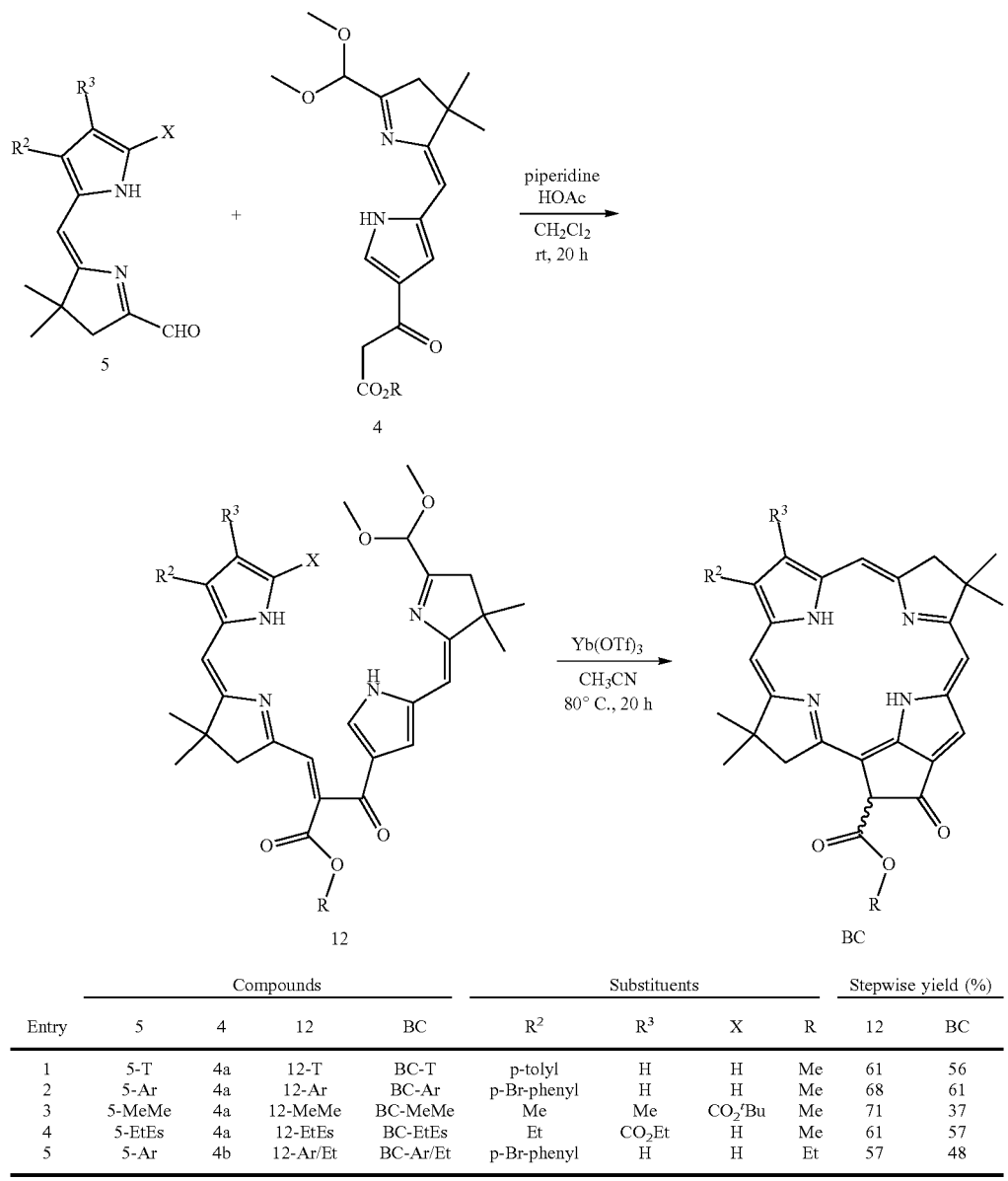

| | Compounds | | | | Substituents | | | | Stepwise yield (%) | |
|---|---|---|---|---|---|---|---|---|---|---|
| Entry | 5 | 4 | 12 | BC | $R^2$ | $R^3$ | X | R | 12 | BC |
| 1 | 5-T | 4a | 12-T | BC-T | p-tolyl | H | H | Me | 61 | 56 |
| 2 | 5-Ar | 4a | 12-Ar | BC-Ar | p-Br-phenyl | H | H | Me | 68 | 61 |
| 3 | 5-MeMe | 4a | 12-MeMe | BC-MeMe | Me | Me | $CO_2{}^tBu$ | Me | 71 | 37 |
| 4 | 5-EtEs | 4a | 12-EtEs | BC-EtEs | Et | $CO_2Et$ | H | Me | 61 | 57 |
| 5 | 5-Ar | 4b | 12-Ar/Et | BC-Ar/Et | p-Br-phenyl | H | H | Et | 57 | 48 |

With the bilins 12 in hand, conversion to the bacteriochlorins was pursued by application of the refined reaction conditions. First, the reaction conditions are compatible with a bromoaryl substituent to give BC-Ar (61% yield, entry 1). Second, a bacteriochlorin (BC-MeMe) with two electron-donating groups was obtained in 37% yield. In addition to the pyrrole-acetal condensation and Nazarov cyclization, cleavage of the tert-butyl ester occurred in this process, resulting in a relative lower yield compared with the other examples. The presence of the tert-butyl ester was essential to stabilize the very electron-rich dihydrodipyrrin unit.[5] Third, a bacteriochlorin (BC-EtEs) with an electron-withdrawing group at the β-pyrrole position (—$CO_2Me$) was prepared in good yield (57%). Finally, starting with BC half 4b, a bacteriochlorin with a $13^2$-ethoxycarbonyl group (BC-Ar/Et) was obtained, indicating the possibility of more elaborate modification of this macrocyclic skeleton.

III. Characterization. 1. Structures.

All new bacteriochlorins were characterized by $^1H$ NMR and $^{13}C$ NMR spectroscopy, high-resolution mass spectrometry, and static absorption and fluorescence spectroscopy. In general, the $^1H$ NMR spectra of the bacteriochlorins were complex due to the non-equivalent A, B, C and D rings as well as the presence of the additional E ring. The $^1H$ NMR spectrum of BC-MeMe is illustrative in showing the following features: (1) Four singlets in the region δ 7.62-7.97 ppm stem from the four distinct protons on the macrocycle (meso-protons at the 5-, 10-, and 20-positions, and one 3-pyrrolic proton) around the perimeter of the bacteriochlorin. (2) The proton at the $13^2$-position (ring E) resonates as a singlet at δ 5.64 ppm, which is comparable to that of the $13^2$-H in bacteriopheophytin a (δ 6.08 ppm[29]). (3) The presence of a stereocenter at the $13^2$-position causes the pyrroline $CH_2$ protons (ring D, position 17: δ 3.62-3.74 ppm) flanking ring E to be split into an AB pattern, while the pyrroline $CH_2$ groups distal to the stereocenter resonate as an apparent singlet (ring B, position 7: δ 3.97 ppm). Also, the protons of the geminal dimethyl groups at the 18-position are split into two singlets. (4) Two broad upfield peaks (1.16 and 1.62 ppm) are attributed to the N—H protons. No peaks upfield of 0 ppm were observed.

Comparing the $^1$H NMR spectra of BC-MeMe, BC-EtEs and bacteriopheophytin a[29] yields the following observations: (1) The chemical shifts of the peripheral protons of BC-MeMe (with two electron-donating groups) are in the range of 7.63-7.97 ppm, while those of BC-EtEs (with one electron-withdrawing group) are in the range of 8.20-9.16 ppm; the latter are more similar to those of bacteriopheophytin a (8.39-8.96 ppm). (2) The N—H protons in BC-EtEs resonate at −0.07 and 1.59 ppm, compared to those in BC-MeMe (δ 1.16, 1.62 ppm) and bacteriopheophytin a (δ −0.99, 0.44 ppm).

2. Absorption and Fluorescence Spectra.

The spectral data shown in Table 3 include the position and the relative intensity of the characteristic absorption bands, the full-width at half-maximum (fwhm) value of the long-wavelength absorption band ($Q_y$), and the ratio of the intensity of the $Q_y$ to $B_y$ band ($I_{Qy}/I_{By}$ ratio). For comparison, the table also includes spectral data for bacteriopheophytin a (BPheo a)[30] and the benchmark $Me_4$-BC. The molar absorption coefficient of BC-T in toluene was determined (using ~6 mg of BC-T) to be $5.0 \times 10^4$ $M^{-1}cm^{-1}$, which is close to that reported for bacteriopheophytin a (42-49 $mM^{-1}$ $cm^{-1}$ in acetone-methanol (7:2, v/v) and 63-73 $mM^{-1}$ $cm^{-1}$ in ether).[31]

The spectrum of each bacteriochlorin contains three main absorption bands termed the B band (a mixture of $B_x$ and $B_y$ transitions), $Q_x$ band and $Q_y$ band.[2] The spectral features resemble those of bacteriopheophytin, but differ to some degree from those of bacteriochlorins lacking the isocyclic ring. In comparison with the 2,3,12,13-tetramethylbacteriochlorin ($Me_4$-BC, Chart 4), which lacks the isocyclic ring, the following features are noteworthy: (1) The $I_{Qy}/I_{By}$ ratio is much lower (0.38-0.62 vs. 0.97), indicating a relatively lower intensity of the $Q_y$ band. (2) The $I_{Qy(0,0)}/I_{Qx(0,0)}$ ratio is much lower (1.1-2.0 vs. 5.3), indicating a relatively greater intensity of the $Q_x$ band. (3) The $I_{Qx(0,0)}/I_{Qx(1,0)}$ ratio also is greater (3.1-4.1 vs. 1.9). (4) The fwhm of the $Q_y(0,0)$ band is in the range of 27-33 nm, which is slightly broader than reported for (non-annulated) bacteriochlorins (11-25 nm).[30]

Chart 4. A Benchmark Bacteriochlorin

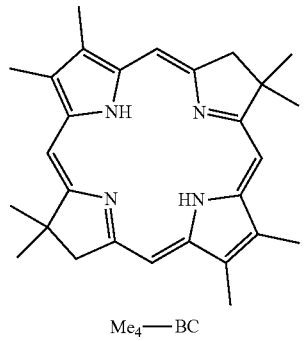

$Me_4$—BC

The fluorescence emission spectra of four annulated bacteriochlorins (BC-MeMe, BC-T, BC-Ar, and BC-EtEs) were recorded in toluene at room temperature. In each case, the $Q_y(0,0)$ emission band is shifted 6-15 nm to longer wavelength than the $Q_y(0,0)$ absorption band, to be compared with a Stokes shift for $Me_4$-BC of ~2 nm. The comparatively large Stokes shift of the annulated bacteriochlorins indicates more substantial changes in structure or interaction with the solvent upon photoexcitation. The fwhm of $Q_y(0,0)$ emission band is in the range of 26-32 nm.

TABLE 3

Spectral Characteristics of Bacteriochlorins[a]

| | Absorption in nm (relative intensity[b]) | | | | | Flu | Fwhm (nm) | | Intensity ratios | | |
|---|---|---|---|---|---|---|---|---|---|---|---|
| | | | | | | $Q_y$ (0, 0) | $Q_y$ (0, 0) | | | $I_{Qx(0,0)}/$ | $I_{Qy(0,0)}/$ |
| Compound | B (0, 0)[c] | $Q_x$ (1, 0) | $Q_x$ (0, 0) | $Q_y$ (1, 0) | $Q_y$ (0, 0) | in nm | abs | $Q_y$ em | $I_{Qy}/I_B$ | $I_{Qx(1,0)}$ | $I_{Qx(0,0)}$ |
| BC-T | 356 | 489 | 520 | 660 | 721 | 736 | 29 | 26 | 0.55 | 3.4 | 1.6 |
| | (1.8) | (0.18) | (0.62) | (0.31) | (1.0) | | | | | | |
| BC-Ar | 356 | 490 | 521 | 664 | 727 | 737 | 27 | 29 | 0.62 | 3.8 | 1.9 |
| | (1.6) | (0.14) | (0.54) | (0.25) | (1.0) | | | | | | |
| BC-MeMe | 351 | 480 | 511 | 640 | 696 | 707 | 29 | 31 | 0.38 | 3.1 | 1.1 |
| | (2.6) | (0.28) | (0.87) | (0.45) | (1.0) | | | | | | |
| BC-EtEs | 357 | 501 | 533 | 680 | 745 | 751 | 33 | 32 | 0.58 | 3.8 | 1.9 |
| | (1.7) | (0.14) | (0.53) | (0.21) | (1.0) | | | | | | |
| BC-Ar/Et | 357 | 490 | 521 | 665 | 728 | 737 | 28 | 28 | 0.62 | 4.1 | 1.9 |
| | (1.6) | (0.13) | (0.53) | (0.24) | (1.0) | | | | | | |
| BPheo a[d] | 356 | 492 | 524 | 681 | 749 | 768[e] | 31 | 27[e] | 0.63 | 4.6 | 2.0 |
| | (1.6) | (0.11) | (0.51) | (0.18) | (1.0) | | | | | | |
| $Me_4$-BC[f] | 346, 374 | 462 | 490 | 685 | 721 | 723 | 11.9 | 15.5 | 0.97 | 1.9 | 5.3 |
| | (1.0, 1.1) | (0.10) | (0.19) | (0.10) | (1.0) | | | | | | |

[a]Obtained in toluene at room temperature.
[b]Relative intensity of the indicated peak versus that of the $Q_y$ (0, 0) band.
[c]Mixture of the $B_x$ (0, 0) and $B_y$ (0, 0) absorption bands.
[d]Absorption data (in diethyl ether) from reference 32.
[e]Fluorescence data (in toluene) from reference 30.
[f]Data from reference 5.

Discussion

The route described herein constitutes a new approach for macrocycle construction that concomitantly forms the isocyclic ring, while maintaining a gem-dimethyl group in each pyrroline ring. The gem-dimethyl motif secures the macrocycle from adventitious dehydrogenation processes that are likely in an aerobic environment. In this section, we first compare methods for installation of the isocyclic ring. We then describe features (including stereochemistry) of the Nazarov cyclization in the context of the new route to bacteriochlorins, followed by a side-by-side evaluation of the two de novo routes to bacteriochlorins from the dihydrodipyrrin halves.

Installation of the Isocycic Ring.

A handful of approaches for installation of a fifth ring spanning positions 13 and 15 has been developed over the years (Scheme 9). Fischer dehydrated (hydroxymethylcarbonyl)porphyrin A in conc. $H_2SO_4$ to give the porphyrin bearing the isocyclic ring (B).[33] Lash condensed dipyrromethane $C^1$ and dipyrromethane $C^2$ bearing an annulated oxocyclopentanyl ring[34] to form D (which lacks the $13^1$-oxo group).[35] Both B and D are porphyrins. Fischer also converted chlorin e6 trimethyl ester (E) via Dieckmann cyclization to methyl pheophorbide a (F),[36,37] a chlorin degradation product of chlorophyll a. Smith extended Kenner's thallium-photochemical route[38-41] for conversion of the β-ketoester-substituted chlorin G to methyl pheophorbide a (F).[42] A more recent method entails 15-bromination and Pd-mediated α-arylation (Scheme 2), which has been applied to gem-dimethyl stabilized chlorins and bacteriochlorins but requires bromination of the macrocycle, and lacks provisions for incorporation of the $13^2$-carboalkoxy group.[43-46] To our knowledge, no methods other than those shown in Schemes 2 and 9 have been developed previously for use with bacteriochlorins. The formation of the isocyclic ring concomitantly with macrocycle construction affords considerable simplicity, and does so while enabling distinct substituents in the two halves of the bacteriochlorin.

Scheme 9. Routes for Installation of the Isocyclic Ring porphyrins

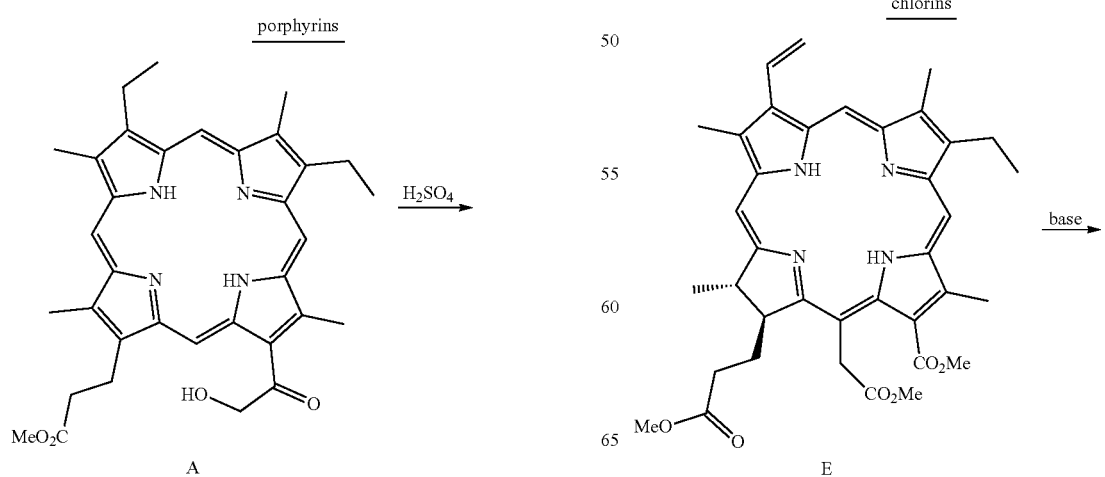

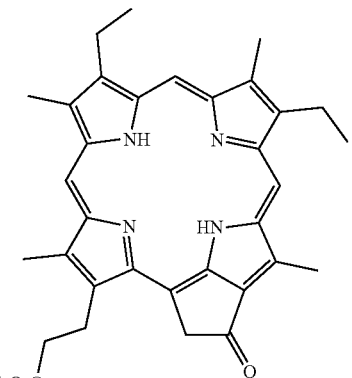

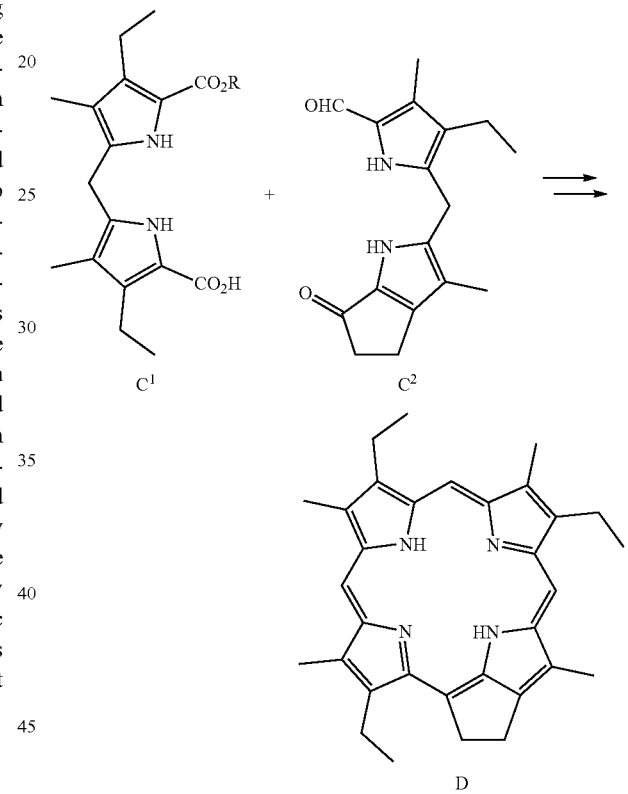

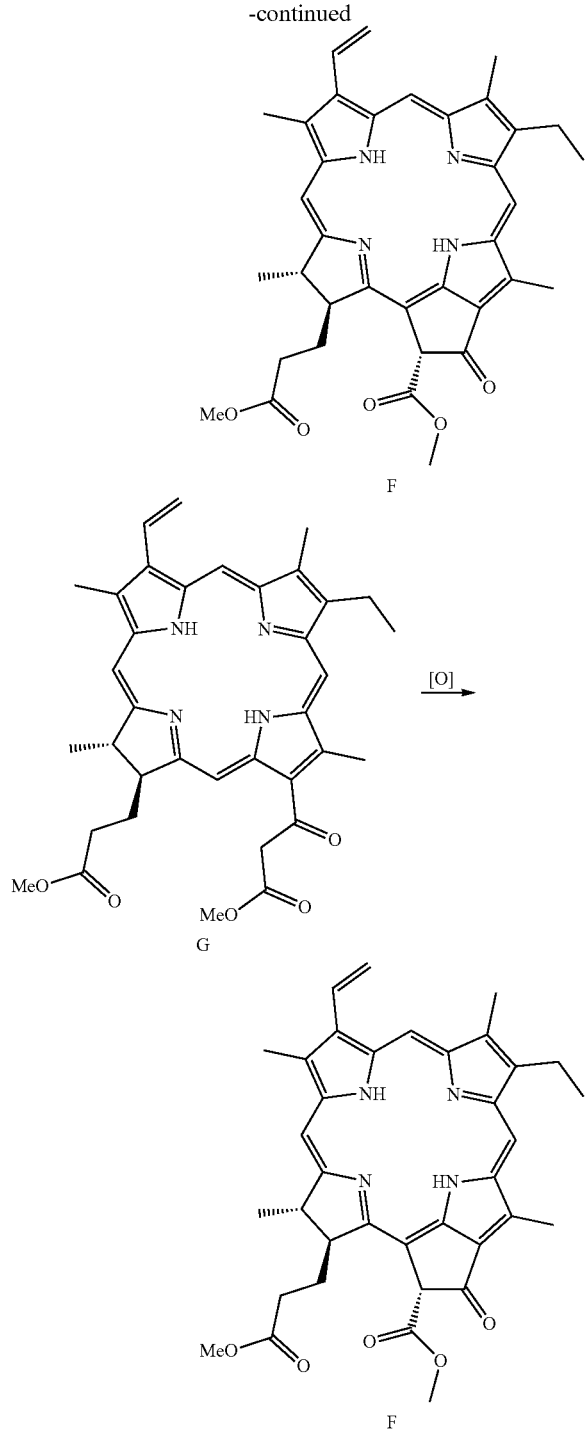

F

G

F

Features of the Nazarov Cyclization.

The key step in the reaction process is Nazarov cyclization, a classical synthetic method for producing a cyclic ketone.[20] While applied with a variety of heteroaromatic substrates, in 2006 Knight and co-workers reported the first example of Nazarov cyclization involving a pyrrole.[21] The reaction was carried out with α-acyl N-tosylpyrroles in the presence of trifluoroacetic anhydride. Frontier and co-workers followed immediately with examples of both α-acylpyrroles and β-acylpyrroles in the absence of any N-protection.[22] The reaction with a catalytic amount of Sc(OTf)$_3$ (10 mol %) in the presence of LiClO$_4$ afforded ring closure in good yield (eq 1). Since then other methods for Nazarov cyclization of pyrroles have been reported, including using an iron(III) salt[23] or dicationic Ir(III) complex[24] for catalysis. The reaction process also can be regarded as an intramolecular Michael addition (5-endo-trig)[47] of the pyrrole with the α,β-unsaturated ketone. Intermolecular examples of such pyrrole C-alkylations date to as early as 1951 and were typically carried out with either activated reactants or somewhat forcing conditions,[48-55] but have received considerable attention in the past 15 years upon extension to unactivated reactants and implementation with mild Lewis acid catalysts[56-73] and/or enantioselective catalysts[74-82] (for a partial review, see reference 83).

The Nazarov cyclization is regarded to proceed via a 4π-electrocyclization of a pentadienyl cation derived from a divinylketone species;[20] here, the pyrrole moiety provides one of the "vinyl" units. The resulting conrotatory ring closure creates two stereocenters. Here, one of the stereocenters is lost upon elimination leading to the aromatic, 18π-electron bacteriochlorin chromophore. The remaining stereocenter is at the 13$^2$-position, whereupon the resulting bacteriochlorin is racemic. The carboalkoxy group at the 13$^2$-position in (bacterio)chlorophylls is susceptible to epimerization given the presence of the β-keto group.[13,14] While the trans-configuration (13$^2$-relative to the 17-position) is typically more stable, macrocycles with the cis-configuration of the two groups have been considered as possible minority pigments in selected photosynthetic systems.[84] The mole fraction of the cis-isomer was found to range from 0.12-0.25 over a set of 8 chlorophylls, bacteriochlorophylls and analogues.[85] Thus, the natural tetrapyrroles bearing an isocyclic ring often exist as diastereomeric mixtures owing to unavoidable epimerization of the 13$^2$-carbomethoxy group. Thus, while the synthetic bacteriochlorins obtained herein are racemic, even an asymmetric synthesis is likely to yield products that spontaneously racemize owing to the intrinsic features of the β-ketoester.

Comparison of Routes.

The Eastern-Western (or Northern-Southern) route to bacteriochlorins is concise, but installation of the isocyclic ring requires 15-bromination followed by Pd-mediated annulation. Even then, the ring E lacks the 13$^2$-carbomethoxy group. The synthesis of unsymmetrical annulated bacteriochlorins described herein entails preparation of BC and AD components, joining of these two halves to form a bilin intermediate under conditions wherein neither half undergoes self-condensation leading to a symmetrical bacteriochlorin, and acid-catalyzed conversion of the bilin intermediate to form the macrocycle. Use of the pyrrole-acetal condensation and the Nazarov cyclization creates the bacteriochlorin macrocycle along with the ring E in a one-flask transformation. In this manner, a Pd-mediated coupling (i.e., conversion of 1 to 2a, 2b; Scheme 5) is still required (attachment of the β-ketoester to the pyrrole of the BC half), but bromination of the bacteriochlorin is not required. Hence, halogens can be installed on the AD half for subsequent exploitation following formation of the macrocycle.

A direct comparison of the two routes for constructing the bacteriochlorin macrocycle is provided in Scheme 10. The self-condensation of two dihydrodipyrrin-acetal molecules (II-acetal) results in successive elimination of two molecules of methanol, whereupon a 5,15-dihydro-5,15-dimethoxybacteriochlorin (X) is obtained. Elimination of a third molecule of methanol affords the 5-methoxybacteriochlorin (XI).[86] The presence of the 5-methoxy group provides a convenient directive entity for 15-bromination,[87] but in other instances is undesired. By contrast, the reaction of AD (VII) and BC (VIII) halves can be envisaged as proceeding through a product of Knoevenagel condensation and Nazarov cyclization (XII). Subsequent cyclization and elimination of one molecule of methanol affords the 5,15-dihydro-5-methoxybacteriochlorin (XIII). Elimination of the second molecule of methanol aromatizes the macrocycle and affords the bacteriochlorin V. The difference in substitution patterns of V versus XI originates early in the reaction process: there are two carbon-carbon bonds formed upon Knoevenagel condensation and Nazarov cyclization (giving XII) versus only one upon electrophilic aromatic substitution (giving IX). Side-by-side comparison of intermediates X (5,15-dimethoxy) and XIII (5-methoxy) illustrates that while aromatization is likely similar in the two syntheses, requisite elimination of only one molecule of methanol leaves one methoxy group remaining in XI, whereas none is left in the ring-E containing bacteriochlorin V.

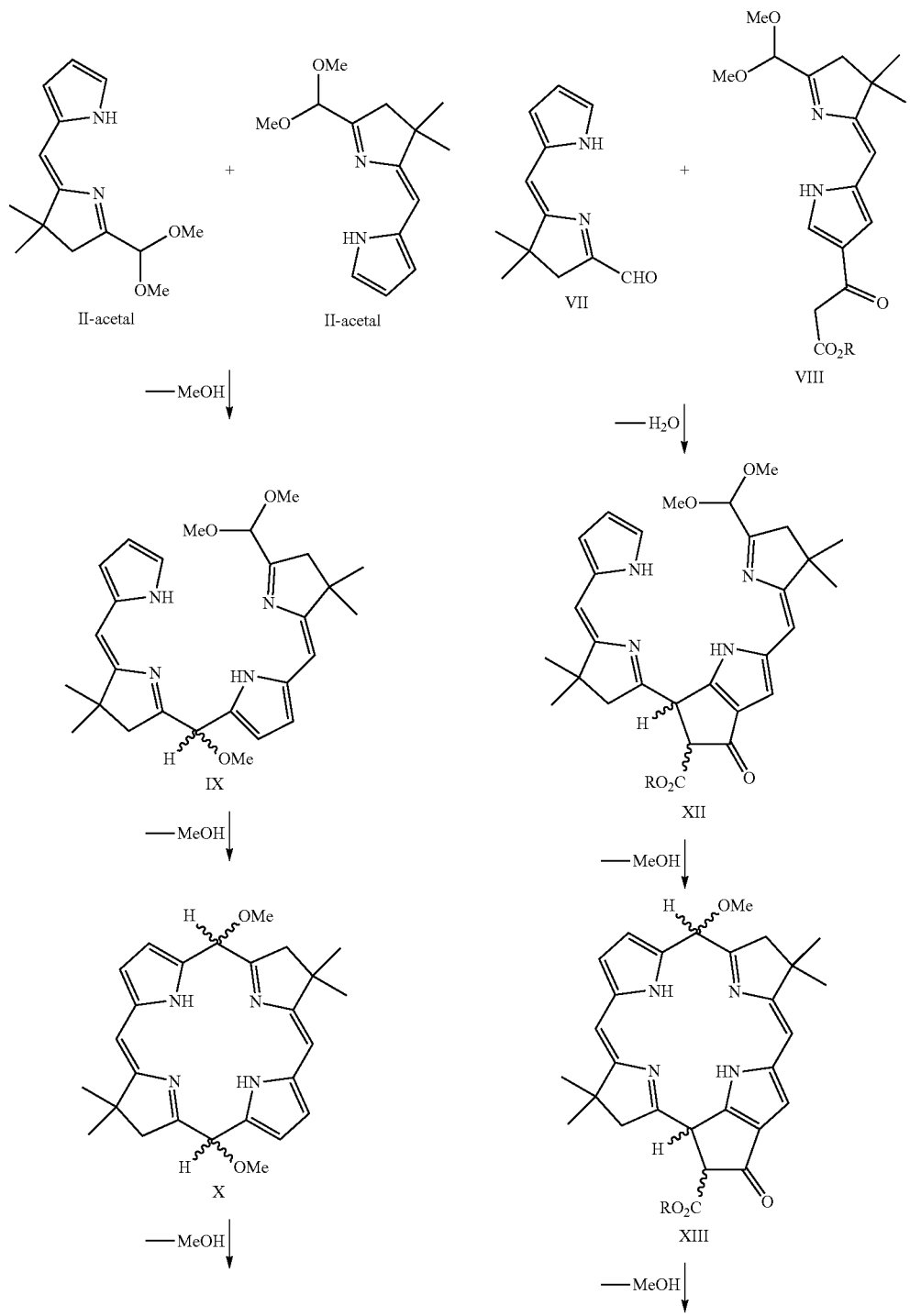

Scheme 10. Comparison of Bacteriochlorin Syntheses

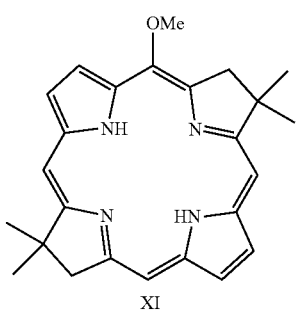

XI

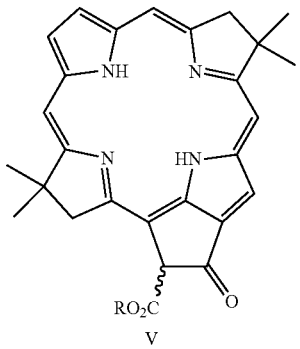

V

Synthetic Attributes.

There are now four distinct routes for de novo construction of the bacteriochlorin chromophore (excluding derivatization of porphyrins or chlorins). The routes include (1) the Kishi synthesis of tolyporphin A diacetate and analogues;[9-11] (2) the Eastern-Western synthesis shown in Scheme 1 (provided in the Background section of the present application); (3) a Northern-Southern instantiation of the route Eastern-Western route;[7] and (4) the route described herein. Only the latter enables simultaneous construction of the macrocycle and the isocyclic ring. The utility of a general route to bacteriochlorins with distinct substituents in the various A-D rings is outlined in the Introduction. Because the present route should enable such capabilities yet also constructs ring E, further applications and extensions can be envisaged, of which five are described here.

First, the preparation of bacteriochlorins with progressive extent of substitution ranging from the fully unsubstituted to the fully decorated analogue of Bpheo a is essential for understanding the molecular origins of bacteriochlorophyll photophysics.[5] The present route appears ideal for preparing more elaborate analogues along this progression.

Second, the Nazarov cyclization is compatible with other heterocycles,[20] hence core-modified ring-C analogues should be accessible.

Third, the new route might enable synthetic access to the natural macrocycles themselves. The synthesis of chlorophylls would require one enantiopure dipyrrin and one dipyrromethane rather than two dihydrodipyrrins, yet would offer a fundamental alternative to the route devised by Woodward and co-workers.[17-19] The synthesis of bacteriochlorophylls, which has never been reported, would require access to and utilization of two enantiopure dihydrodipyrrins.

Fourth, ring E over the years has been the site of extensive derivatization chemistry, including reactions at each of the sites ($13^1$ oxo, $13^2$ methylene, $13^2$-carboalkoxy) as well as allomerization and splitting of the ring (by scission of the $13^1$-$13^2$ C—C bond).[13,14] While widely exploited with chlorophylls, analogous chemistry with bacteriochlorophylls has been less investigated owing to the lability of the natural macrocycles.[88] The stability of the macrocycles prepared herein should provide an entree into diverse derivatives by reactions in ring E.

Finally, very little is known about the in vivo degradation of bacteriochlorophylls, by contrast with the results from the intensive study of the enzymatic degradation of chlorophylls in senescent plants. Kräutler and co-workers have identified and characterized a variety of "phyllobilin" species such as the red chlorophyll catabolite (RCC) shown in Chart 5.[89-91] The structure of the phyllobilins closely resembles that of the Nazarov intermediate XII shown in Scheme 9. To our knowledge, phyllobilins have not been the target of reported synthetic studies, and hence knowledge of reactivity and photochemical features depends on isolation of species along the slippery slope of enzymatic catabolism. Whether analogous phyllobilins derive from anoxygenic photosynthetic bacteria remains to be determined. For both types of hydroporphyrins, the synthesis of putative intermediates could prove vital.

Chart 5. A Chlorophyll Catabolite

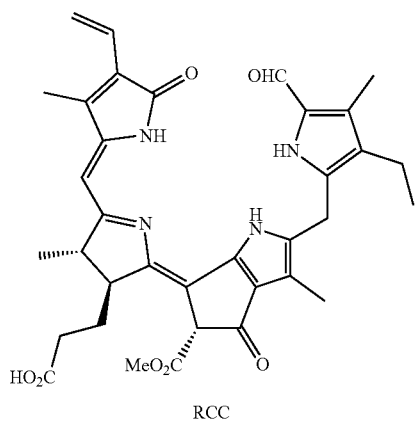

RCC

Experimental Section

General Methods.

$^1$H NMR and $^{13}$C NMR spectra were collected at room temperature in CDCl$_3$ unless noted otherwise. Absorption spectra were obtained in toluene at room temperature unless noted otherwise. Electrospray ionization mass spectrometry (ESI-MS) data are reported for the molecular ion or protonated molecular ion. THF used in all reactions was freshly distilled from Na/benzophenone ketyl. All commercially available compounds were used as received. Non-commercially available compounds including 6-(4-bromo-N-tosylpyrrol-2-yl)-1,1-dimethoxy-4,4-dimethyl-5-nitrohexan-2-one (1)[25] 5-T,[5] 5-MeMe,[5] and 4-ethoxycarbonyl-3-ethyl-2-(2-nitroethyl)pyrrole (9-EtEs)[4] were prepared as described in the literature.

6-[4-(3-Methoxy-3-oxopropanoyl)-N-tosylpyrrol-2-yl]-1,1-dimethoxy-4,4-dimethyl-5-nitrohexan-2-one (2a)

A mixture of compound 1 (1.34 g, 2.50 mmol), methyl potassium malonate (585 mg, 3.80 mmol), Xantphos (725 mg, 1.30 mmol), MgCl$_2$ (357 mg, 3.80 mmol) and imidazole (330 mg, 5.00 mmol) was placed in a 50-mL Schlenk flask and charged with argon. THF (25.0 mL) was added followed with addition of Et$_3$N (520 µL, 3.80 mmol). The mixture was degassed by freeze-pump-thaw cycle. Then, Pd(OAc)$_2$ (280 mg, 1.30 mmol) and Co$_2$(CO)$_8$ (430 mg, 1.30 mmol) was added. The flask was sealed immediately and heated at 65° C. for 48 h and progress was monitored by TLC analysis. If reaction is not completed, Pd(OAc)$_2$ (140 mg, 0.65 mmol) and Co$_2$(CO)$_8$ (215 mg, 0.65 mmol) was added and the reaction was continued for another 24 h. The reaction mixture was diluted with ethyl acetate and filtered through a Celite pad. The filtrate was washed with brine and water, dried (Na$_2$SO$_4$) and concentrated. The crude product was purified by column chromatography (silica, ethyl acetate) to give a light-yellow solid (1.10 g, 80%): mp 138-140° C.; $^1$H NMR (300 MHz) δ 1.14 (s, 3H), 1.23 (s, 3H), 2.45 (s, 3H), 2.57-2.73 (AB, $^2$J=18.6 Hz, 2H), 3.11-3.17 (ABX, $^2$J=16.0 Hz, 1H), 3.35-3.45 (ABX, $^2$J=16.0 Hz, $^3$J=12.3 Hz, 1H), 3.42 (s, 6H), 3.73 (s, 3H), 3.75 (s, 2H), 4.37 (s, 1H), 5.21-5.26 (ABX, $^2$J=12.0 Hz, 3J=2.1 Hz, 1H), 6.42 (d, J=1.5 Hz, 1H), 7.37-7.40 (d, J=8.2 Hz, 2H), 7.70-7.73 (d, J=8.2 Hz, 2H), 7.93 (d, J=1.8 Hz, 1H); $^{13}$C NMR (75 MHz) δ 21.8, 23.8, 24.0, 26.3, 36.4, 44.5, 46.6, 52.5, 55.1, 92.8, 104.7, 112.5, 126.1, 127.1, 128.0, 130.7, 130.9, 134.8, 146.5, 167.5, 186.5, 203.1; ESI-MS obsd 533.1846, calcd 533.1850 [(M+H)$^+$, M=C$_{25}$H$_{32}$N$_2$O$_{10}$S].

6-[4-(3-Ethoxy-3-oxopropanoyl)-N-tosylpyrrol-2-yl]-1,1-dimethoxy-4,4-dimethyl-5-nitrohexan-2-one (2b)

A mixture of 1 (267 mg, 0.500 mmol), ethyl potassium malonate (128 mg, 0.750 mmol), Pd(OAc)$_2$ (56.0 mg, 0.250 mmol), Xantphos (145 mg, 0.250 mmol), MgCl$_2$ (71.4 mg, 0.750 mmol) and imidazole (66.0 mg, 1.00 mmol) was placed in a 10-mL Schlenk tube and charged with argon. THF (4.0 mL) was added followed with addition of Et$_3$N (104 µL, 0.750 mmol) and Co$_2$(CO)$_8$ (86.0 mg, 0.250 mmol). The tube was sealed immediately and heated at 65° C. for 48 h. The reaction mixture was diluted with ethyl acetate and filtered through a Celite pad. The filtrate was washed with brine and water, dried (Na$_2$SO$_4$) and concentrated. The crude product was purified by column chromatography (silica, ethyl acetate) to give a light-yellow oil (160 mg, 56%): $^1$H NMR (400 MHz) δ 1.14 (s, 3H), 1.23 (s, 3H), 1.26 (t, J=7.2 Hz, 3H), 2.46 (s, 3H), 2.57-2.72 (AB, $^2$J=18.8 Hz, 2H), 3.12-3.17 (ABX, $^2$J=16.4 Hz, 1H), 3.35-3.40 (ABX, $^2$J=16.4 Hz, $^2$J=12.4 Hz, 1H), 3.42 (s, 3H), 3.43 (s, 3H), 3.72 (d, J=0.8 Hz, 2H), 4.16-4.22 (q, J=7.2 Hz, 2H), 4.36 (s, 1H), 5.21-5.24 (ABX, $^2$J=12.4 Hz, $^3$J=1.6 Hz, 1H), 6.42 (d, J=2.0 Hz, 1H), 7.37-7.40 (d, J=8.8 Hz, 2H), 7.69-7.72 (d, J=8.8 Hz, 2H), 7.91 (d, J=1.6 Hz, 1H); $^{13}$C NMR (75 MHz) δ 14.3, 22.0, 24.0, 24.3, 26.5, 36.6, 44.7, 47.1, 55.35, 55.38, 61.8, 93.1, 104.9, 112.7, 126.3, 127.3, 128.1, 130.8, 131.1, 135.0, 146.6, 167.3, 168.8, 203.3; ESI-MS obsd 567.20069, calcd 567.20025 [(M+H)$^+$, M=C$_{26}$H$_{34}$N$_2$O$_{10}$S].

6-[4-(3-Methoxy-3-oxopropanoyl)pyrrol-2-yl]-1,1-dimethoxy-4,4-dimethyl-5-nitrohexan-2-one (3a)

Following a standard procedure,[25] a sample of 2a (1.10 g, 2.00 mmol) was treated with TBAF (1.0 M in THF, 2.0 mL, 2.0 mmol) in a 20-mL flask and heated to 65° C. for 1 h. The mixture was allowed to cool down to room temperature, quenched by addition of saturated NaHCO$_3$ aqueous solution and then extracted with ethyl acetate. The combined organic extract was washed (brine and water), dried (Na$_2$SO$_4$) and concentrated. Chromatography [silica, hexanes/ethyl acetate (1:1)] gave a yellow oil (566 mg, 70%): $^1$H NMR (300 MHz) δ 1.13 (s, 3H), 1.21 (s, 3H), 2.57-2.76 (AB, $^2$J=18.6 Hz, 2H), 2.99-3.05 (ABX, $^2$J=15.6 Hz, $^3$J=2.4 Hz, 1H), 3.29-3.37 (ABX, $^2$J=15.6 Hz, $^3$J=12.0 Hz, 1H), 3.43 (s, 3H), 3.43 (s, 3H), 3.72 (s, 3H), 3.75 (s, 2H), 4.37 (s, 1H), 5.15-5.20 (ABX, $^2$J=11.7 Hz, $^3$J=2.7 Hz, 1H), 6.40 (m, 1H), 7.33-7.35 (m, 1H), 9.14 (br, 1H); $^{13}$C NMR (100 MHz) δ 24.2, 24.3, 26.5, 36.6, 45.1, 46.6, 52.5, 55.3, 94.2, 104.7, 107.8, 124.8, 125.3, 128.8, 168.6, 187.3, 203.9; ESI-MS obsd 399.1755, calcd 399.1762 [(M+H)$^+$, M=C$_{18}$H$_{26}$N$_2$O$_8$].

6-[4-(3-Ethoxy-3-oxopropanoyl)pyrrol-2-yl]-1,1-dimethoxy-4,4-dimethyl-5-nitrohexan-2-one (3b)

Following a standard procedure,[25] a sample 2b (160 mg, 0.283 mmol) was treated with TBAF (1.0 M in THF, 0.34 mL, 0.34 mmol) in a 20-mL flask and heated to 65° C. for 1 h. The mixture was allowed to cool down to room temperature, quenched by addition of saturated NaHCO$_3$ aqueous solution and then extracted with ethyl acetate. The combined organic extracts were washed (brine and water), dried (Na$_2$SO$_4$) and concentrated. Chromatography [silica, hexanes/ethyl acetate (1:1), then ethyl acetate] gave a yellow oil (75 mg, 64%): $^1$H NMR (300 MHz) δ 1.20 (s, 3H), 1.21 (s, 3H), 1.24 (t, J=6.9 Hz, 3H), 2.56-2.75 (AB, $^2$J=18.6 Hz, 2H), 2.98-3.04 (ABX, $^2$J=15.3 Hz, $^3$J=2.4 Hz, 1H), 3.28-3.37 (ABX, $^2$J=15.3 Hz, $^3$J=11.7 Hz, 1H), 3.42 (s, 3H), 3.43 (s, 3H), 3.72 (s, 2H), 4.14-4.21 (q, J=6.9 Hz, 2H), 4.36 (s, 1H), 5.14-5.19 (ABX, $^2$J=12.0 Hz, 3J=2.4 Hz, 1H), 6.39 (m, 1H), 7.32 (m, 1H), 9.06 (br, 1H); $^{13}$C NMR (100 MHz) δ 14.3, 24.3, 26.6, 36.7, 45.3, 46.9, 55.4, 61.6, 94.3, 104.7, 107.8, 125.1, 125.4, 129.0, 168.5, 187.9, 204.0; ESI-MS obsd 413.19184, calcd 413.19180 [(M+H)$^+$, M=C$_{19}$H$_{28}$N$_2$O$_8$].

2,3-Dihydro-1-(1,1-dimethoxymethyl)-8-(3-methoxy-3-oxopropanoyl)-3,3-dimethyldipyrrin (4a)

Following a standard procedure,[4] a solution of 3a (566 mg, 1.42 mmol) in THF (14.0 mL) was treated with NaOCH$_3$ (307 mg, 5.68 mmol) in a 20-mL round bottom flask under argon at 0° C. The mixture was stirred at room temperature for 45 min. In a 250-mL round bottom flask, NH$_4$OAc (11.1 g, 142 mmol) in distilled THF (36.0 mL) was bubbled with argon for 15 min before a solution of TiCl$_3$ (12 wt % in 2 N HCl, 14.0 mL, 11.4 mmol) was added. The mixture was stirred for another 15 min. Then the mixture in the first flask was transferred to the buffered TiCl$_3$ solution in the second one via a cannula. The resulting mixture was stirred at room temperature under argon for 20 h. The reaction mixture was poured into saturated NaHCO$_3$ aqueous solution, filtered through a Celite Pad (the filter cake was washed with ethyl acetate) and extracted with ethyl acetate. The organic extracts were combined, washed (brine/water), dried (Na$_2$SO$_4$) and concentrated. Chromatography [silica, CH$_2$Cl$_2$, then CH$_2$Cl$_2$/ethyl acetate (1:1)] gave a yellow oil (223 mg, 45%): $^1$H NMR (300 MHz) δ 1.22 (s, 6H), 2.64 (s, 2H), 3.46 (s, 6H), 3.73 (s, 3H), 3.77 (s, 2H), 5.04 (s, 1H), 5.84 (s, 1H), 6.53 (m, 1H), 7.50 (m, 1H), 11.20 (br, 1H); $^{13}$C NMR (75 MHz) δ 29.0, 40.3, 46.8, 48.4, 52.4, 54.7, 102.5, 106.4, 108.4, 125.1, 125.6, 132.7, 162.2, 168.6, 176.2, 187.1; ESI-MS obsd 349.1758, calcd 349.1758 [(M+H)$^+$, M=$C_{18}H_{24}N_2O_5$].

8-(3-Ethoxy-3-oxopropanoyl)-2,3-dihydro-1-(1,1-dimethoxymethyl)-3,3-dimethyldipyrrin (4b)

Following a standard procedure,[4] a solution of 3b (75 mg, 0.182 mmol) in THF (1.8 mL) and MeOH (50. µL) was treated with NaOCH$_3$ (39 mg, 0.728 mmol) in a 20-mL round bottom flask under argon at 0° C. The mixture was stirred at 0° C. for 45 min. In a 100-mL round bottom flask, NH$_4$OAc (1.42 g, 18.2 mmol) in distilled THF (18 mL) was bubbled with argon for 15 min before a solution of TiCl$_3$ (12 wt % in 2 N HCl, 1.8 mL, 1.46 mmol) was added. The mixture was stirred for another 15 min. Then the mixture in the first flask was transferred to the buffered TiCl$_3$ solution in the second one via a cannula. The resulting mixture was stirred at room temperature under argon for 20 h. The reaction mixture was poured into saturated NaHCO$_3$ aqueous solution and extracted with ethyl acetate. The organic extracts were combined, washed (brine/water), dried (Na$_2$SO$_4$) and concentrated. Chromatography [silica, CH$_2$Cl$_2$, then CH$_2$Cl$_2$/ethyl acetate (1:1)] gave a yellow oil (24 mg, 36%): $^1$H NMR (300 MHz) δ 1.22 (s, 6H), 1.26 (t, J=7.2 Hz, 3H), 2.64 (s, 2H), 3.46 (s, 6H), 3.77 (s, 2H), 4.16-4.23 (q, J=7.2 Hz, 2H), 5.03 (s, 1H), 5.84 (s, 1H), 6.53 (m, 1H), 7.50 (m, 1H), 11.18 (br, 1H); $^{13}$C NMR (75 MHz) δ 14.4, 29.2, 40.4, 47.3, 48.6, 54.8, 61.5, 102.6, 106.6, 108.6, 125.3, 125.6, 132.8, 162.2, 168.3, 176.3, 187.4; ESI-MS obsd 363.19145, calcd 363.19160 [(M+H)$^+$, M=$C_{19}H_{26}N_2O_5$].

7-(4-Bromophenyl)-1-formyl-2,3-dihydro-3,3-dimethyldipyrrin (5-Ar)

Following a standard procedure,[5] a solution of 11-Ar (300 mg, 0.87 mmol) in 1,4-dioxane (17.4 mL) was treated with SeO$_2$ (288 mg, 2.60 mmol) under argon. Progress of the reaction was monitored with absorption spectrum. After 90 min, ethyl acetate (200 mL) was added. The organic layer was washed [aqueous NaHCO$_3$ solution (200 mL); water/brine (2×200 mL)], dried and concentrated. Chromatography [silica, hexanes/ethyl acetate (3:1)] afforded a red solid (67 mg, 22%): $^1$H NMR (400 MHz) δ 1.22 (s, 6H), 2.72 (s, 2H), 6.29 (s, 1H), 6.33 (m, 1H), 7.00 (m, 1H), 7.29-7.31 (d, J=8.8 Hz, 2H), 7.53-7.55 (d, J=8.8 Hz, 2H), 9.99 (s, 1H), 10.81 (br, 1H); $^{13}$C NMR (100 MHz) δ 29.2, 41.2, 46.1, 109.9, 112.4, 120.4, 122.1, 127.2, 127.7, 130.4, 131.8, 135.3, 161.2, 169.3, 190.1; ESI-MS obsd 357.0592, calcd 357.0597 [(M+H)$^+$, M=$C_{18}H_{17}BrN_2O$].

8-Ethoxycarbonyl-7-ethyl-1-formyl-2,3-dihydro-3,3-dimethyldipyrrin (5-EtEs)

Following a standard procedure,[5] a solution of 11-EtEs (100 mg, 0.33 mmol) in 1,4-dioxane (6.6 mL) was treated with SeO$_2$ (111 mg, 1.0 mmol) under argon. Progress of the reaction was monitored with absorption spectrum. After 90 min, ethyl acetate (100 mL) was added. The organic layer was washed with aqueous NaHCO$_3$ solution (100 mL), water/brine (2×100 mL), dried and concentrated. Chromatography [silica, hexanes/ethyl acetate (3:1)] afforded a red solid (32 mg, 32%): $^1$H NMR (400 MHz) δ 1.20 (t, J=7.2 Hz, 3H), 1.27 (s, 6H), 1.36 (t, J=6.8 Hz, 3H), 2.73 (s, 2H), 2.84-2.89 (q, J=7.2 Hz, 2H), 4.26-4.32 (q, J=6.8 Hz, 2H), 6.18 (s, 1H), 7.53 (d, J=3.2 Hz, 1H), 9.98 (s, 1H), 10.82 (br, 1H); $^{13}$C NMR (100 MHz) δ 14.6, 16.5, 18.2, 29.3, 41.1, 46.1, 59.6, 111.1, 115.0, 127.4, 128.3, 130.4, 160.7, 165.0, 169.4, 190.0; ESI-MS obsd 303.1699, calcd 303.1703 [(M+H)$^+$, M=$C_{17}H_{22}N_2O_3$].

Ethyl 3-(4-bromophenyl)prop-2-enoate (6)

Following a standard procedure,[4] a solution of 4-bromobenzaldehyde (17.4 g, 94.0 mmol) and (carbethoxymethylene)triphenylphosphorane (35.8 g, 103 mmol) in CH$_2$Cl$_2$ (120 mL) was refluxed for 20 h. The reaction mixture was allowed to cool to room temperature and then concentrated. The residue was diluted with Et$_2$O and filtered. The filtrate was washed with brine, dried (Na$_2$SO$_4$) and concentrated. Chromatography [silica, hexanes/ethyl acetate (2:1)] gave a colorless oil (21.9 g, 91%): $^1$H NMR (400 MHz) δ 1.33 (t, J=7.2 Hz, 3H), 4.26 (q, J=7.2 Hz, 2H), 6.41 (d, J=16.0 Hz, 1H), 7.37 (d, J=8.8 Hz, 2H), 7.50 (d, J=8.8 Hz, 2H), 7.60 (d, J=16.0 Hz, 1H); $^{13}$C NMR (100 MHz) δ 14.4, 60.7, 119.0, 124.5, 129.5, 132.2, 133.4, 143.2, 166.8; ESI-MS obsd 255.0011, calcd 255.0015 [(M+H)$^+$, M=$C_{11}H_{11}BrO_2$].

3-(4-Bromophenyl)pyrrole (7)

Following a standard procedure,[4] a suspension of 6 (21.9 g, 85.8 mmol) and TosMIC (16.7 g, 85.8 mmol) in dry ether/DMSO (2:1, 150 mL) was added dropwise to a suspension of NaH (60% in mineral oil, 5.16 g, 129 mmol) in dry ether (70 mL) under argon. The mixture was stirred at room temperature for 5 h. Water (200 mL) was added. The aqueous phase was extracted twice with ethyl acetate (2×200 mL). The organic layer was separated, dried (Na$_2$SO$_4$) and concentrated to a brown solid. The crude product was dissolved in ethylene glycol (200 mL) in a 500 mL round-bottom flask and bubbled with argon for 10 min. Powdered NaOH (17.2 g, 430 mmol) was added. The flask was heated to 160° C. in an oil bath. After 2.5 h, the reaction mixture was allowed to cool to room temperature, whereupon brine (200 mL) was added. The resulted mixture was extracted with CH$_2$Cl$_2$. The combined organic layer was dried (Na$_2$SO$_4$) and concentrated. The crude product was recrystallized from hot ethanol to afford a yellow solid (10.9 g, 57%): mp 142-143° C.; $^1$H NMR (400 MHz) δ 6.49 (m, 1H), 6.81 (m, 1H), 7.04 (m, 1H), 7.37-7.39 (d, J=8.4 Hz, 2H), 7.42-7.44 (d, J=8.4 Hz, 2H), 8.24 (br, 1H); $^{13}$C NMR (100 MHz) δ 106.5, 114.8, 119.0, 119.3, 123.9, 126.9, 131.7, 134.9; ESI-MS obsd 221.9910, calcd 221.9913 [(M+H)$^+$, M=$C_{10}H_8BrN$].

3-(4-Bromophenyl)-2-formylpyrrole (8)

Following a standard procedure,[4] a solution of 7 (10.9 g, 49.0 mmol) in DMF (15.2 mL, 196 mmol) and CH$_2$Cl$_2$ (200 mL) was cooled to 0° C. under argon and then POCl$_3$ (5.5 mL, 58.8 mmol) was added dropwise. After 1 h, the ice bath was removed and the mixture was stirred overnight. Then, the reaction mixture was cooled to 0° C. again, whereupon 2.0 M aqueous NaOH solution (350 mL) was added. The mixture was extracted with CH$_2$Cl$_2$. The combined organic extract was washed with brine, dried (Na$_2$SO$_4$) and concentrated. Chromatography [silica, CH$_2$Cl$_2$] gave a yellow solid (9.44 g, 77%): mp 163-164° C.; $^1$H NMR (400 MHz) δ 6.43 (m, 1H), 7.17 (m, 1H), 7.35-7.37 (d, J=8.0 Hz, 2H), 7.56-7.58 (d, J=8.0 Hz, 2H), 9.59 (s, 1H), 10.41 (br, 1H); $^{13}$C NMR (100 MHz) δ 111.6, 122.2, 126.3, 128.8, 130.8, 132.0, 132.8, 136.2, 179.7; ESI-MS obsd 249.9863, calcd 249.9862 [(M+H)$^+$, M=$C_{11}H_8BrNO$].

3-(4-Bromophenyl)-2-(2-nitroethyl)pyrrole (9-Ar)

Following a standard procedure,[4] a mixture of pyrrole 8 (9.44 g, 37.8 mmol), potassium acetate (4.08 g, 41.6 mmol), methylamine hydrochloride (2.87 g, 41.6 mmol), and nitromethane (75 mL) was stirred at room temperature under argon. The progress of reaction was monitored via TLC analysis. After 2 h, brine was added. The resulting mixture was extracted with ethyl acetate. The combined organic extract was washed with brine and water, dried ($Na_2SO_4$) and concentrated to afford an orange solid. The crude solid was dissolved in anhydrous THF/MeOH (166 mL, 9:1) under argon at 0° C. The mixture was stirred vigorously. $NaBH_4$ (2.51 g, 66.4 mmol) was added in one portion, and stirring was continued for 1 h at 0° C., then for 2 h at room temperature. The reaction mixture was neutralized to pH 7 with acetic acid. Water was added followed by extraction with ethyl acetate. The combined organic extract was washed with brine and water, dried ($Na_2SO_4$), and chromatographed [silica, hexanes/ethyl acetate (1:1)] to give a yellow solid (8.01 g, 72%): mp 93-94° C.; $^1$H NMR (400 MHz) δ 3.42 (t, J=6.6 Hz, 2H), 4.54 (t, J=6.6 Hz, 2H), 6.26 (m, 1H), 6.74 (m, 1H), 7.19-7.21 (d, J=8.0 Hz, 2H), 7.49-7.51 (d, J=8.0 Hz, 2H), 8.33 (br, 1H); $^{13}$C NMR (100 MHz) δ 24.2, 75.0, 109.4, 117.9, 119.9, 122.0, 122.2, 129.6, 131.8, 135.2; ESI-MS obsd 295.0078, calcd 295.0077 [(M+H)$^+$, M=$C_{12}H_{11}BrN_2O_2$].

6-[3-(4-Bromophenyl)pyrrol-2-yl]-4,4-dimethyl-5-nitrohexan-2-one (10-Ar)

Following a standard procedure,[5] a mixture of 9-Ar (8.01 g, 27.1 mmol) and mesityl oxide (6.2 mL, 54.2 mmol) was treated with DBU (8.1 mL, 54 mmol) at room temperature. After 16 h, water was added, and the mixture was extracted with ethyl acetate (2×100 mL). The organic layer was washed thoroughly with brine and water, dried ($Na_2SO_4$), concentrated, and chromatographed [silica, hexanes/ethyl acetate (3:1)] to give a brown oil (4.63 g, 44%): $^1$H NMR (300 MHz) δ 1.08 (s, 3H), 1.19 (s, 3H), 2.11 (s, 3H), 2.34-2.59 (AB, $^2$J=18.0 Hz, 2H), 3.12-3.18 (ABX, $^2$J=15.6 Hz, $^3$J=2.7 Hz, 1H), 3.35-3.44 (ABX, $^2$J=15.6 Hz, $^3$J=11.4 Hz, 1H), 5.19-5.23 (ABX, $^2$J=11.4 Hz, $^3$J=2.4 Hz, 1H), 6.21-6.22 (m, 1H), 6.68-6.70 (m, 1H), 7.20-7.22 (d, $^2$J=8.4 Hz, 2H), 7.49-7.52 (d, $^2$J=8.4 Hz, 2H), 8.20 (br, 1H); $^{13}$C NMR (100 MHz) δ 24.2, 24.5, 25.2, 31.9, 37.1, 51.5, 94.4, 109.4, 118.1, 120.1, 122.5, 122.7, 130.1, 120.2, 131.7, 131.8, 125.6, 206.9; ESI-MS obsd 393.0808, calcd 393.0808 [(M+H)$^+$, M=$C_{18}H_{21}BrN_2O_3$].

7-(4-Bromophenyl)-2,3-dihydro-1,3,3-trimethyl-dipyrrin (11-Ar)

Following a standard procedure,[5] a solution of 10-Ar (4.63 g, 11.8 mmol) in distilled THF (22 mL) and dry methanol (1.0 mL) under argon was treated with NaOMe (1.91 g, 35.4 mmol), and the mixture was stirred for 45 min at room temperature. In a second flask, $TiCl_3$ (20 wt % in 3% HCl solution, 60. mL), THF (160 mL) and $NH_4OAc$ (45 g) were combined under argon, and the mixture was degassed by bubbling with argon for 45 min. The solution in the first flask containing the nitronate anion was transferred via a cannula to the buffered $TiCl_3$ mixture in the second one. The resulting mixture was stirred at room temperature for 16 h under argon. The reaction mixture was poured over a pad of Celite and eluted with ethyl acetate. The eluant was washed with aqueous $NaHCO_3$ solution. The organic phase was dried ($Na_2SO_4$) and concentrated. Chromatography [silica, hexanes/ethyl acetate (1:1)] afforded a light yellow solid (1.50 g, 37%): mp 119-121° C.; $^1$H NMR (400 MHz) δ 1.19 (s, 6H), 2.23 (s, 3H), 2.52 (s, 2H), 5.89 (s, 1H), 6.26 (m, 1H), 6.85 (m, 1H), 7.31-7.33 (d, J=8.0 Hz, 2H), 7.49-7.51 (d, J=8.0 Hz, 2H), 11.10 (br, 1H); $^{13}$C NMR (100 MHz) δ 20.8, 29.2, 41.3, 53.8, 102.4, 108.7, 118.6, 119.2, 122.1, 127.6, 130.2, 131.2, 136.3, 162.0, 177.3; ESI-MS obsd 343.0807, calcd 343.0804 [(M+H)$^+$, M=$C_{18}H_{19}BrN_2$].

8-Ethoxycarbonyl-7-ethyl-1,3,3-trimethyl-2,3-dihydrodipyrrin (11-EtEs)

Following a standard procedure,[5] a mixture of 4-ethoxycarbonyl-3-ethyl-2-(2-nitroethyl)pyrrole (9-EtEs, 5.1 g, 21 mmol) and mesityl oxide (4.1 g, 42 mmol) was treated with DBU (10 mL, 64 mmol) at room temperature. After 16 h, water was added and the mixture was extracted with ethyl acetate (2×100 mL). The organic layer was washed with brine and water thoroughly, dried ($Na_2SO_4$), concentrated to a brown oil on a rotary evaporator and dried under high vacuum overnight. The crude material (4.2 g) was used directly in the next step. In a first flask, a solution of the crude material in distilled THF (20 mL) and dry methanol (1.0 mL) under argon was treated with NaOMe (2.0 g, 37 mmol), and the mixture was stirred for 45 min at room temperature. In a second flask, $TiCl_3$ (20 wt % in 3% HCl solution, 63 mL, 100 mmol), THF (160 mL) and $NH_4OAc$ (47 g, 620 mmol) were combined under argon, and the mixture was degassed by bubbling with argon for 45 min. The solution in the first flask containing the nitronate anion was transferred via a cannula to the buffered $TiCl_3$ mixture in the second one. The resulting mixture was stirred at room temperature for 16 h under argon. The reaction mixture was poured over a pad of Celite and eluted with ethyl acetate. The eluant was washed with aqueous $NaHCO_3$ solution. The organic phase was dried ($Na_2SO_4$) and concentrated. Chromatography [silica, hexanes/ethyl acetate (3:1)] afforded a yellow oil (1.4 g, 23%): $^1$H NMR (400 MHz) δ 1.16 (t, J=7.6 Hz, 3H), 1.22 (s, 6H), 1.34 (t, J=7.0 Hz, 3H), 2.21 (s, 3H), 2.52 (s, 2H), 2.78-2.83 (q, J=7.6 Hz, 2H), 4.24-4.29 (q, J=7.0 Hz, 2H), 5.71 (s, 1H), 7.40 (d, J=3.2 Hz, 1H), 11.15 (br, 1H); $^{13}$C NMR (100 MHz) δ 14.6, 16.4, 18.1, 20.8, 29.3, 41.3, 53.9, 59.2, 101.4, 114.0, 124.5, 125.1, 128.6, 161.3, 165.7, 177.1; ESI-MS obsd 289.1907, calcd 289.1911 [(M+H)$^+$, M=$C_{17}H_{24}N_2O_2$].

2-Carbomethoxy-3-(2,3-dihydro-3,3-dimethyl-7-p-tolyldipyrrin-1-yl)-1-[2,3-dihydro-1-(1,1-dimethoxymethyl)-3,3-dimethyldipyrrin-8-yl]-prop-2-en-1-one (12-T)

Samples of 4a (17 mg, 49 μmol), 5-T (17 mg, 58 μmol, 1.2 equiv) and dried molecular sieves 3 Å powder (17 mg) were placed in a 20-mL vial under argon. A solution of piperidine/acetic acid in $CH_2Cl_2$ (15 mM/15 mM, 1.2 mL, 18 μmol/18 μmol) was added, and the mixture was stirred at room temperature for 20 h. The reaction mixture was filtered through a Celite pad. The filtrate was concentrated and chromatographed [silica, hexanes/ethyl acetate (3:1 then 1:1)] to give an orange/red gum (19 mg, 61%): $^1$H NMR (400 MHz) δ 1.07 (s, 6H), 1.22 (s, 6H), 2.37 (s, 3H), 2.56 (s, 2H), 2.64 (s, 2H), 3.44 (s, 6H), 3.78 (s, 3H), 5.00 (s, 1H), 5.85 (s, 1H), 6.12 (s, 1H), 6.27 (m, 1H), 6.57 (s, 1H), 6.91 (m, 1H), 7.19-7.21 (d, J=7.6 Hz, 2H), 7.30-7.32 (d, J=7.6 Hz, 2H), 7.39 (s, 1H), 7.65 (s, 1H), 10.68 (br, 1H), 11.27 (br, 1H); $^{13}$C NMR (100 MHz) δ 21.3, 29.07, 29.09, 40.4, 41.8, 48.5, 50.4, 52.9, 54.7, 102.4, 106.4, 108.2, 108.8, 109.4, 121.0, 126.0, 126.5, 126.9, 127.4, 128.7, 129.3, 129.4, 133.3, 133.9, 134.9, 135.6, 138.0, 161.0, 162.5, 165.7, 167.3, 176.6, 188.5; ESI-MS obsd 623.3224, calcd 623.3228 [(M+H)$^+$, M=$C_{37}H_{42}N_4O_5$].

3-[7-(4-Bromophenyl)-2,3-dihydro-3,3-dimethylpyrrin-1-yl]-2-carbomethoxy-1-[2,3-dihydro-1-(1,1-dimethoxymethyl)-3,3-dimethyldipyrrin-8-yl]-prop-2-en-1-one (12-Ar)

Reaction of 4a (31 mg, 90 μmol) and 5-Ar (32 mg, 90 μmol) under the general procedure for 12-T followed by chromatography [silica, hexanes/ethyl acetate (3:1 then 1:1)] gave an orange/red gum (38 mg, 68%): $^1$H NMR (400 MHz) δ 1.08 (s, 6H), 1.22 (s, 6H), 2.57 (s, 2H), 2.64 (s, 2H), 3.44 (s, 6H), 3.79 (s, 3H), 5.01 (s, 1H), 5.85 (s, 1H), 6.03 (s, 1H), 6.25 (m, 1H), 6.56 (s, 1H), 6.92 (m, 1H), 7.25-7.28 (d, J=8.4 Hz, 2H), 7.39 (s, 1H), 7.48-7.50 (d, J=8.4 Hz, 2H), 7.64 (s, 1H), 10.70 (br, 1H), 11.27 (br, 1H); $^{13}$C NMR (100 MHz) δ 29.1, 40.4, 41.7, 48.6, 50.5, 53.0, 54.7, 102.4, 106.4, 108.1, 108.2, 109.2, 119.8, 121.1, 125.0, 125.9, 126.8, 127.6, 130.3, 131.7, 133.3, 134.6, 135.8, 138.4, 161.6, 162.6, 165.6, 167.9, 176.6, 188.4; ESI-MS obsd 687.2168, calcd 687.2177 [(M+H)$^+$, M=$C_{36}H_{39}BrN_4O_5$].

2-Carbomethoxy-3-(2,3-dihydro-3,3,7,8-tetramethyl-dipyrrin-1-yl)-1-[2,3-dihydro-1-(1,1-dimethoxymethyl)-3,3-dimethyldipyrrin-8-yl]-prop-2-en-1-one (12-MeMe)

Reaction of 4a (35 mg, 100 μmol) and 5-MeMe (41 mg, 120 μmol, 1.2 equiv) under the general procedure for 12-T followed by chromatography [silica, hexanes/ethyl acetate (3:1 then 1:1)] gave an orange/red gum (47 mg, 71%): $^1$H NMR (400 MHz) δ 1.08 (s, 6H), 1.22 (s, 6H), 1.63 (s, 9H), 2.03 (s, 3H), 2.25 (s, 3H), 2.51 (s, 2H), 2.64 (s, 2H), 3.44 (s, 6H), 3.78 (s, 3H), 5.01 (s, 1H), 5.85 (s, 1H), 5.88 (s, 1H), 6.54 (s, 1H), 7.36 (s, 1H), 7.73 (s, 1H), 11.02 (br, 1H), 11.29 (br, 1H); $^{13}$C NMR (100 MHz) δ 9.0, 10.6, 28.6, 29.06, 29.09, 40.4, 42.2, 48.5, 49.6, 52.9, 54.7, 80.3, 102.4, 106.4, 106.8, 108.2, 121.0, 121.6, 126.3, 127.2, 130.4, 133.5, 135.9, 139.1, 161.0, 162.6, 162.9, 165.5, 170.1, 176.7, 188.1; ESI-MS obsd 661.3590, calcd 661.3596 [(M+H)$^+$, M=$C_{37}H_{48}N_4O_7$].

2-Carbomethoxy-3-(8-ethoxycarbonyl-7-ethyl-2,3-dihydro-3,3-dimethyldipyrrin-1-yl)-1-[2,3-dihydro-1-(1,1-dimethoxymethyl)-3,3-dimethyldipyrrin-8-yl]-prop-2-en-1-one (12-EtEs)

Reaction of 4a (25 mg, 71 μmol) and 5-EtEs (32 mg, 106 μmol, 1.5 equiv) under the general procedure for 12-T followed by chromatography [silica, hexanes/ethyl acetate (3:1 then 1:1)] gave an orange/red gum (27 mg, 61%): $^1$H NMR (400 MHz) 1.12 (s, 6H), 1.14 (t, J=7.2 Hz, 3H), 1.22 (s, 6H), 1.35 (t, J=7.0 Hz, 3H), 2.58 (s, 2H), 2.64 (s, 2H), 2.76-2.82 (q, J=7.2 Hz, 2H), 3.44 (s, 6H), 3.78 (s, 3H), 4.25-4.30 (q, J=7.0 Hz, 2H), 5.01 (s, 1H), 5.86 (s, 1H), 5.89 (s, 1H), 6.55 (s, 1H), 7.39 (s, 1H), 7.45 (d, J=3.2 Hz, 1H), 7.60 (s, 1H), 10.60 (br, 1H), 11.28 (br, 1H); $^{13}$C NMR (100 MHz) δ 14.6, 16.5, 18.1, 29.1, 29.2, 40.4, 41.6, 48.5, 50.7, 53.0, 54.7, 59.4, 102.4, 106.4, 106.9, 108.1, 114.3, 125.8, 126.8, 128.2, 128.7, 133.3, 134.3, 138.4, 160.9, 162.6, 165.4, 165.5, 167.8, 176.6, 188.5; ESI-MS obsd 633.3268, calcd 633.3283 [(M+H)$^+$, M=$C_{35}H_{44}N_4O_7$].

3-[7-(4-Bromophenyl)-2,3-dihydro-3,3-dimethylpyrrin-1-yl]-2-ethoxycarbonyl-[2,3-dihydro-1-(1,1-dimethoxymethyl)-3,3-dimethyldipyrrin-8-yl]-prop-2-en-1-one (12-Ar/Et)

Reaction of 4b (31 mg, 84 &μmol) and 1-Ar (36 mg, 100 μmol, 1.2 equiv) under the general procedure for 12-T followed by chromatography [silica, hexanes/ethyl acetate (3:1 then 1:1)] gave an orange/red gum (33 mg, 57%): $^1$H NMR (300 MHz) δ 1.08 (s, 6H), 1.22 (s, 6H), 1.25 (t, J=7.2 Hz, 3H), 2.57 (s, 2H), 2.64 (s, 2H), 3.43 (s, 6H), 4.22-4.29 (q, J=7.2 Hz, 2H), 5.00 (s, 1H), 5.84 (s, 1H), 6.03 (s, 1H), 6.24 (m, 1H), 6.56 (m, 1H), 6.91 (m, 1H), 7.25-7.28 (d, J=8.4 Hz, 2H), 7.38 (m, 1H), 7.48-7.51 (d, J=8.4 Hz, 2H), 7.61 (s, 1H), 10.71 (br, 1H), 11.24 (br, 1H); $^{13}$C NMR (100 MHz) δ 14.26, 14.32, 29.1, 40.4, 41.7, 48.6, 50.6, 54.7, 62.0, 102.5, 106.5, 108.0, 108.2, 109.2, 119.8, 121.1, 124.9, 126.0, 126.7, 127.6, 130.3, 131.7, 133.2, 134.2, 135.9, 139.0, 161.6, 162.5, 165.0, 168.1, 176.6, 188.4. ESI-MS obsd 701.2334, calcd 701.2333 [(M+H)$^+$, M=$C_{37}H_{41}BrN_4O_5$].

13$^2$-Methoxycarbonyl-8,8,18,18-tetramethyl-2-p-tolylbacterio-13$^1$-oxophorbine (BC-T)

A solution of 12-T (19 mg, 30 μmol) in acetonitrile (ACS grade, 150 mL) was degassed by bubbling with argon for 20 min. Yb(OTf)$_3$ (186 mg, 0.30 mmol) was added in one portion under argon. The reaction mixture was immediately heated to 80° C. and stirred at such temperature under argon for 20 h. The color of solution changed from orange-red to dark green during this process. After completion, the reaction mixture was allowed to cool down to room temperature and excess triethylamine (0.5 mL) was added. The reaction mixture was concentrated, and the residue was chromatographed [silica, hexanes/ethyl acetate (3:1 then 1:1)] to afford a blue-green solid (9.5 mg, 56%): $^1$H NMR (400 MHz) δ 0.52 (br, 1H), 1.72 (s, 3H), 1.82 (s, 9H), 2.03 (br, 1H), 2.58 (s, 3H), 3.76-3.88 (AB, J=16.8 Hz, 2H), 3.83 (s, 3H), 4.09 (s, 2H), 5.79 (s, 1H), 7.52-7.54 (d, J=7.8 Hz, 2H), 7.91-7.93 (d, J=7.8 Hz, 2H), 8.08 (s, 1H), 8.11 (m, 2H), 8.21 (s, 1H), 8.34 (d, J=1.6 Hz, 1H); $^{13}$C NMR (100 MHz) δ 21.6, 29.7, 30.1, 30.9, 31.0, 43.9, 45.6, 49.0, 52.9, 53.3, 64.7, 95.1, 98.2, 100.2, 106.0, 108.1, 126.3, 128.6, 130.1, 130.5, 131.8, 138.7, 140.1, 140.3, 141.9, 142.3, 149.8, 152.2, 165.5, 169.4, 169.8, 177.3, 188.6; ESI-MS obsd 559.2702, calcd 559.2704 [(M+H)$^+$, M=$C_{35}H_{34}N_4O_3$]; $\lambda_{abs}$ 356, 489, 520, 660, 721 nm.

2-(4-Bromophenyl)-13$^2$-methoxycarbonyl-8,8,18,18-tetramethylbacterio-13$^1$-oxophorbine (BC-Ar)

Reaction of 12-Ar (18 mg, 26 μmol) under the general procedure for BC-T followed by chromatography [silica, hexanes/ethyl acetate (3:1 then 3:2)] gave a blue-green solid (10.5 mg, 61%): $^1$H NMR (400 MHz) δ 0.31 (br, 1H), 1.73 (s, 3H), 1.78 (br, 1H), 1.82 (s, 3H), 1.83 (s, 6H), 3.79-3.91 (AB, J=16.8 Hz, 2H), 3.84 (s, 3H), 4.14 (s, 2H), 5.83 (s, 1H), 7.85-7.87 (d, J=8.4 Hz, 2H), 7.88-7.90 (d, J=8.4 Hz, 2H), 8.07 (s, 1H), 8.17 (s, 1H), 8.19 (s, 1H), 8.27 (s, 1H), 8.40 (d, J=1.6 Hz, 1H); $^{13}$C NMR (100 MHz) δ 29.8, 30.2, 31.0, 31.1, 44.0, 45.8, 48.9, 52.9, 53.2, 64.7, 94.8, 98.6, 100.4, 106.5, 108.3, 123.2, 126.5, 128.9, 132.1, 132.5, 133.7, 139.7, 140.2, 141.5, 149.7, 152.5, 165.2, 169.6, 169.8, 177.0, 188.6; ESI-MS obsd 623.1647, calcd 623.1652 [(M+H)$^+$, M=$C_{34}H_{31}BrN_4O_3$]; $\lambda_{abs}$ 356, 490, 521, 664, 727 nm.

13²-Methoxycarbonyl-2,3,8,8,18,18-hexamethylbacterio-13¹-oxophorbine (BC-MeMe)

Reaction of 12-MeMe (23 mg, 35 μmol) under the general procedure for BC-T followed by chromatography [silica, hexanes/ethyl acetate (3:1 then 1:1)] gave a blue solid (6.7 mg, 37%): $^1$H NMR (400 MHz) δ 1.16 (br, 1H), 1.62 (br, 1H), 1.72 (s, 3H), 1.75 (s, 6H), 1.80 (s, 3H), 2.93 (s, 3H), 2.95 (s, 3H), 3.62-3.74 (AB, J=16.8 Hz, 2H), 3.82 (s, 3H), 3.97 (s, 2H), 5.64 (s, 1H), 7.63 (s, 1H), 7.74 (s, 1H), 7.85 (s, 1H), 7.97 (s, 1H); $^{13}$C NMR (100 MHz) δ 10.9, 29.6, 29.9, 30.8, 30.9, 43.3, 45.1, 49.0, 52.8, 53.7, 64.4, 91.5, 94.3, 100.0, 104.6, 107.9, 127.7, 133.8, 134.2, 139.7, 142.4, 144.7, 150.6, 151.6, 166.3, 168.5, 169.9, 177.9, 188.5; ESI-MS obsd 497.2548, calcd 497.2547 [(M+H)$^+$, M=$C_{30}H_{32}N_4O_3$]; $\lambda_{abs}$ 351, 480, 511, 640, 696 nm.

3-Ethoxycarbonyl-2-ethyl-13²-methoxycarbonyl-8,8,18,18-tetramethylbacterio-13¹-oxophorbine (BC-EtEs)

Reaction of 12-EtEs (13 mg, 21 μmol) under the general procedure for BC-T followed by chromatography [silica, hexanes/ethyl acetate (4:1 then 2:1)] gave a purple solid (6.6 mg, 57%): $^1$H NMR (400 MHz) δ −0.07 (br, 1H), 1.59 (br, 1H), 1.66-1.69 (t, J=7.6 Hz, 3H), 1.67-1.71 (t, J=7.6 Hz, 3H), 1.81 (s, 3H), 1.83 (s, 6H), 1.91 (s, 3H), 3.81-3.91 (AB, J=16.2 Hz, 2H), 3.84 (s, 3H), 3.91-3.98 (q, J=7.6 Hz, 2H), 4.20 (s, 2H), 4.71-4.78 (q, J=7.6 Hz, 2H), 5.85 (s, 1H), 8.20 (s, 1H), 8.23 (s, 1H), 8.30 (s, 1H), 9.16 (s, 1H); $^{13}$C NMR (100 MHz) δ 14.7, 17.1, 20.8, 30.1, 30.4, 31.0, 31.1, 44.0, 45.9, 48.8, 52.9, 53.7, 61.5, 64.7, 94.0, 98.0, 100.4, 107.0, 108.6, 124.0, 129.3, 138.3, 139.5, 140.6, 148.1, 149.6, 153.1, 165.5, 165.8, 169.7, 170.4, 176.0, 188.6; ESI-MS obsd 569.2753, calcd 569.2758 [(M+H)$^+$, M=$C_{33}H_{36}N_4O_5$]; $\lambda_{abs}$ 357, 501, 533, 680, 745 nm.

2-(4-Bromophenyl)-13²-ethoxycarbonyl-8,8,18,18-tetramethylbacterio-13¹-oxophorbine (BC-Ar/Et)

Reaction of 12-Ar/Et (16 mg, 23 μmol) under the general procedure for BC-T followed by chromatography [silica, hexanes/ethyl acetate (3:1)] gave a blue-green solid (7.1 mg, 48%): $^1$H NMR (400 MHz) δ 0.27 (br, 1H), 1.23-1.27 (t, J=6.8 Hz, 3H), 1.73 (br, 1H), 1.75 (s, 3H), 1.81 (s, 3H), 1.83 (s, 6H), 3.81-3.92 (AB, J=16.8 Hz, 2H), 4.14 (s, 2H), 4.29-4.34 (q, J=6.8 Hz, 2H), 5.80 (s, 1H), 7.85-7.87 (d, J=8.0 Hz, 2H), 7.89-7.91 (d, J=8.0 Hz, 2H), 8.08 (s, 1H), 8.18 (s, 1H), 8.20 (s, 1H), 8.27 (s, 1H), 8.40 (d, J=2.0 Hz, 1H); $^{13}$C NMR (100 MHz) δ 14.4, 30.0, 30.1, 31.0, 31.3, 44.1, 45.8, 48.9, 53.3, 61.8, 65.0, 94.8, 98.6, 100.4, 106.6, 108.5, 123.2, 126.4, 129.1, 132.1, 132.5, 133.8, 139.7, 140.1, 140.2, 141.4, 149.7, 152.5, 165.1, 169.3, 169.6, 176.8, 188.8; ESI-MS obsd 636.1652, calcd 636.1652 [(M+H)$^+$, M=$C_{35}H_{33}BrN_4O_3$]; $\mu_{abs}$ 357, 489, 521, 665, 728 nm.

REFERENCES (1) Scheer, H. In *Chlorophylls and Bacteriochlorophylls: Biochemistry, Biophysics, Functions and Applications*; Grimm, B., Porra, R. J., Rudiger, W., Scheer, H., Eds.; Springer: Dordrecht, The Netherlands, 2006; pp 1-26.

(2) Kobayashi, M.; Akiyama, M.; Kano, H.; Kise, H. In: *Chlorophylls and Bacteriochlorophylls: Biochemistry, Biophysics, Functions and Applications*; Grimm, B., Porra, R. J., Rildiger, W., Scheer, H., Eds.; Springer: Dordrecht, The Netherlands, 2006; pp 79-94.

(3) Kim, H.-J.; Lindsey, J. S. *J. Org. Chem.* 2005, 70, 5475-5486.

(4) Krayer, M.; Ptaszek, M.; Kim, H.-J.; Meneely, K. R.; Fan, D.; Secor, K.; Lindsey, J. S. *J. Org. Chem.* 2010, 75, 1016-1039.

(5) Zhang, S.; Kim, H.-J.; Tang, Q.; Yang, E.; Bocian, D. F.; Holten, D.; Lindsey, J. S. *New J. Chem.* 2016, 40, 5942-5956.

(6) Lindsey, J. S. *Chem. Rev.* 2015, 115, 6534-6620.

(7) Liu, Y.; Lindsey, J. S. *J. Org. Chem.* DOI:10.1021/acs.joc6b02334.

(8) Yu, Z.; Ptaszek, M. *Org. Lett.* 2012, 14, 3708-3711.

(9) Minehan, T. G.; Kishi, Y. *Tetrahedron Lett.* 1997, 38, 6811-6814.

(10) Minehan, T. G.; Kishi, Y. *Angew. Chem. Int. Ed.* 1999, 38, 923-925.

(11) Wang, W.; Kishi, Y. *Org. Lett.* 1999, 1, 1129-1132.

(12) Brückner, C.; Samankumara, L.; Ogikubo, J. In *Handbook of Porphyrin Science*, Kadish, K. M.; Smith, K. M.; Guilard, R., Eds; World Scientific Publishing Co.: Singapore, 2012, vol. 17, pp 1-112.

(13) Seely, G. R. In *The Chlorophylls*; Vernon, L. P., Seely, G. R., Eds.; Academic Press: New York, N.Y., 1966; pp 67-109.

(14) Hynninen, P. H. In *Chlorophylls*; Scheer, H., Ed.; CRC Press: Boca Raton, Fla., 1991; pp 145-209.

(15) Moss, G. P. *Pure Appl. Chem.* 1987, 59, 779-832.

(16) Deans, R. M.; Mass, O.; Diers, J. R.; Bocian, D. F.; Lindsey, J. S. *New J. Chem.* 2013, 37, 3964-3975.

(17) Woodward, R. B.; Ayer, W. A.; Beaton, J. M.; Bickelhaupt, F.; Bonnett, R.; Buchschacher, P.; Closs, G. L.; Dutler, H.; Hannah, J.; Hauck, F. P.; It6, S.; Langemann, A.; Le Goff, E.; Leimgruber, W.; Lwowski, W.; Sauer, J.; Valenta, Z.; Volz, H. *J. Am. Chem. Soc.* 1960, 82, 3800-3802.

(18) Woodward, R. B. *Pure Appl. Chem.* 1961, 2, 383-404.

(19) Woodward, R. B.; Ayer, W. A.; Beaton, J. M.; Bickelhaupt, F.; Bonnett, R.; Buchschacher, P.; Closs, G. L.; Dutler, H.; Hannah, J.; Hauck, F. P.; It8, S.; Langemann, A.; Le Goff, E.; Leimgruber, W.; Lwowski, W.; Sauer, J.; Valenta, Z.; Volz, H. *Tetrahedron* 1990, 46, 7599-7659.

(20) Wenz, D. R.; de Alaniz, J. R. *Eur. J. Org. Chem.* 2015, 23-37.

(21) Song, C.; Knight, D. W.; Whatton, M. A. *Org. Lett.* 2006, 8, 163-166.

(22) Malona, J. A.; Colbourne, J. M.; Frontier, A. *J. Org. Lett.* 2006, 8, 5661-5664.

(23) Fujiwara, M.; Kawatsura, M.; Hayase, S.; Nanjo, M.; Itoh, T. *Adv. Synth. Catal.* 2009, 351, 123-128.

(24) Vaidya, T.; Atesin, A. C.; Herrick, I. R.; Frontier, A. J.; Eisenberg, R. *Angew. Chem. Int. Ed.* 2010, 49, 3363-3366.

(25) Krayer, M.; Balasubramanian, T.; Ruzié, C.; Ptaszek, M.; Cramer, D. L.; Taniguchi, M.; Lindsey, J. S. *J. Porphyrins Phthalocyanines* 2009, 13, 1098-1110.

(26) Baburajan, P.; Elango, K. P. *Tetrahedron Lett.* 2014, 55, 3425-3528.

(27) Khoury, R. G.; Senge, M. O.; Colchester, J. E.; Smith, K. M. *J. Chem. Soc., Dalton Trans.* 1996, 3937-3950.

(28) Aravindu, K.; Krayer, M.; Kim, H.-J.; Lindsey, J. S. *New J. Chem.* 2011, 35, 1376-1384.

(29) Tamiaki, H.; Kouraba, M.; Takeda, K.; Kondo, S.; Tanikaga, R. *Tetrahedron: Asymm.* 1998, 9, 2101-2111.

(30) Yang, E.; Kirmaier, C.; Krayer, M.; Taniguchi, M.; Kim, H.-J.; Diers, J. R.; Bocian, D. F.; Lindsey, J. S.; Holten, D. *J. Phys. Chem. B* 2011, 115, 10801-10816.

(31) van der Rest, M.; Gingras, G. *J. Biol. Chem.* 1974, 249, 6446-6453.

(32) Meyer, M.; Scheer, H.; Breton, J. *FEBS Lett.* 1996, 393, 131-134.

(33) Fischer, H.; Laubereau, O. *Justus Liebigs Ann. Chem.* 1938, 535, 17-37.

(34) Flaugh, M. E.; Rapoport, H. *J. Am. Chem. Soc.* 1968, 90, 6877-6879.

(35) Lash, T. D.; Quizon-Colquitt, D. M.; Shiner, C. M.; Nguyen, T. H.; Hu, Z. *Energy & Fuels* 1993, 7, 172-178.

(36) Fischer, H.; Lautsch, W. *Justus Liebigs Ann. Chem.* 1937, 528, 265-275.

(37) Fischer, H.; Oestreicher, A. *Justus Liebigs Ann. Chem.* 1940, 546, 49-57.

(38) Cox, M. T.; Howarth, T. T.; Jackson, A. H.; Kenner, G. W. *J. Am. Chem. Soc.* 1969, 91, 1232-1233.

(39) Kenner, G. W.; McCombie, S. W.; Smith, K. M. *J. Chem. Soc. Chem. Comm.* 1972, 844-845.

(40) Cox, M. T.; Howarth, T. T.; Jackson, A. H.; Kenner, G. W. *J. Chem. Soc. Perkin Trans.* 11974, 512-516.

(41) Kenner, G. W.; McCombie, S. W.; Smith, K. M. *J. Chem. Soc. Perkin Trans. I* 1974, 527-530.

(42) Smith, K. M.; Lewis, W. M. *Tetrahedron* 1981, 37 Supp. 1, 399-403.

(43) Laha, J. K.; Muthiah, C.; Taniguchi, M.; Lindsey, J. S. *J. Org. Chem.* 2006, 71, 7049-7052.

(44) Muthiah, C.; Lahaye, D.; Taniguchi, M.; Ptaszek, M.; Lindsey, J. S. *J. Org. Chem.* 2009, 74, 3237-3247.

(45) Mass, O.; Taniguchi, M.; Ptaszek, M.; Springer, J. W.; Faries, K. M.; Diers, J. R.; Bocian, D. F.; Holten, D.; Lindsey, J. S. *New J. Chem.* 2011, 35, 76-88.

(46) Krayer, M.; Yang, E.; Diers, J. R.; Bocian, D. F.; Holten, D.; Lindsey, J. S. *New J. Chem.* 2011, 35, 587-601.

(47) Gilmore, K.; Mohamed, R. K.; Alabugin, I. V. *WIREs Comput. Mol. Sci.* 2016. DOI: 10.1002/wcms.1261

(48) Paras, N. A.; MacMillan, D. W. C. *J. Am. Chem. Soc.* 2001, 123, 4370-4371.

(49) Evans, D. A.; Fandrick, K. R. *Org. Lett.* 2006, 8, 2249-2252.

(50) Sibi, M. P.; Coulomb, J.; Stanley, L. M. *Angew. Chem. Int. Ed.* 2008, 47, 9913-9915.

(51) Wang, W.; Liu, X.; Cao, W.; Wang, J.; Lin, L.; Feng, X. *Chem. Eur. J.* 2010, 16, 1664-1669.

(52) Huang, Y.; Tokunaga, E.; Suzuki, S.; Shiro, M.; Shibata, N. *Org. Lett.* 2010, 12, 1136-1138.

(53) Hack, D.; Enders, D. *Synthesis* 2013, 45, 2904-2912.

(54) Lee, S.-J.; Ahn, J.-G.; Cho, C.-W. *Tetrahedron: Asymm.* 2014, 25, 1383-1388.

(55) Hua, Y.-Z.; Han, X.-W.; Yang, X.-C.; Song, X.; Wang, M.-C.; Chang, J.-B. *J. Org. Chem.* 2014, 79, 11690-11699.

(56) Yadav, J. S.; Abraham, S.; Subba Reddy, B. V.; Sabitha, G. *Tetrahedron Lett.* 2001, 42, 8063-8065.

(57) de la Hoz, A.; Dïaz-Ortiz, A.; Gómez, M. V.; Mayoral, J. A.; Moreno, A.; Sánchez-Migallón, A. M.; Vázquez, E. *Tetrahedron* 2001, 57, 5421-5428.

(58) Wang, H.-S.; Yu, S. *J. Tetrahedron Lett.* 2002, 43, 1051-1055.

(59) Ünaleroglu, C.; Temelli, B.; Demir, A. S. *Synthesis* 2004, 2574-2578.

(60) Firouzabadi, H.; Iranpoor, N.; Nowrouzi, F. *Chem. Commun.* 2005, 789-791.

(61) Zhan, Z.-P.; Yang, W.-Z.; Yang, R.-F. *Synlett* 2005, 2425-2428.

(62) Zhang, C.-X.; Wang, Y.-Q.; Duan, Y.-S.; Ge, Z.-M.; Cheng, T.-M.; Li, R.-T. *Catalysis Commun.* 2006, 7, 534-537.

(63) Azizi, N.; Arynasab, F.; Saidi, M. R. *Org. Biomol. Chem.* 2006, 4, 4275-4277.

(64) Zhan, Z.-P.; Yu, J.-L.; Yang, W.-Z. *Synth. Commun.* 2006, 36, 1373-1382.

(65) Kusurkar, R. S.; Nayak, S. K.; Chavan, N. L. *Tetrahedron Lett.* 2006, 47, 7323-7326.

(66) Das, B.; Chowdhury, N.; Damodar, K. *Tetrahedron Lett.* 2007, 48, 2867-2870.

(67) Unaleroglu, C.; Yazici, A. *Tetrahedron* 2007, 63, 5608-5613.

(68) Aburatani, S.; Kawatsura, M.; Uenishi, J. *Heterocycles* 2007, 71, 189-196.

(69) Hong, S.-J.; Jeong, S.-D.; Yoo, J.; Kim, J. S.; Yoon, J.; Lee, C.-H. *Tetrahedron Lett.* 2008, 49, 4138-4141.

(70) Kawatsura, M.; Fujiwara, M.; Uehara, H.; Nomura, S.; Hayase, S.; Itoh, T. *Chem. Lett.* 2008, 37, 794-795.

(71) Unaleroglu, C.; Tasgin, D. I.; Aytac, S.; Temelli, B. *Synthesis* 2009, 3243-3250.

(72) Kitanosono, T.; Miyo, M.; Kobayashi, S. *Tetrahedron* 2015, 71, 7739-7744.

(73) Gtlrdere, M. B.; Ozbek, O.; Ceylan, M. *Synth. Commun.* 2016, 46, 322-331.

(74) Webb, I. D.; Borcherdt, G. T. *J. Am. Chem. Soc.* 1951, 73, 752-753.

(75) Treibs, A.; Michl, K.-H. *Ann. Chem.* 1954, 589, 163-173.

(76) Cheng, D. O.; Bowman, T. L.; LeGoff, E. *J. Heterocyclic Chem.* 1976, 13, 1145-1147.

(77) Treibs, A.; Wilhelm, R.; Herrmann, E. *Liebigs Ann. Chem.* 1981, 849-857.

(78) Hayakawa, K.; Yodo, M.; Ohsuki, S.; Kanematsu, K. *J. Am. Chem. Soc.* 1984, 106, 6735-6740.

(79) Ogoshi, H.; Mizushima, H.; Toi, H.; Aoyama, Y. *J. Org. Chem.* 1986, 51, 2366-2368.

(80) Kowalik, J.; Nguyen, H. T.; Tolbert, L. M. *Synth. Metals* 1991, 41-43, 435-438.

(81) Lüönd, R.; Neier, R. *Helv. Chim. Acta* 1991, 74, 91-102.

(82) Alazard, J.-P.; Millet-Paillusson, C.; Guénard, D.; Thal, C. *Bull. Soc. Chim. Fr.* 1996, 133, 251-266.

(83) Saracoglu, N. *Top. Heterocycl. Chem.* 2007, 11, 1-61.

(84) Senge, M. O.; Ryan, A. A.; Letchford, K. A.; MacGowan, S. A.; Mielke, T. *Symmetry* 2014, 6, 781-843.

(85) Mazaki, H.; Watanabe, T.; Takahashi, T.; Struck, A.; Scheer, H. *Bull. Chem. Soc. Jpn.* 1992, 65, 3080-3087.

(86) Mass, O.; Lindsey, J. S. *J. Org. Chem.* 2011, 76, 9478-9487.

(87) Fan, D.; Taniguchi, M.; Lindsey, J. S. *J. Org. Chem.* 2007, 72, 5350-5357.

(88) Kozyrev, A. N.; Chen, Y.; Goswami, L. N.; Tabaczynski, W. A.; Pandey, R. K. *J. Org. Chem.* 2006, 71, 1949-1960.

(89) Hörtensteiner, S.; Kräutler, B. *Biochim. Biophys. Acta* 2011, 1807, 977-988.

(90) Kräutler, B. *Chem. Soc. Rev.* 2014, 43, 6227-6238.

(91) Kräutler, B. *Angew. Chem. Int. Ed* 2016, 55, 4882-4907.

The foregoing is illustrative of the present invention, and is not to be construed as limiting thereof. The invention is defined by the following claims, with equivalents of the claims to be included therein.

That which is claimed is:

1. A method of making a compound of Formula I:

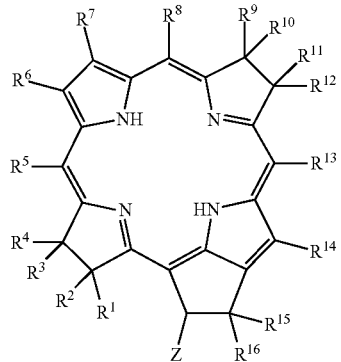
(I)

wherein:

$R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, a hydrophilic group, a linking group, a surface attachment group, and a targeting group, wherein the hydrophilic group is selected from the group consisting of an ionic group, a polar group, a polyol group, and a polyalkylene oxide group, and the surface attachment group is selected from the group consisting of an alkenyl, alkynyl, alcohol, thiol, selenyl, phosphono, telluryl, cyano, amino, formyl, halo, boryl, and carboxylic acid group;

or $R^1$ and $R^2$ together are =O or spiroalkyl;

or $R^3$ and $R^4$ together are =O or spiroalkyl;

or $R^9$ and $R^{10}$ together are =O or spiroalkyl;

or $R^{11}$ and $R^{12}$ together are =O or spiroalkyl;

or $R^5$ and $R^6$ together represent a fused aromatic or heteroaromatic ring system;

or $R^6$ and $R^7$ together represent a fused aromatic or heteroaromatic ring system;

or $R^{13}$ and $R^{14}$ together represent a fused aromatic or heteroaromatic ring system;

$R^{15}$ and $R^{16}$ together are =O; and

Z is —$CO_2R^{17}$, wherein $R^{17}$ is selected from the group consisting of hydrogen, alkyl, and aryl;

the method comprising condensing a compound of Formula II and a compound of Formula III in a composition comprising a first solvent to produce an intermediate, wherein the intermediate is a compound of Formula VI:

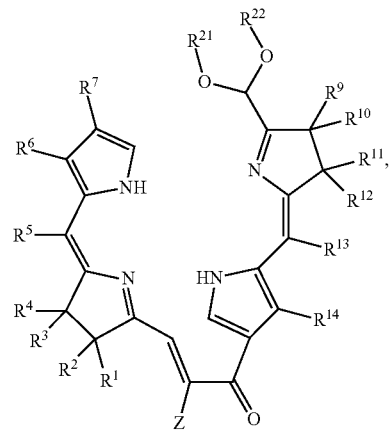
(VI)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and Z are each as provided above, and $R^{21}$ and $R^{22}$ are each an alkyl;

wherein the compound of Formula II has a structure of:

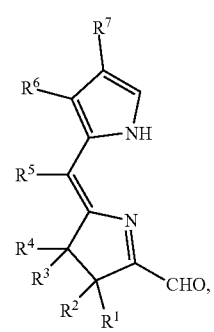
(II)

wherein $R^1$, $R^2$, $R^3$, $R^4$, $R^5$, $R^6$, and $R^7$ are each as provided above;

wherein the compound of Formula III has a structure of:

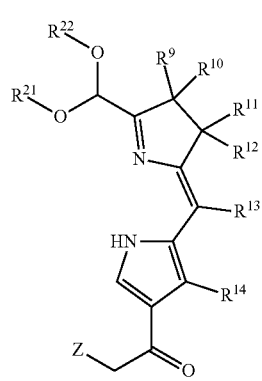
(III)

wherein $R^9$, $R^{10}$, $R^{11}$, $R^{12}$, $R^{13}$, $R^{14}$, $R^{21}$ and $R^{22}$ are each as provided above; and condensing the intermediate in a second solvent in the presence of an acid to produce the compound of Formula I.

2. The method of claim 1, further comprising metalating the compound of Formula I to produce the metal conjugate of the compound of Formula I.

3. The method of claim 1, wherein $R^{17}$ is an alkyl.

4. The method of claim 2, wherein the compound is a metal conjugate with the metal selected from the group consisting of Pd, Pt, Mg, Zn, Al, Ga, In, Sn, Cu, Ni, Au, and Fe.

5. The method of claim 1, wherein at least one of $R^1$ through $R^{14}$ is a linking group.

6. The method of claim 1, wherein at least one of $R^1$ through $R^{14}$ is a hydrophilic group.

7. The method of claim 1, wherein at least one of $R^1$ through $R^{14}$ is a targeting group.

8. The method of claim 1, wherein:
$R^1$ is a hydrophilic group, and $R^2$, $R^3$, and/or $R^4$ is a linking group or targeting group; or
$R^2$ is a hydrophilic group, and $R^1$, $R^3$, and/or $R^4$ is a linking group or targeting group; or
$R^3$ is a hydrophilic group, and $R^1$, $R^2$, and/or $R^4$ is a linking group or targeting group; or
$R^4$ is a hydrophilic group, and $R^1$, $R^2$, and/or $R^3$ is a linking group or targeting group; or
$R^9$ is a hydrophilic group, and $R^{10}$, $R^{11}$, and/or $R^{12}$ is a linking group or targeting group; or
$R^{10}$ is a hydrophilic group, and $R^9$, $R^{11}$, and/or $R^{12}$ is a linking group or targeting group; or
$R^{11}$ is a hydrophilic group, and $R^9$, $R^{10}$, and/or $R^{12}$ is a linking group or targeting group; or
$R^{12}$ is a hydrophilic group, and $R^9$, $R^{10}$, and/or $R^{11}$ is a linking group or targeting group.

9. The method of claim 1, wherein:
$R^1$ is a linking group or targeting group, and $R^2$, $R^3$, and/or $R^4$ is a hydrophilic group; or
$R^2$ is a linking group or targeting group, and $R^1$, $R^3$, and/or $R^4$ is a hydrophilic group; or
$R^3$ is a linking group or targeting group, and $R^1$, $R^2$, and/or $R^4$ is a hydrophilic group; or
$R^4$ is a linking group or targeting group, and $R^1$, $R^2$, and/or $R^3$ is a hydrophilic group; or
$R^9$ is a linking group or targeting group, and $R^{10}$, $R^{11}$, and/or $R^{12}$ is a hydrophilic group; or
$R^{10}$ is a linking group or targeting group, and $R^9$, $R^{11}$, and/or $R^{12}$ is a hydrophilic group; or
$R^{11}$ is a linking group or targeting group, and $R^9$, $R^{10}$, and/or $R^{12}$ is a hydrophilic group; or
$R^{12}$ is a linking group or targeting group, and $R^9$, $R^{10}$, and/or $R^{11}$ is a hydrophilic group.

10. The method of claim 1, wherein $R^7$ is a halogen.

11. The method of claim 1, wherein the step of condensing the compound of Formula II and the compound of Formula III in the composition comprising the first solvent is carried out using a Knoevenagel condensation reaction.

12. The method of claim 1, wherein the step of condensing the intermediate in the second solvent in the presence of the acid is carried out using a Nazarov cyclization reaction.

* * * * *

UNITED STATES PATENT AND TRADEMARK OFFICE
CERTIFICATE OF CORRECTION

PATENT NO. : 10,836,774 B2
APPLICATION NO. : 16/464728
DATED : November 17, 2020
INVENTOR(S) : Lindsey et al.

It is certified that error appears in the above-identified patent and that said Letters Patent is hereby corrected as shown below:

In the Specification

Column 7, Line 58: Please correct "10%" to read -- ±10% --

Column 9, Line 64: Please correct "S(OXO)OR" to read -- S(O)(O)OR --

Column 9, Line 67: Please correct "S(OXO)OH" to read -- S(O)(O)OH --

Column 20, Line 18: Please correct "$R^0$" to read -- $R^{10}$ --

Column 25, Line 57: Please correct "15N" to read -- $^{15}$N --

Column 26, Line 10: Please correct "Formula III" to read -- Formula II --

Column 26, Line 16: Please correct "Formula H and the compound of Formula II" to read -- Formula II and the compound of Formula III --

Column 26, Line 45: Please correct "Formula H" to read -- Formula II --

Column 26, Line 60: Please correct "Formula H" to read -- Formula II --

Column 30, Line 13: Please correct "I, and/or" to read -- II, and/or --

Column 30, Line 30: Please correct "Formula H" to read -- Formula II --

Column 31, Line 5: Please correct "$R^1$" to read -- $R^4$ --

Column 31, Line 9: Please correct "$R^1$" to read -- $R^4$ --

Column 37, Line 32: Please correct "M-'cm'" to read -- $M^{-1}cm^{-1}$ --

Signed and Sealed this
Tenth Day of August, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,836,774 B2

Column 55, Line 39: Please insert a paragraph break between "Li et al." and "The present"

Column 58, Line 30: Please correct "numbering$^9$)" to read -- numbering$^{19}$) --

Column 59, Line 59: Please correct "co-workers$^2$" to read -- co-workers$^{22}$ --

Column 63, Line 21: Please correct "n-substituted" to read -- β-substituted --

Column 67, Line 54: Please correct "$\zeta_{Qy}$" to read -- $\lambda_{Qy}$ --

Column 70, Line 62: Please correct "3-pyrrolic" to read -- β-pyrrolic --

Column 73, Line 27: Please correct "e6 trimethyl" to read -- e$_6$ trimethyl --

Column 81, Line 26: Please correct "3J=2.1 Hz" to read -- $^3$J=2.1 Hz --

Column 81, Line 53: Please correct "$^2$J=12.4 Hz" to read -- $^3$J=12.4 Hz --

Column 82, Line 36: Please correct "3J=2.4 Hz" to read -- $^3$J=2.4 Hz --

Column 84, Line 67: Please correct "M=C$_{11}$HBrNO" to read -- M=C$_{11}$H$_8$BrNO --

Column 88, Line 6: Please correct "84 &μmol" to read -- 84 μmol --

Column 89, Line 55: Please correct "$\mu_{abs}$" to read -- $\lambda_{abs}$ --

Column 92, Line 23: Please correct "Gtlrdere" to read -- Gürdere --